US012704577B2

(12) United States Patent
Wang et al.

(10) Patent No.: US 12,704,577 B2
(45) Date of Patent: Aug. 11, 2026

(54) DIFFUSION DICTIONARY IMAGING (DDI) OF MICROSTRUCTURE AND INFLAMMATION

(71) Applicant: Washington University, St. Louis, MO (US)

(72) Inventors: Yong Wang, St. Louis, MO (US); Qing Wang, St. Louis, MO (US)

(73) Assignee: Washington University, St. Louis, MO (US)

( * ) Notice: Subject to any disclaimer, the term of this patent is extended or adjusted under 35 U.S.C. 154(b) by 287 days.

(21) Appl. No.: 17/644,433

(22) Filed: Dec. 15, 2021

(65) Prior Publication Data

US 2022/0187405 A1 Jun. 16, 2022
US 2023/0213604 A9 Jul. 6, 2023

Related U.S. Application Data

(60) Provisional application No. 63/125,586, filed on Dec. 15, 2020.

(51) Int. Cl.
*G01R 33/563* (2006.01)
*A61B 5/00* (2006.01)
(Continued)

(52) U.S. Cl.
CPC ........ *G01R 33/56341* (2013.01); *A61B 5/055* (2013.01); *A61B 5/414* (2013.01);
(Continued)

(58) Field of Classification Search
None
See application file for complete search history.

(56) References Cited

U.S. PATENT DOCUMENTS

2016/0349339 A1* 12/2016 Brady-Kalnay ....... G01R 33/50
2018/0329006 A1* 11/2018 Haldar ................ G01R 33/543
(Continued)

OTHER PUBLICATIONS

Horvat et al., "Diffusion-Weighted Imaging (DWI) With Apparent Diffusion Coefficient (ADC) Mapping as a Quantitative Imaging Biomarker for Prediction . . . ," (2019 Reb 27), J Magn Reson Imaging. Sep. 2019;50(3):836-846. (Year: 2019).*
(Continued)

*Primary Examiner* — Keith M Raymond
*Assistant Examiner* — Ashish S. Jasani
(74) *Attorney, Agent, or Firm* — Armstrong Teasdale LLP

(57) ABSTRACT

A computing device for diffusion dictionary imaging (DDI) of microstructure and inflammation of a patient is provided. The DDI computing device is connected to other computing devices, such as a magnetic resonance imaging (MRI) scanner. The DDI computing device receives magnetic resonance (MR) signals from the MRI scanner. Once received, the DDI computing device records the one or more MR signals to a memory device. The DDI computing device computationally processes the one or more MR signals to reconstruct a diffusion MRI image using diffusion dictionary data. The MR signals include values that are used as input to algorithms of the DDI data to reconstruct the diffusion MRI image. A database is used to store DDI data, artificial intelligence (AI) data, diffusion dictionary data, and MR data.

20 Claims, 56 Drawing Sheets
(50 of 56 Drawing Sheet(s) Filed in Color)

(51) Int. Cl.
*A61B 5/055* (2006.01)
*G01R 33/56* (2006.01)
*G06N 20/00* (2019.01)
*G16H 30/40* (2018.01)

(52) U.S. Cl.
CPC ......... *G01R 33/5608* (2013.01); *G06N 20/00* (2019.01); *G16H 30/40* (2018.01)

(56) References Cited

U.S. PATENT DOCUMENTS

| | | | | |
|---|---|---|---|---|
| 2021/0003650 | A1 * | 1/2021 | Amthor | G06F 18/2413 |
| 2021/0003651 | A1 * | 1/2021 | Kamiguchi | G06N 3/045 |
| 2021/0259775 | A1 * | 8/2021 | Kustra | A61B 90/37 |
| 2022/0414972 | A1 * | 12/2022 | Rohrer | A61B 5/055 |

OTHER PUBLICATIONS

Rensonnet, Gaetan, "In vivo diffusion magnetic resonance imaging of the white matter microstructure from dictionaries generated by Monte Carlo simulations: development and validation," (Oct. 14, 2019), EPFL Thesis, <https://doi.org/10.5075/epfl-thesis-8497>. (Year: 2019).*

Kim et al., "A deep learning approach for magnetization transfer contrast MR fingerprinting and chemical exchange saturation transfer imaging," (Jul. 15, 2020), Neuroimage. Nov. 1, 2020:221:117165. (Year: 2020).*

Du et al., "Progress in mathematical modeling of gastrointestinal slow wave abnormalities," Frontiers in Physiology 8: 1136 (2018). doi.org/10.3389/fphys.2017.01136.

Kara et al., "ECG imaging to detect the site of ventricular ischemia using torso electrodes: a computational study," Frontiers in Physiology, 10:50 (2019). doi:10.3389/fphys.2019.00050.

Allegra et al., "Bayesian inverse methods for spatiotemporal characterization of gastric electrical activity from cutaneous multielectrode recordings," PLoS ONE 14(10): e0220315 (2019). https://doi.org/10.1371/journal.pone.0220315.

Wang et al., "Accuracy of electromyometrial imaging of uterine contractions in clinical environment," Computers in Biology and Medicine 116:103543 (2020). doi:10.1016/j.compbiomed.2019.103543.

Wu et al., "Noninvasive high-resolution electromyometrial imaging of uterine contractions in a translational sheep model," Science Translational Medicine 11(483): eaau1428 (2019). doi:10.1126/scitranslmed.aau1428.

Wang et al., "Spatial-dependent regularization to solve the inverse problem in electromyometrial imaging," Medical & Biological Engineering & Computing 58(8): 1651-1665 (2020). doi:10.1007/s11517-020-02183-z.

Wang et al., "Electromyometrial imaging dataset of electromyograms and isochrone maps under deformation/ electrical noise contaminations," Data in Brief, 28:105078 (2020). doi:10.1016/j.dib.2019.105078.

* cited by examiner

500A

| Voxel of Interest | Index | DTI | GQI | DBSI | | |
|---|---|---|---|---|---|---|
| | Corpus Callosum | | | | | |
| | [θ, φ] | [-10°, 28°] | [-11°,31°] | [-10°, 28°] | | |
| | % | 100 | N/A | 90 | 10 | |
| | $\lambda_{\parallel} / \lambda_{\perp}$ | 1.31/0.16 | N/A | 1.78/0.08 | | |
| | Corpus Callosum & CSF | | | | | |
| | [θ, φ] | [-6°,22°] | [-5°, 20°] | [-6°, 21°] | | |
| | % | 100 | N/A | 37 | 6 | 57 |
| | $\lambda_{\parallel} / \lambda_{\perp}$ | 1.61/0.58 | N/A | 1.79/0.10 | | |

FIG. 7G

| Group | Consent | 12 wk | 20 wk | 32 wk | 36 wk | W/D | Pregnant | Delivered |
|---|---|---|---|---|---|---|---|---|
| Low Risk | 86 | 56 | 34 | 17 | 23 | 34 | 11 | 37 |
| High Risk | 27 | 22 | 18 | 13 | 9 | 6 | 2 | 18 |

FIG. 10B

Inflammation Index

Perfusion Index

32 Weeks

| Classification Accuracy | 6 Months Only | 12 Months Only | 6 & 12 Months |
| --- | --- | --- | --- |
| DDI+ Random Forest | 87.25% | 94.21% | / |
| DDI+ Deep Learning | 90.05% | 95.40% | / |
| Surface Area +Volume (2017 Nature) | / | / | 94% |

FIG. 12C

DIFFUSION DICTIONARY IMAGING (DDI) OF MICROSTRUCTURE AND INFLAMMATION

CROSS-REFERENCE TO RELATED APPLICATIONS

This application claims the benefit of U.S. Provisional 63/125,586, filed Dec. 15, 2020, which is hereby incorporated by reference in its entirety.

STATEMENT REGARDING FEDERALLY SPONSORED RESEARCH OR DEVELOPMENT

This invention was made with government support under R01AG053548 awarded by the National Institutes of Health. The government has certain rights in this invention.

FIELD OF THE INVENTION

The present disclosure relates to systems and methods for imaging neuroinflammation, and in particular to systems and methods for imaging neuroinflammation using diffusion MR imaging.

BACKGROUND OF THE INVENTION

Inflammation is a key pathology process involved in multiple disease conditions and affects a large portion of the population across the life span. Accurate imaging of the inflammation in the affected organ (brain, joint, muscle, etc.) will be critical for accurate diagnosis, optimizing treatment, and clinical outcome monitoring.

The best existing technique of inflammation imaging makes use of Positron emission tomography (PET), a functional imaging technique that uses radioactive substances known as radiotracers to visualize and measure pathway changes during inflammation. While extensive research and resources have been invested in developing a sensitive and specific PET tracer for inflammation, a PET neuroinflammation tracer has not yet been established. Moreover, the radioactive nature of PET tracer and complicated/expensive imaging process greatly limit its application to a subset of patients and cases, even if successfully developed.

In contrast to PET, diffusion MRI utilizes endogenous contrast from water molecules abundant in the human body. However, to date, the use of diffusion MRI to image inflammation poses a challenge using existing techniques.

BRIEF SUMMARY OF THE INVENTION

In a first aspect, a Diffusion Dictionary Imaging (DDI) computing device comprising at least one processor in communication with a memory device may be provided. The at least one processor may be configured to: receive, from at least one user device, one or more magnetic resonance (MR) signals, record the one or more MR signals to the at least one memory device; retrieve one or more DDI algorithms from the at least one memory device; process the one or more MR signals to reconstruct a diffusion MRI image using the retrieved one or more DDI algorithms; and output the reconstructed diffusion MRI image. The DDI computing device may include additional, less, or alternate functionality, including that discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure will become better understood when the following detailed description is read with reference to the accompanying drawings in which like characters represent like parts throughout the drawings, wherein:

FIGS. 7A-7G illustrate aspects of diffusion tensor imaging (DTI) to DBSI in accordance with at least one embodiment of the present disclosure.

FIGS. 10A-10L illustrate aspects of DDI application in a human placenta in accordance with at least one embodiment of the present disclosure.

FIGS. 12A-12G illustrate aspects of inflammation imaging in accordance with at least one embodiment of the present disclosure.

Figure 1:
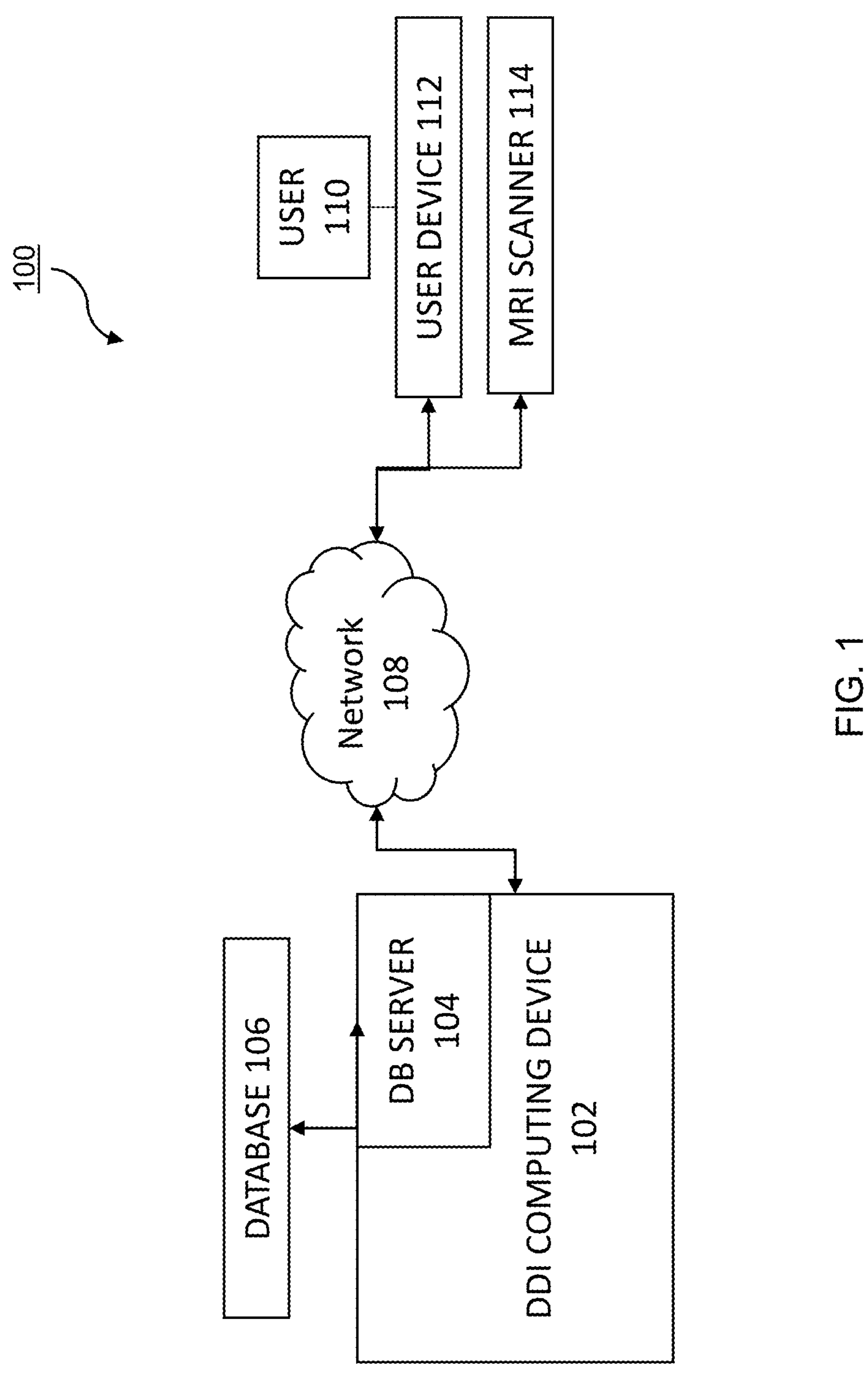
FIG. 1 illustrates an exemplary Diffusion Dictionary Imaging (DDI) computing system in accordance with an exemplary embodiment of the present disclosure.

Unless otherwise indicated, the drawings provided herein are meant to illustrate features of embodiments of the disclosure. These features are believed to be applicable in a wide variety of systems including one or more embodiments of the disclosure. As such, the drawings are not meant to include all conventional features known by those of ordinary skill in the art to be required for the practice of the embodiments disclosed herein.

DETAILED DESCRIPTION

The present embodiments may relate to, inter alia, systems and methods for the development of Diffusion Dictionary Imaging (DDI). More specifically, the development of a diffusion MRI imaging technique that employs an FDA-approved diffusion weight sequence on a clinical MRI scanner with multiple diffusion weighting and directions. In one exemplary embodiment, the systems and methods may be performed by a Diffusion Dictionary Imaging (DDI) computing device. The systems and methods may employ diffusion MRI to image inflammation, which may be widely and longitudinally applied at an affordable price. Further, the systems and methods described herein may be well-suited to meet commercial needs for an accurate, safe, and cheap inflammation imaging technique.

In the exemplary embodiment, the DDI computing device may be in communication with one or more of a plurality of user computing devices, a plurality of server computing devices, or a combination thereof.

In an exemplary embodiment, the systems and methods provided by a DDI computing device may overcome at least a portion of the limitations of existing diffusion MRI imaging techniques in a multitude of ways. For example, the DDI computing device may be designed and employed to provide a comprehensive diffusion dictionary containing various diffusion patterns within certain pathophysiology ranges. With this diffusion dictionary, the DDI computing device may transform raw diffusion images into direction space through a regularized-linear transformation. Compared to existing diffusion MRI imaging techniques, the DDI computing device may model different types of complicated microstructures in a uniform way, which would significantly improve the computation speed. Additionally, with the help of compress sensing, DDI can also process diffusion MRI images with a small number of diffusion weightings in clinical settings.

In some embodiments, a weighted apparent diffusion coefficient (wADC) may be defined based on the DDI computing device's computation to capture microstructure hallmarks (cell enlargement and upregulation cell membrane water channel) associated with immune cell activation during the inflammation process. In this example, the wADC may provide contrast sensitivity and specificity to immune cell activation.

The systems and methods described herein and provided by a DDI computing device hold great potential to provide low cost, accurate, safe, inflammation images for patients with various inflammatory conditions. Without using a radioactive tracer or contrast agent, algorithms implemented by the DDI computing device may extract inflammatory features from a patient's endogenous contrast, which makes it an ideal and safe solution, especially for patients who cannot tolerate (longitudinal) imaging using radioactive tracer or contact agents, such as pregnant women, newborns, patients with complications, etc.

Exemplary System for Diffusion Dictionary Imaging

FIG. 1 depicts an exemplary Diffusion Dictionary Imaging (DDI) computing system 100. DDI computing system 100 includes a DDI computing device 102. DDI computing device 102 may include a database server 104 and may be in communication with, for example, a database 106. DDI computing device 102 may be connected via a network, such as network 108, to one or more networked devices, such as user device 112 or MRI scanner 114. User device 112 may be associated with a computer operator, such as user 110. User device 112 may be, for example, a mobile device, a tablet PC, a portable computer, or the like. In some embodiments, the DDI computing device 102 may be part of user device 112. For sake of brevity, a single user device is shown, however it is understood that the configuration may comprise of multiple user devices controlled by a plurality of users. Database 104 may be implemented as a local storage option. Alternatively, database 104 may be a remote storage location, such as a cloud storage option.

Network 108 may be any network that allows local area or wide area communication between devices. For example, network 108 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem.

In some embodiments, the DDI system may provide methods implemented by a computing device, such as DDI computing device 102, and a scanner, such as MRI scanner 114, that is operatively coupled to a user device, such as user device 110. The computing device 102 may, for example, receive and record MR signals detected by MRI scanner 114. Additionally, computing device 102 may computationally process the received MR signals to reconstruct a diffusion MRI image in accordance with one or more DDI methods described herein. Additionally, or alternatively, one or more DDI methods may be implemented that at least partially use machine learning methods. In other aspects, the computing device 102 may be configured to perform a plurality of tasks associated with one or more DDI methods of modifying the neural state of a subject using an artificial intelligence model.

Exemplary Client Computing Device

Figure 2:
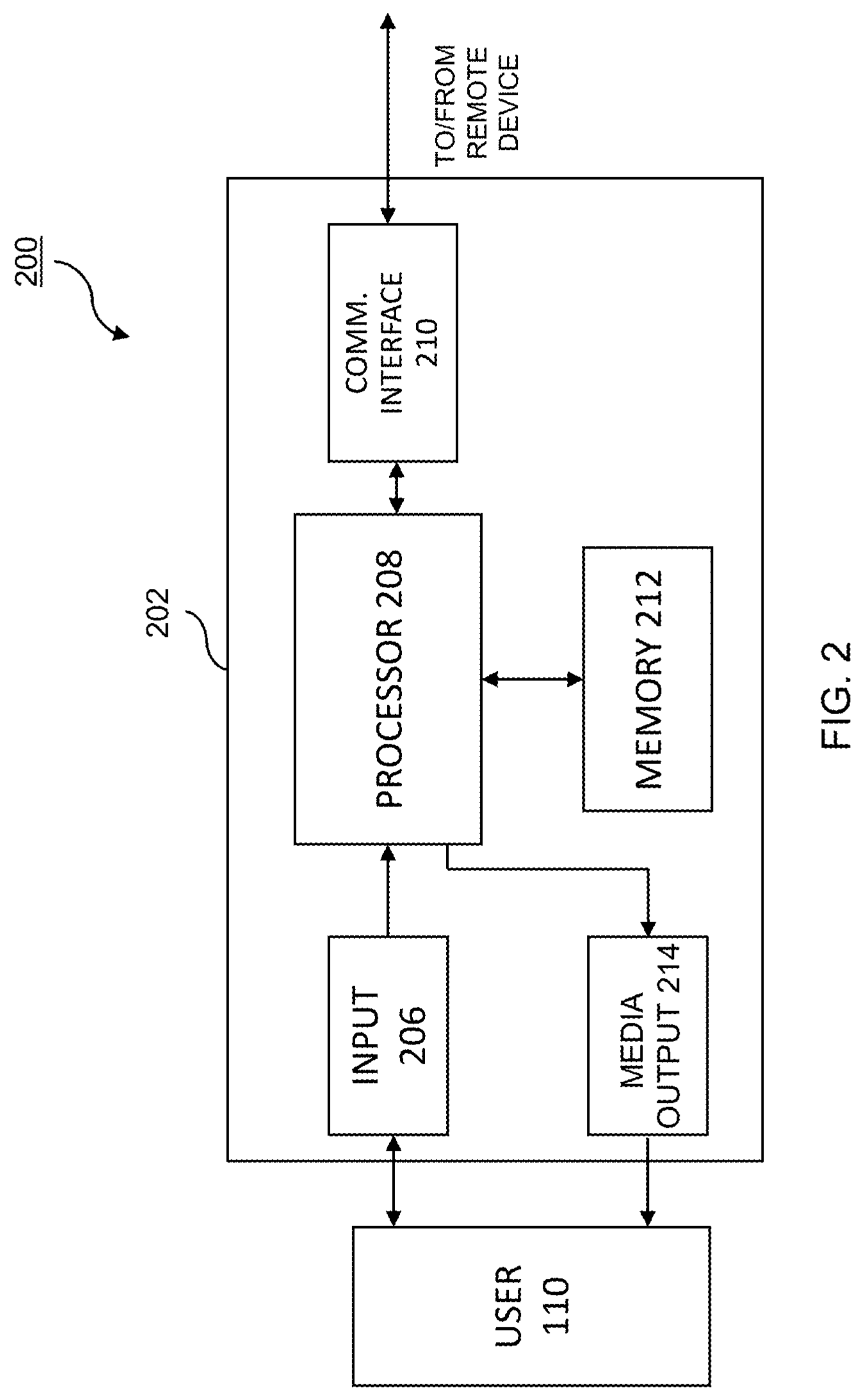
FIG. 2 illustrates an exemplary client computing device that may be used with the DDI computing system illustrated in FIG. 1.

FIG. 2 illustrates diagram 200 of an exemplary client computing device 202, such as user device 112 shown in FIG. 1, and operable by a user, such as user 110. Computing device 202 may include, but is not limited to, an input device 206, processor 208, a communications interface 210, a memory 212, and a media output component 214. Other embodiments may include different or additional components shown in FIG. 2.

Computing device 202 may include a processor 208 for executing instructions. In some embodiments, executable instructions may be stored in a memory area 212. Processor 208 may include one or more processing units (e.g., in a multi-core configuration). Memory area 212 may be any device allowing information such as executable instructions and/or other data to be stored and retrieved. Memory area 212 may include one or more computer readable media.

In the exemplary embodiment, computing device 202 may include a media output component 214 for presenting information to a user, such as user 110. Media output component 214 may be a component capable of conveying information to user 110. In some embodiments, media output component 214 may include an output adapter such as a video adapter, an audio adapter, or a combination thereof. An output adapter may be operatively coupled to processor 208 and operatively coupled to an output device such as a display device (e.g., a liquid crystal display (LCD), a light-emitting diode (LED) display, an organic light-emitting diode (OLED) display, a cathode ray tube (CRT) display, an "electronic ink" display, a projected display, etc.) or an audio output device (e.g., a speaker arrangement or headphones).

In some embodiments, client computing device 202 may include an input device 206 for receiving input from user 110. Input device 206 may include, but is not limited to, a keyboard, a pointing device, a mouse, a stylus, a touch-sensitive panel (e.g., a touch pad or a touch screen), or an audio input device. A single component, such as a touch screen device, may function as both an output device of media output component 214 and an input device of input device 206.

Additionally, or alternatively, client computing device 202 may include a communication interface 210, which may be communicatively coupled to a remote device, such as DDI computing device 102 of FIG. 1. Communication interface 210 may include, but is not limited to, a wired or wireless network adapter and wireless data transceiver for use with a mobile phone network (e.g., Global System for Mobile communications (GSM), 3G, 4G, or Bluetooth) or other mobile data networks (e.g., Worldwide Interoperability for Microwave Access (WIMAX)). The systems and methods disclosed herein are not limited to any certain type of short-range or long-range networks.

Memory area 212 may, for example, store non-transitory computer readable instructions that cause the processor to perform actions as described herein. That is, the instructions may configure the computing device to perform one or more of the operations described herein. For example, the instructions stored in the memory 212 may cause the processor to receive and record MR signals detected by an MRI scanner, such as MRI scanner 114. Additional instructions may be stored in memory 212 that may cause the processor to computationally process the received MR signals to reconstruct a diffusion MRI image in accordance with one or more DDI methods. In some embodiments, memory area 212 may include instructions that cause the processor to provide a user interface to user 110 via media output component 214. Additionally, or alternatively, instructions may cause the processor to receive and process input from input device 212. A user interface may include, among other possibilities, a web browser or a client application. Web browsers may enable users, such as user 204, to display and interact with media and other information typically embedded on a web page or a website.

Memory area 208 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAN). The above memory types are examples only and are thus not limiting as to the types of memory usable for the storage of a computer program.

Example Server Computing Device

Figure 3:
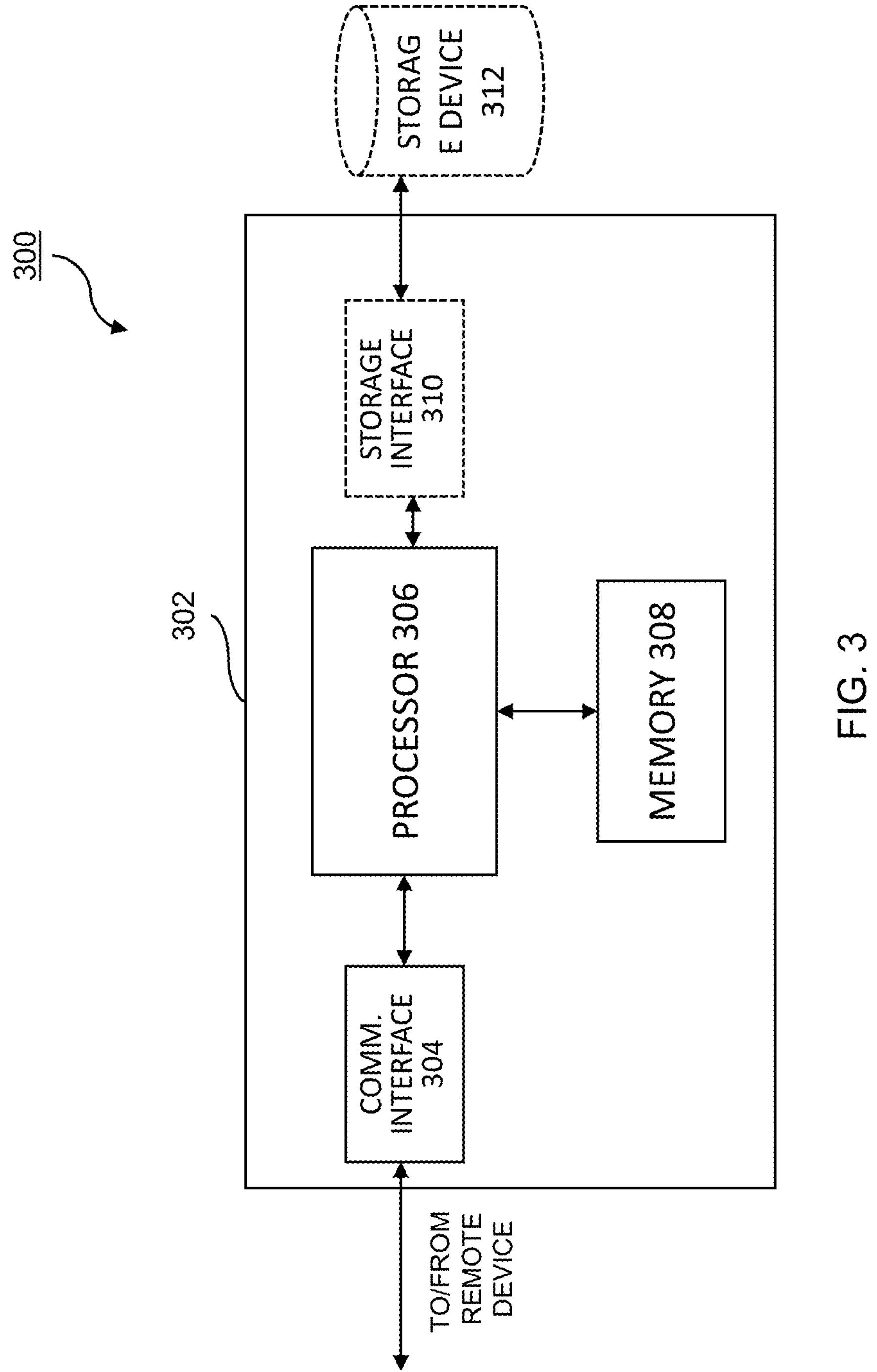
FIG. 3 illustrates an exemplary server system that may be used with the DDI computing system illustrated in FIG. 1.

FIG. 3 depicts a block diagram 300 of an exemplary server computing device 302 that may be used with DDI computing system 100 illustrated in FIG. 1. Server system 302 may be, for example, DB server device 104 (shown in FIG. 1).

In an exemplary embodiment, server system 302 may include a processor 306 for executing instructions. Instructions may be stored in a memory area 308. Processor 306 may include one or more processing units (e.g., in a multi-core configuration) for executing the instructions. The instructions may be executed within a variety of different operating systems on server computing device 302, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, Python, or other suitable programming languages, etc.).

Processor 306 may be operatively coupled to a communication interface 304 such that server computing device 302 may communicate with one or more networked devices, including, but not limited to, DDI computing device 102, user device 112, and MRI scanner 114 (all shown in FIG. 1), or another server system, for example.

Processor 306 may be coupled to a storage device 312, such as database 106 (shown in FIG. 1). Storage device 312 may be any computer-operated hardware suitable for storing or retrieving data. In some embodiments, storage device 312 may be integrated in server computing device 302. For example, server system 302 may include one or more hard disk drives as storage device 312. In other embodiments, storage device 312 may be external to server system 302 and may be accessed by a plurality of different server systems. For example, storage device 312 may include multiple storage units such as hard disks or solid-state disks in a redundant array of inexpensive disks (RAID) configuration. In some embodiments, storage device 312 may include a storage area network (SAN) or a network attached storage (NAS) system.

In some embodiments, processor 306 may be operatively coupled to storage device 312 via a storage interface 310. Storage interface 310 may be any component capable of providing processor 306 with access to storage device 312. Storage interface 310 may include, for example, an Advanced Technology Attachment (ATA) adapter, a Serial ATA (SATA) adapter, a Small Computer System Interface (SCSI) adapter, a RAID controller, a SAN adapter, a network adapter, or any component providing processor 306 with access to storage device 312.

Memory area 306 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are exemplary only and are thus not meant to limit the types of memory usable for a storage device of the computing systems described herein.

Example Component Configuration

Figure 4:
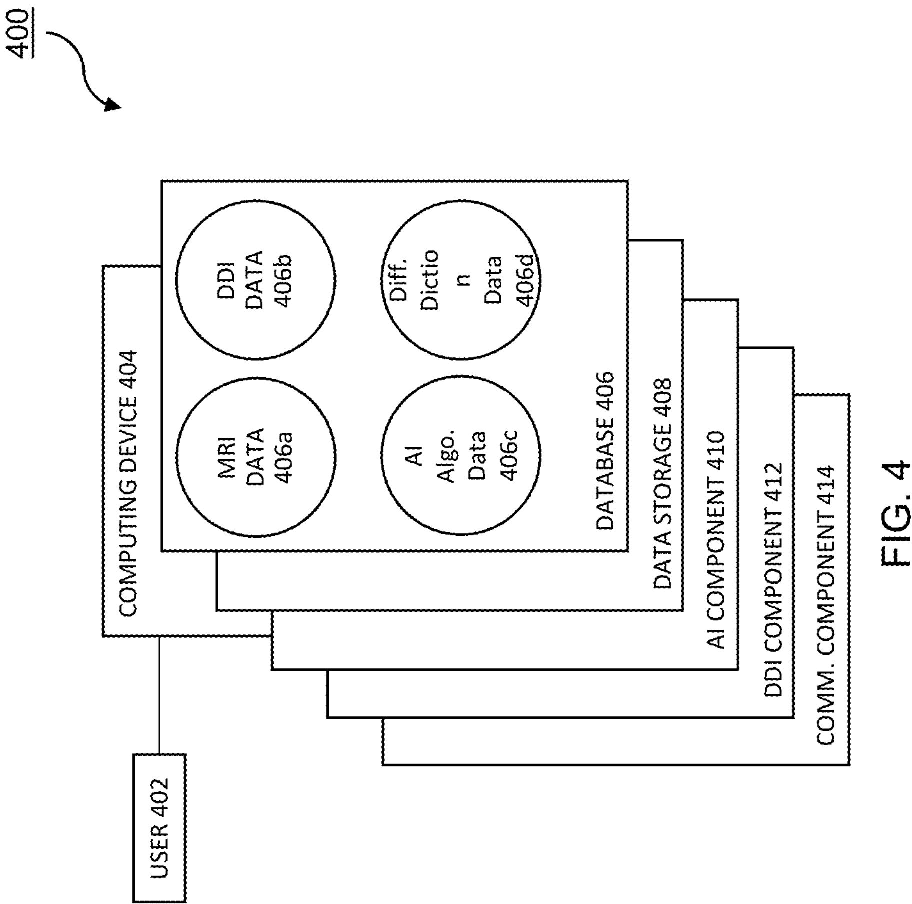
FIG. 4 illustrates an exemplary block diagram schematically illustrating a server system in accordance with an exemplary embodiment of the present disclosure.

FIG. 4 depicts an exemplary component configuration 400 of computing device **40*f*4 operable by user 402. Computing device 404 may include a database 406 along with other related computing components including, but not limited to, data storage 408, AI component 410, DDI component 412, and communications component 414. In some embodiments, computing device 404 is similar to computing device 102, and database 406 is similar to database 106 (shown in FIG. 1). A user 402 may access components of computing device 404**.

In some embodiments, database 406 may include, but is not limited to, magnetic resonance (MR) data **406*a*, DDI data 406*b*, artificial intelligence (AI) algorithm data 406*c*, and diffusion dictionary data 406*d*. Suitable AI algorithm data 406*c* may include, for example, values of parameters defining an AI model used to extract features from a plurality of MR signals obtained using an MRI scanner. MR signals may be indicative of one or more microstructures. Additionally or alternatively, an AI model may be implemented to reconstruct a diffusion MR image in accordance with one or more DDI methods described herein. In one example, MR data 406*a* may include, but is not limited to, values defining MR signals obtained using an MRI scanner. DDI data 406*b*** may include, for example, any values defining equations and/or algorithms used to implement DDI methods described herein. Additionally, diffusion dictionary data

406*d* may include, but is not limited to, any values indicative of MR signals characterizing at least one or more microstructures to be imaged in accordance with a disclosed DDI method.

Computing device 404 may include components that perform specific tasks. For example, computing device 404 may include data storage device 408, AI component 410, DDI component 412, and communication component 414. Data storage device 408 may be configured to store data received or generated by computing device 404, such as any of the data stored in database 406 or any outputs of processes implemented by any component of computing device 404. The DDI component 412 may be configured to transform MR signals into diffusion MRI images of at least one microstructure in accordance with the DDI methods described herein. DDI component 412 and AI component 410 may operate in cooperation to transform MR signals into diffusion MRI images of at least one microstructure in accordance with the DDI methods described herein.

In some embodiments, AI component 410 may be configured to extract features of the brain signals obtained using the MRI scanner and/or reconstruct a diffusion MRI image of at least one microstructure in accordance with the disclosed DDI method. Further, AI component 410*a* may implement any suitable AI model or algorithm without limitation including, but not limited to, genetic algorithms, linear or logistic regression algorithms, instance-based algorithms, regularization algorithms, decision tree algorithms, Bayesian network algorithms, cluster analysis algorithms, association rule learning, supervised learning, unsupervised learning, reinforcement learning, artificial neural networks, deep learning, dimensionality reduction algorithms, and support vector machines.

Communication component 414 may be configured to enable communications between computing device 404 and other devices (e.g. user computing device 112 and MRI scanner 114, shown in FIG. 1) over a network, such as network 108 (shown in FIG. 1), or a plurality of network connections using predefined network protocols such as TCP/IP (Transmission Control Protocol/Internet Protocol).

Exemplary Implementations

In an exemplary embodiment, a DDI computing device, such as device 102, may implement a diffusion weighting sequence on a clinical MRI scanner with multiple diffusion weighting and directions. For example, the DDI computing device may analyze diffusion MRI images from two major perspectives.

In a first perspective, a DDI computing device may design and employ a comprehensive diffusion dictionary containing various diffusion patterns within certain pathophysiology ranges. With this diffusion dictionary, the DDI computing device may transform raw diffusion images into direction space through a regularized-linear transformation. The DDI computing device may model different types of complicated microstructures in a uniform way and the computation speed may be significantly improved. In addition, with the help of compress sensing, the DDI computing device may also process diffusion MRI images with a small number of diffusion weightings in clinical settings.

In a second perspective, a weighted apparent diffusion coefficient (wADC) may be defined based on a DDI computing device's computation to capture microstructure hallmarks (cell enlargement and upregulation cell membrane water channel) associated with immune cell activation during an inflammation process. wADC based on DDI may provide contrast sensitivity and specificity to immune cell activation. A DDI computing device may hold great potential to provide low cost, accurate, safe, inflammation images for patients with various inflammatory conditions. Without using a radioactive tracer or contrast agent, a DDI algorithm may, for example, extract inflammatory features from a patient's endogenous contrast, which makes it an ideal and safe solution, especially for patients who are unable to tolerate longitudinal imaging using radioactive tracer or contact agents, such as pregnant women, newborns, patients with complications, or the like.

Figure 5A:
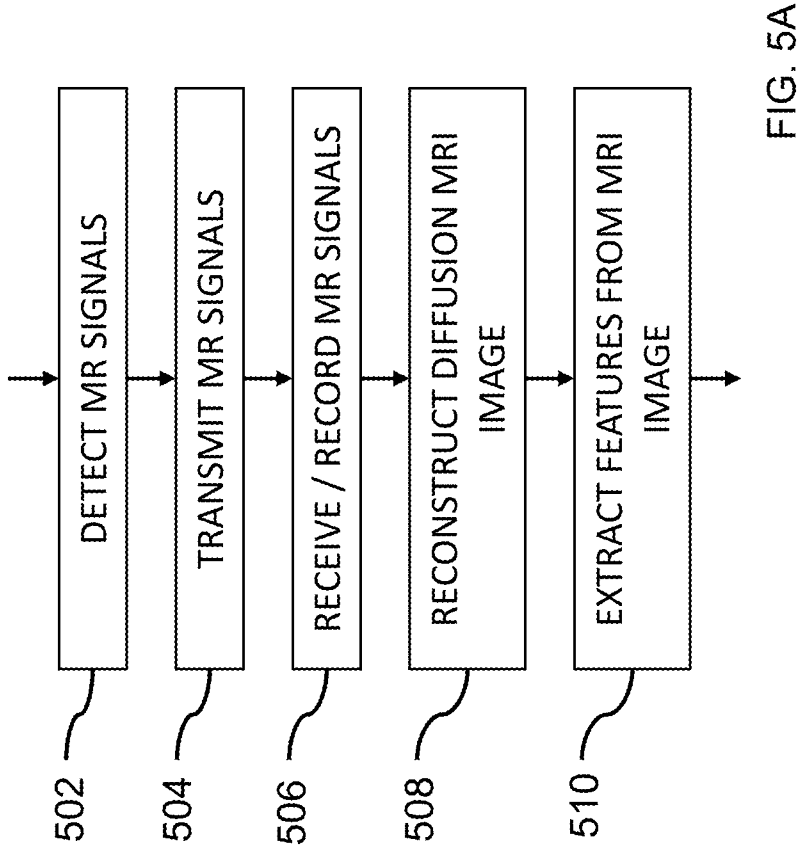
FIG. 5A illustrates an exemplary process 500A of constructing a diffusion MRI image in accordance with at least one embodiment of the present disclosure.

FIG. 5A depicts an exemplary flow diagram 500A of constructing a diffusion MRI image. Steps of diagram 500A may be implemented by networked computing devices, such as DDI computing device 102 and/or user computing device 112 (shown in FIG. 1). Flow 500A may start with the detection of MRI signals 502 by an MRI scanner, such as MRI scanner 114 (also shown in FIG. 1). The MRI signals may be transmitted 504 by a user computing device coupled to the MRI scanner, such as user computing device 112, and operated by a user, such as user 110 (shown in FIG. 1). Once sent from a computing device, the MR signals may be received 506 by another computing device, such as DDI computing device 102, and recorded on a memory device or other type of storage. Further, DDI computing device 102 may reconstruct 508 a diffusion MRI image based, at least in part, on the recorded MR signals. During reconstruction, DDI computing device may use, as input, one or more values that are based on the recorded MR signals as data inputs for a diffusion dictionary algorithm, or the like. The one or more values may, for example, include features of brain signals that represent at least one microstructure. In some embodiments, a combination of artificial intelligence algorithms, or models, may be used in combination with a diffusion dictionary algorithm. Features of the reconstructed MRI image may be extracted in block 510. Alternative embodiments may be implemented and flow diagram 500A is in no way meant to be limiting.

Figure 6A:
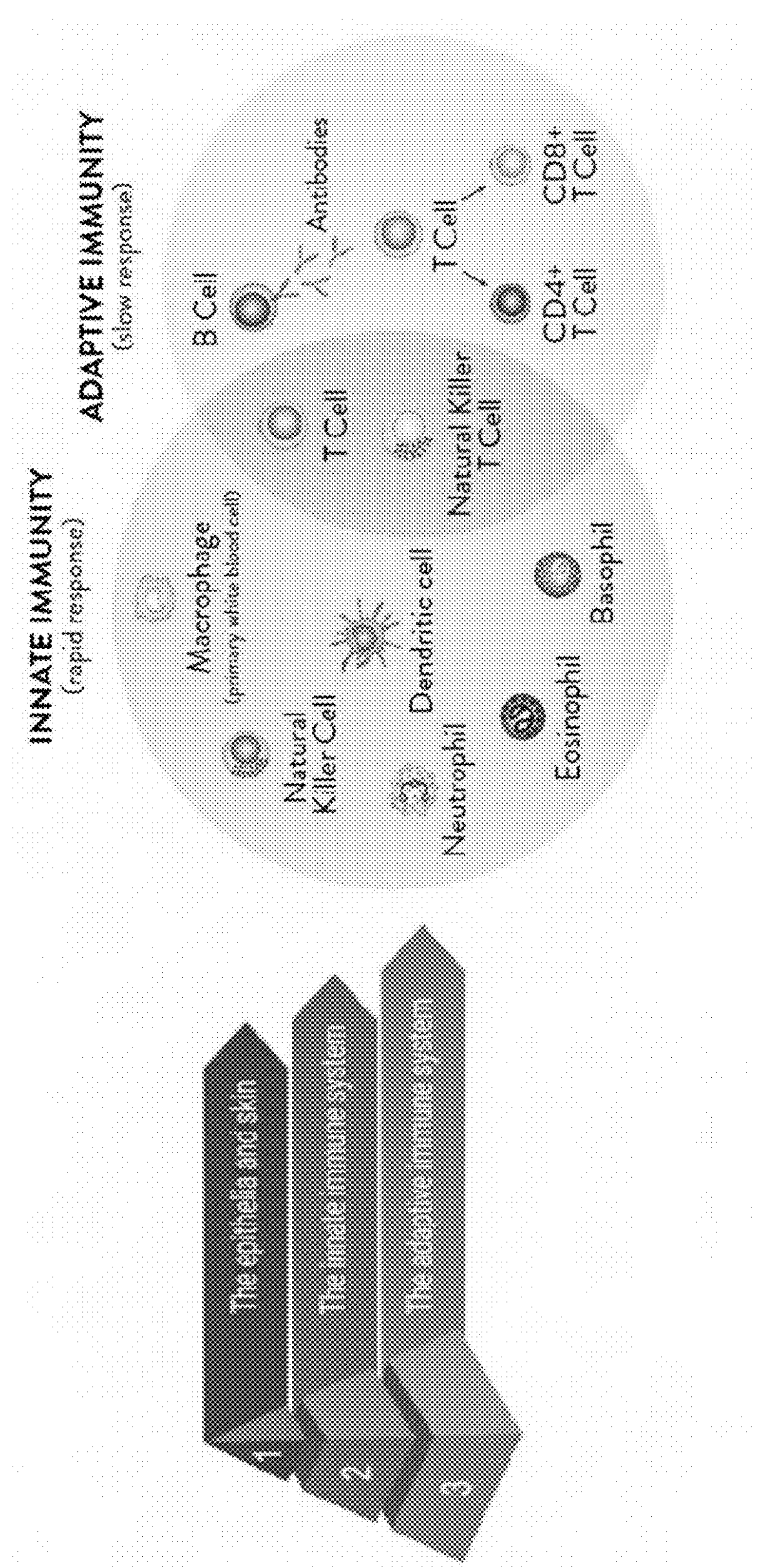
FIGS. 6A-6O illustrate aspects of diffusion MRI in accordance with at least one embodiment of the present disclosure.
Figure 6B:
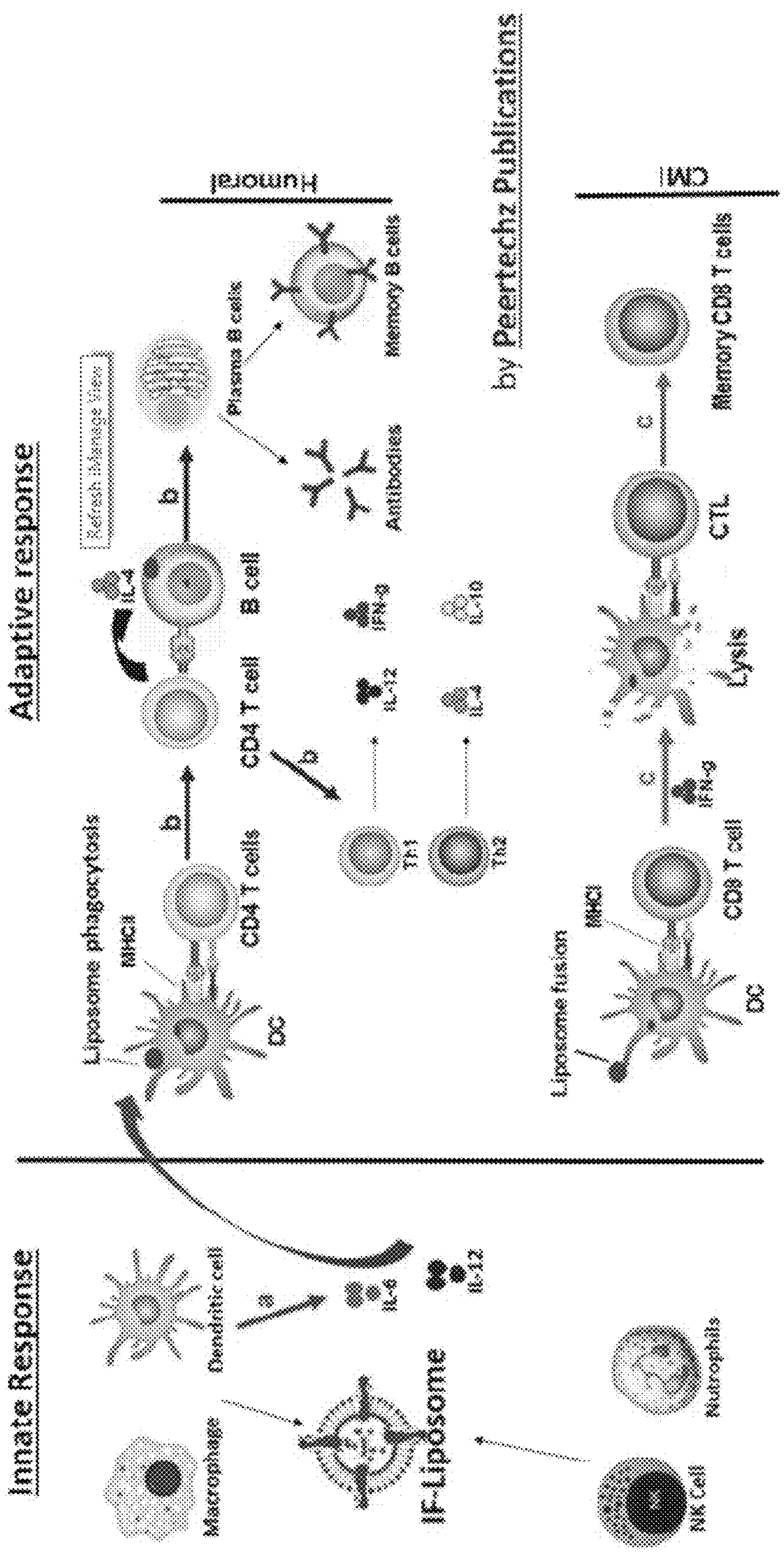
Figure 6C:
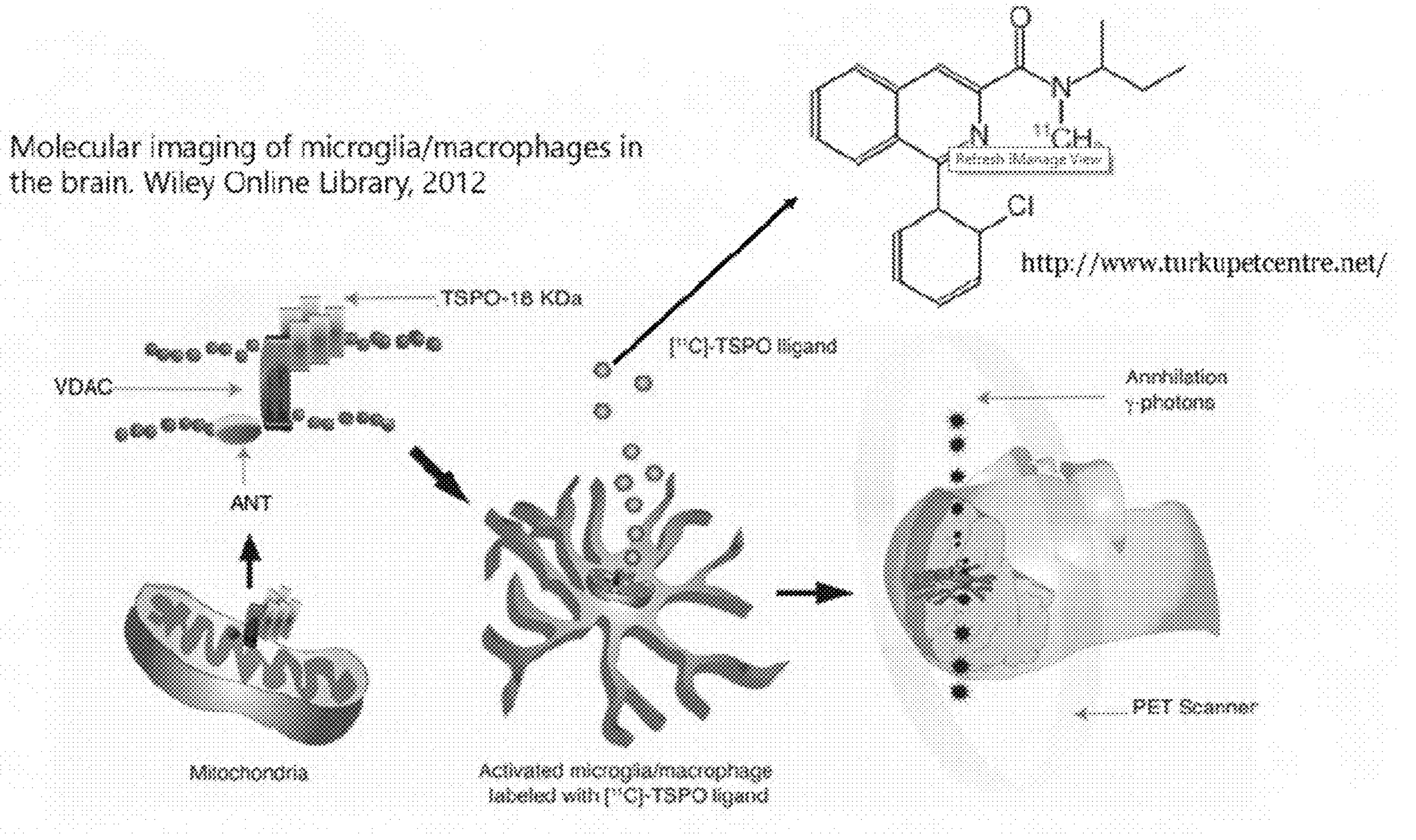
Figure 6D:
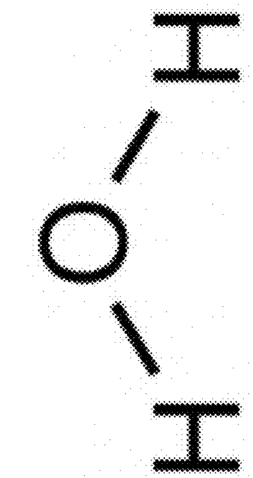
Figure 6D:
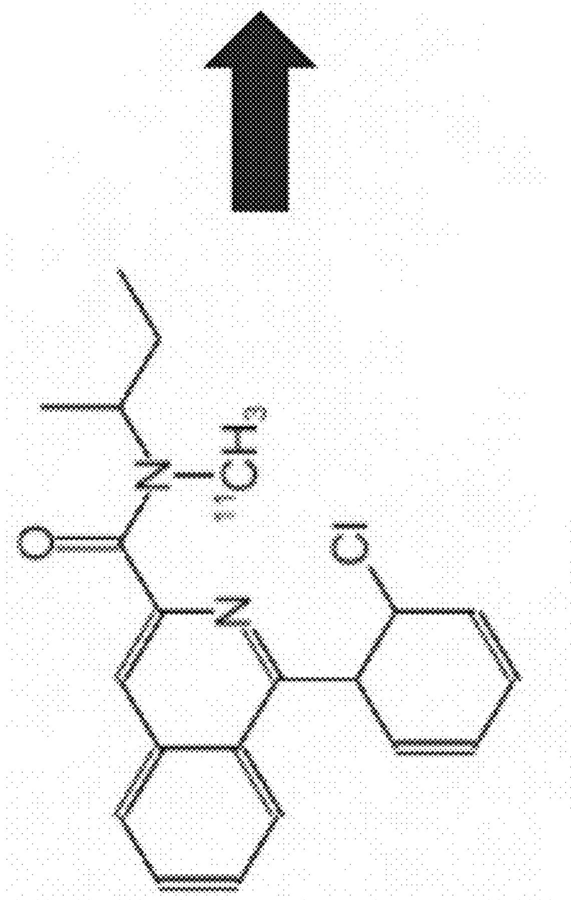
Figure 6E:
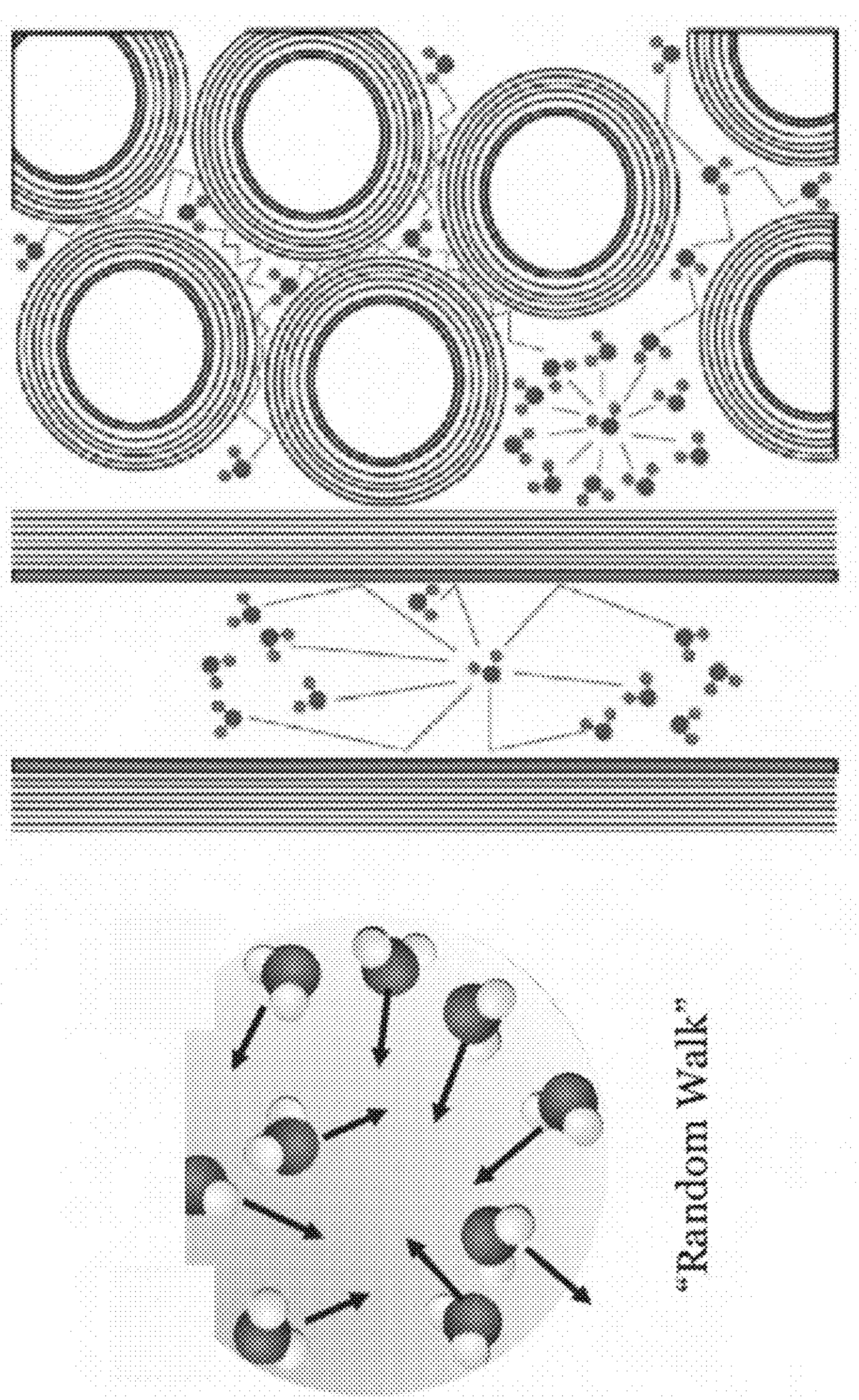
Figure 6F:
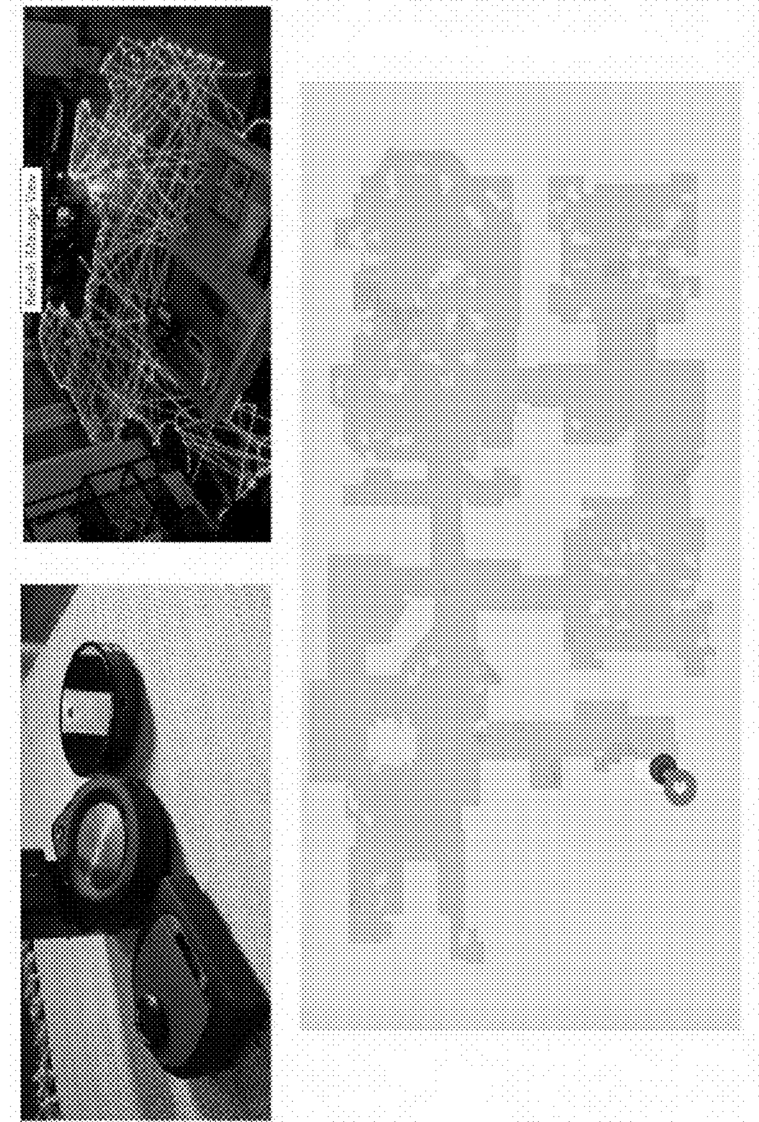
Figure 6G:
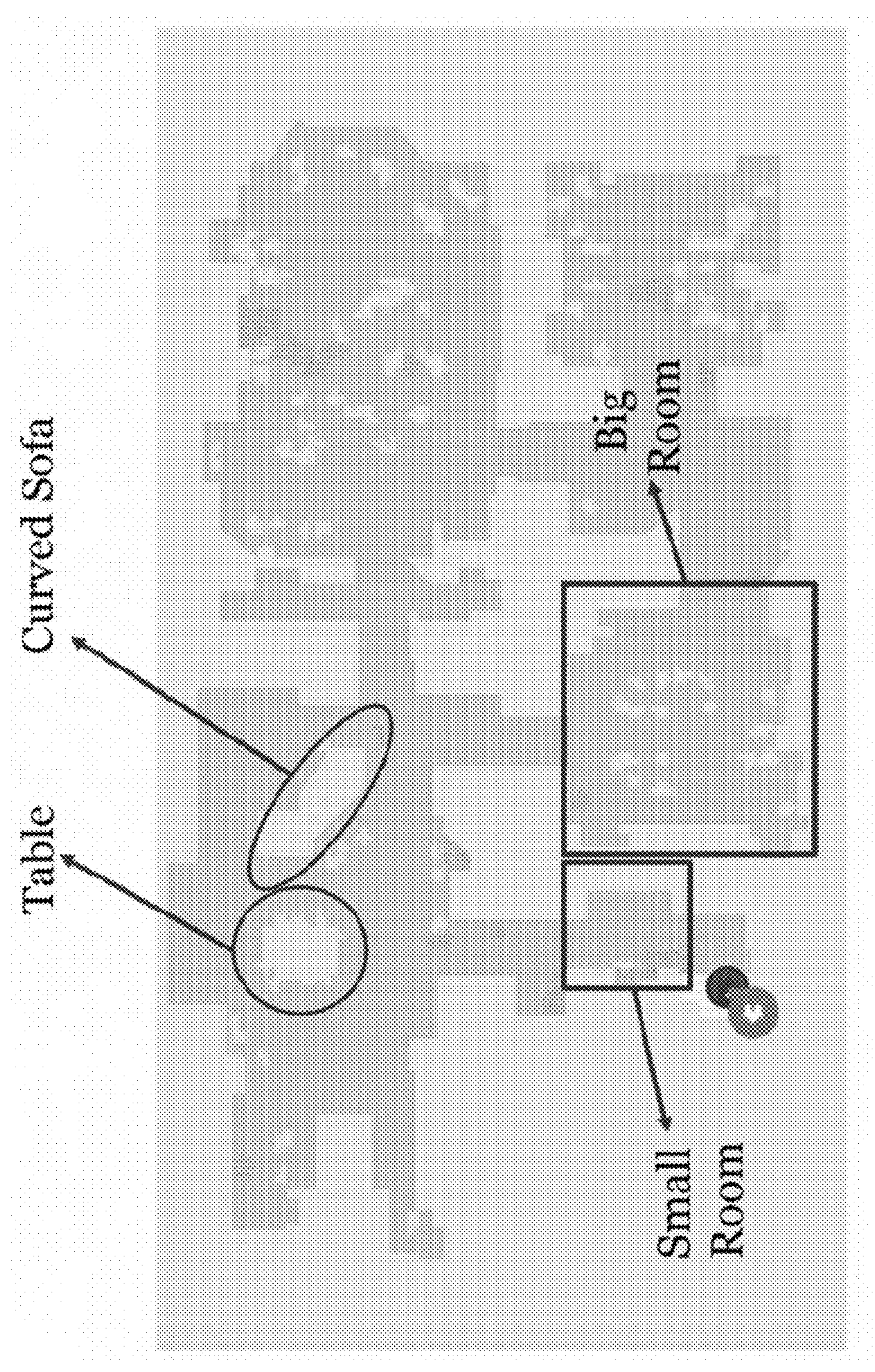
Figure 6H:
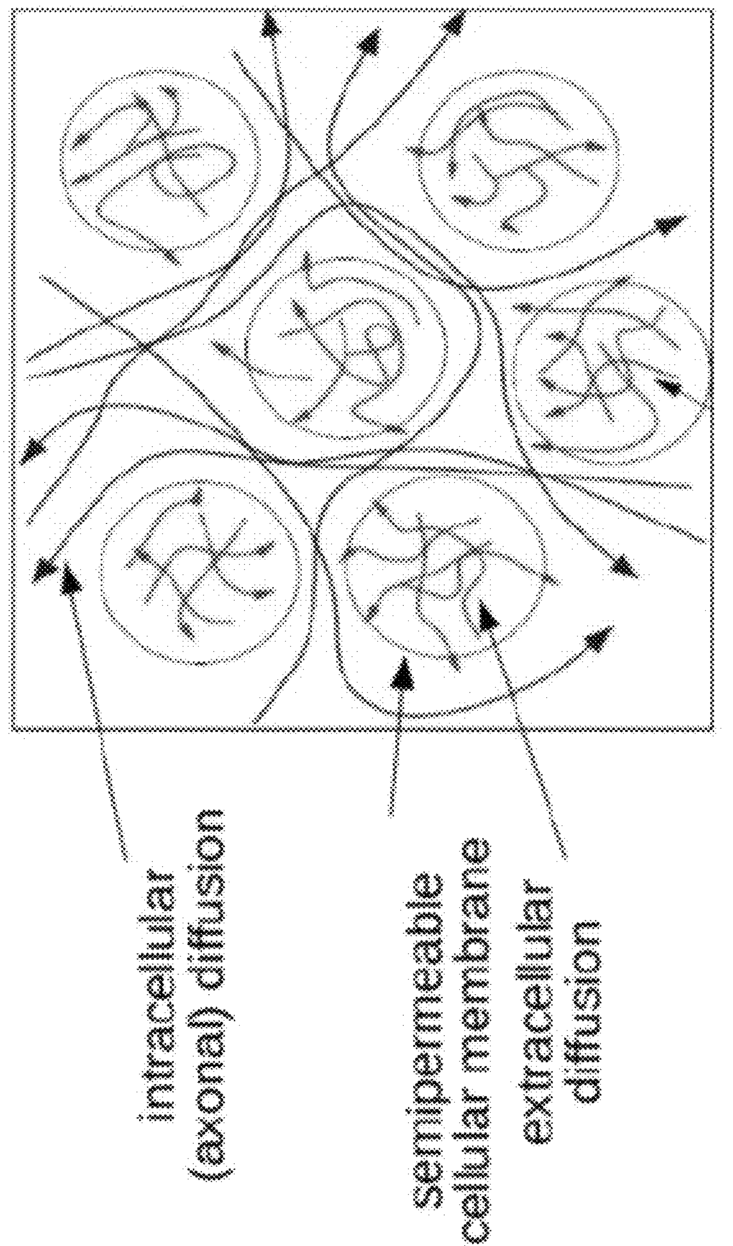
Figure 6I:
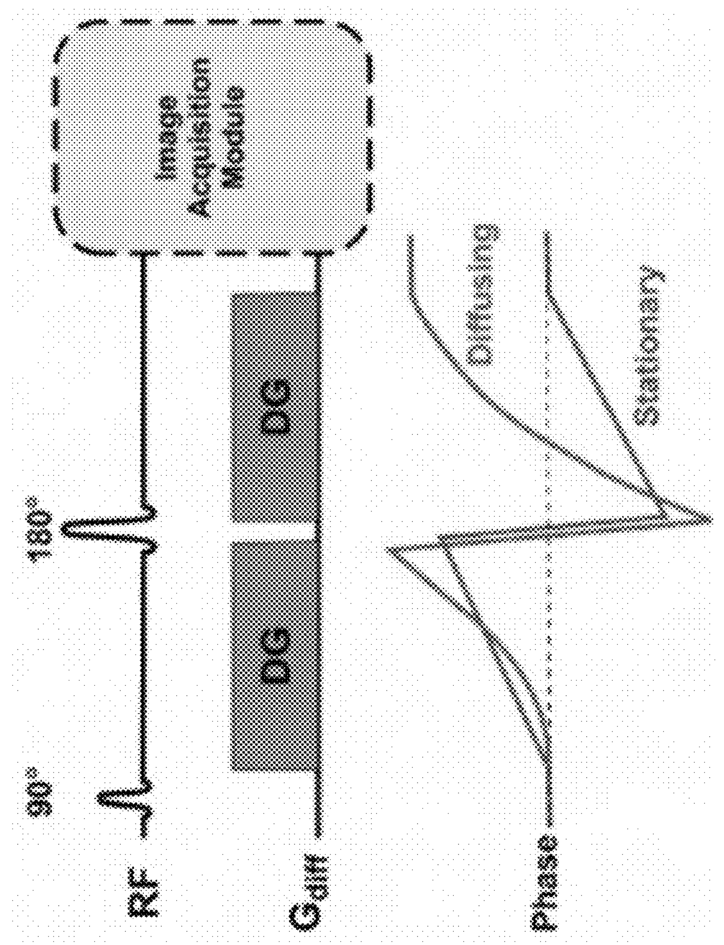
Figure 6J:
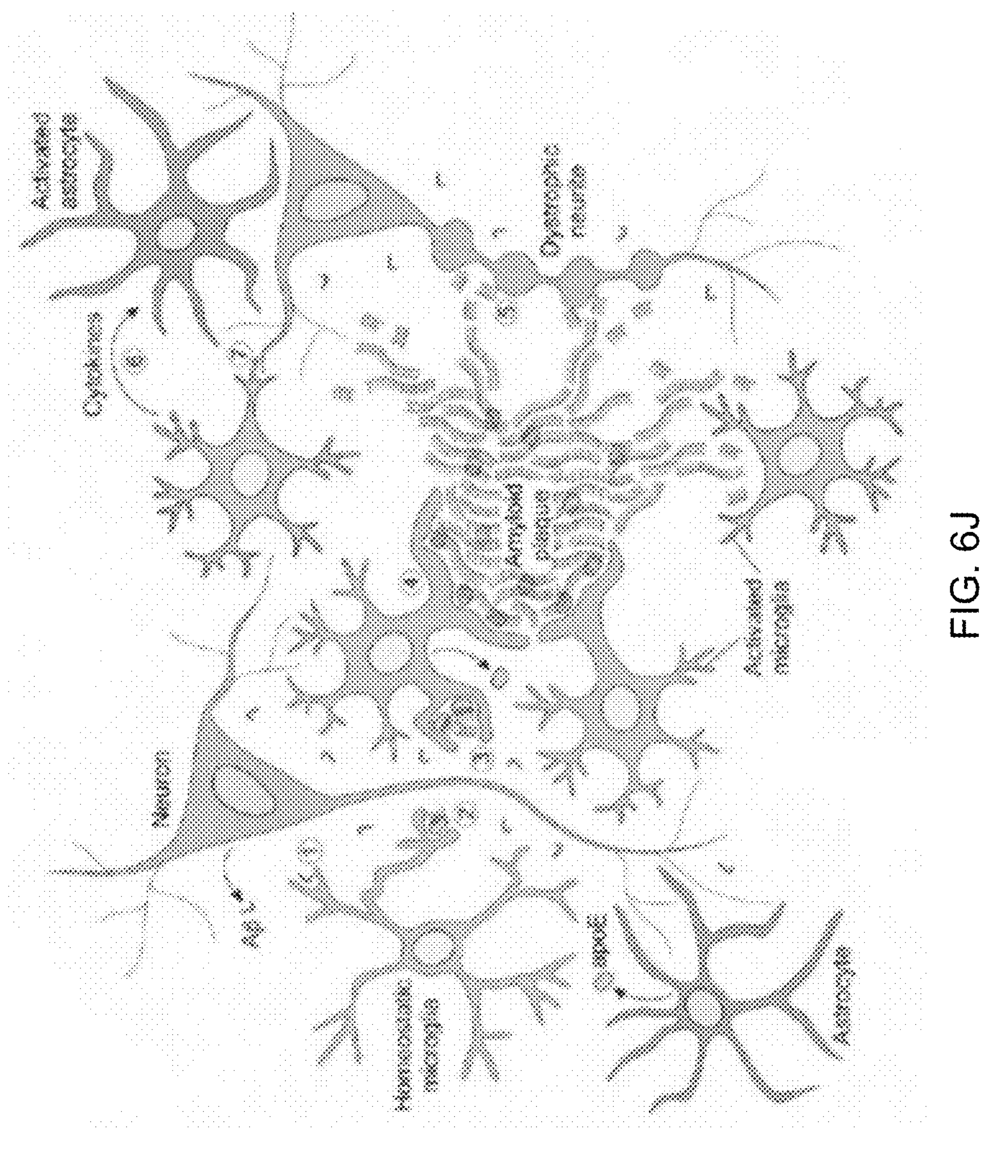
Figure 6K:
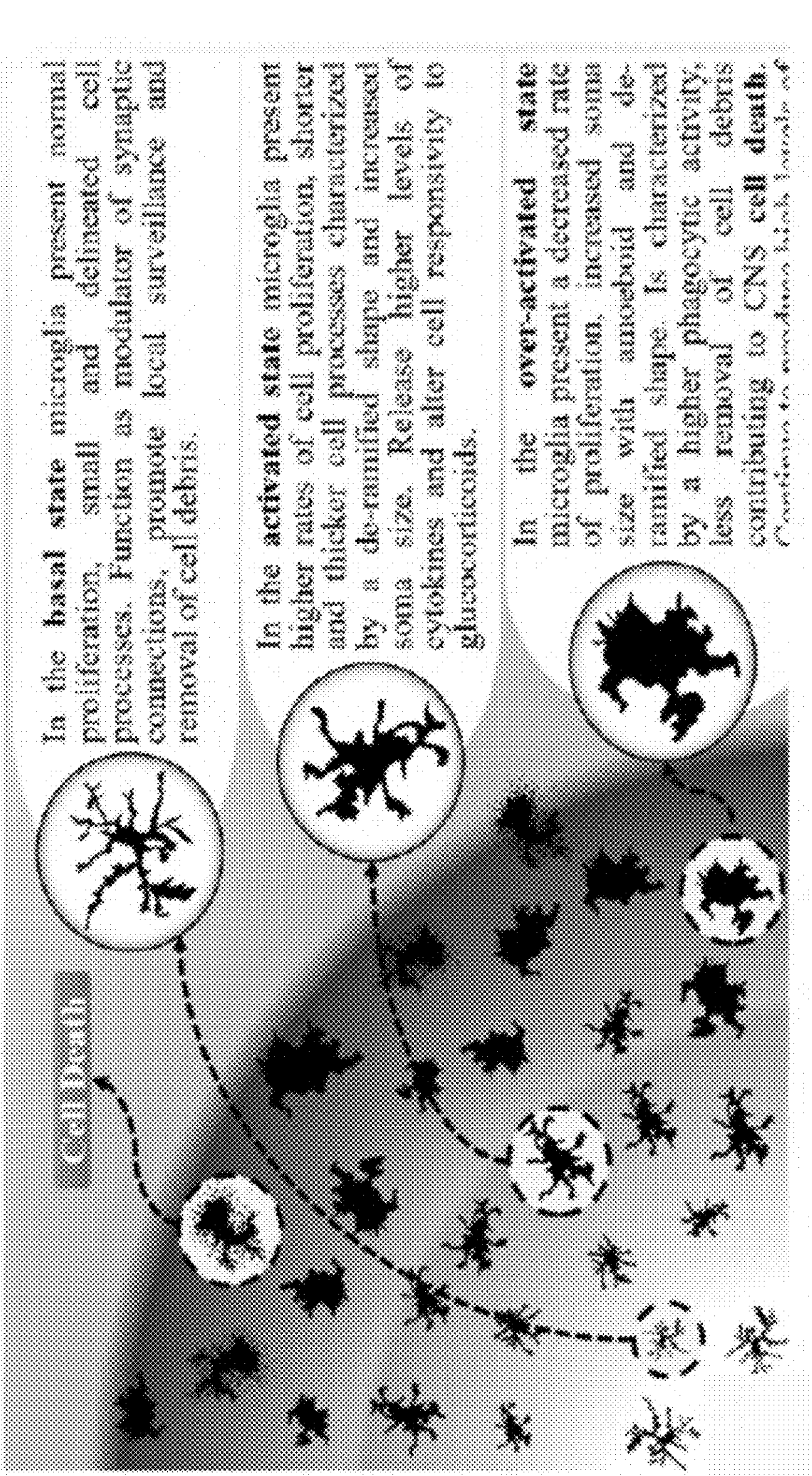
Figure 6L:
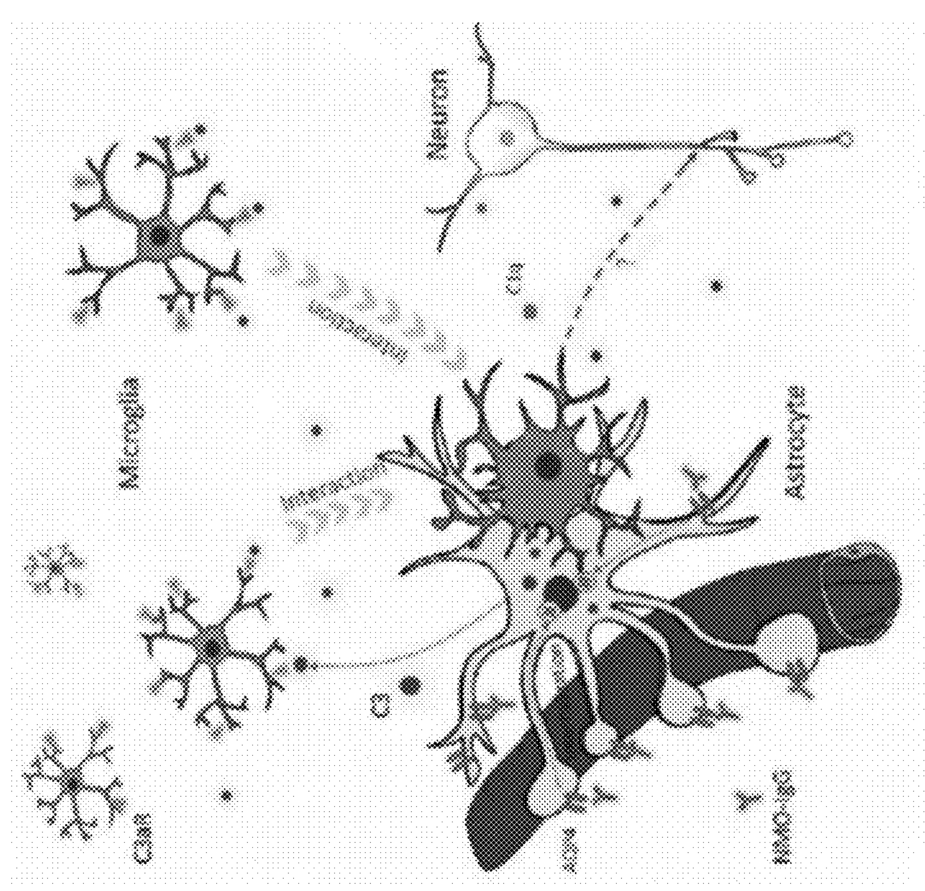
Figure 6M:
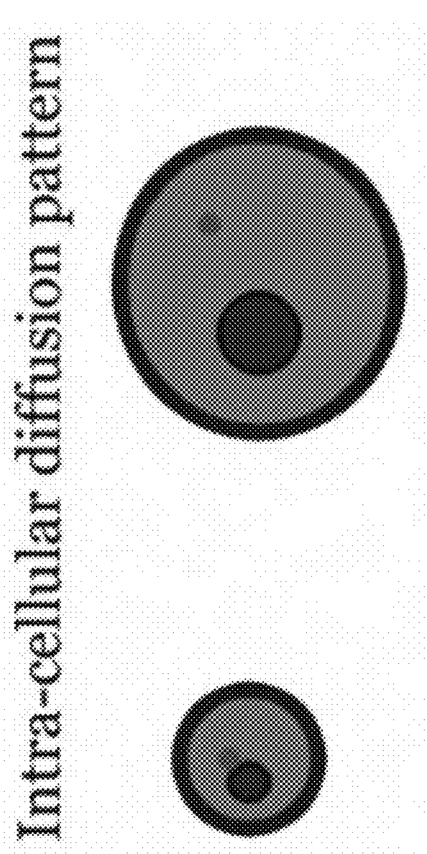
Figure 6N:
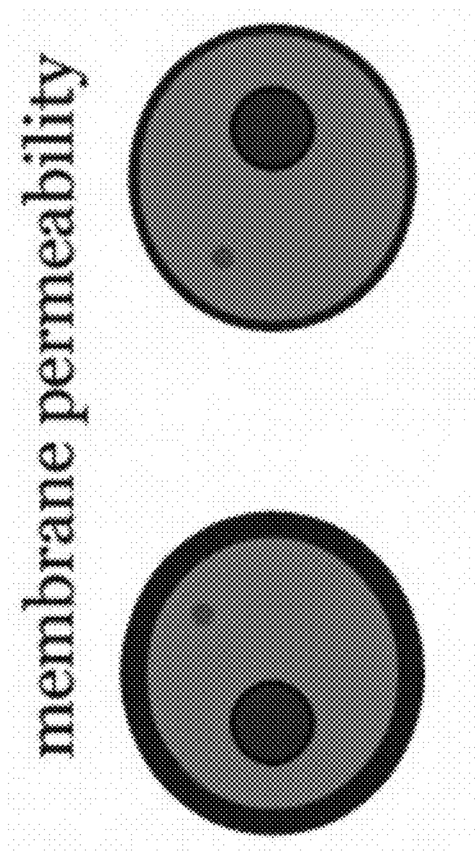
Figure 6O:
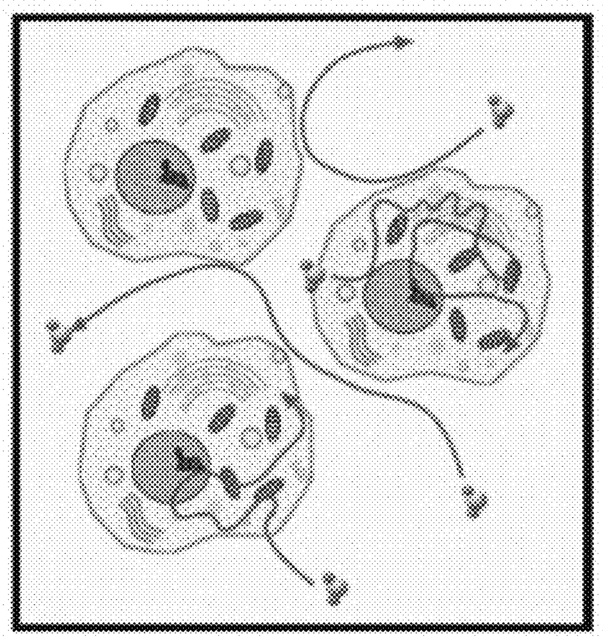

FIGS. 6A-6O depicts aspects of diffusion MRI in accordance with embodiments described herein. For example, FIG. 6A includes an illustration of the human immune system. For example, the typical human immune system includes innate immunity, or rapid response, and adaptive immunity, or slow response. FIG. 6B depicts the pathway for imaging the immune response. The measurement of inflammation, in some embodiments, may be achieved through imaging by detecting certain characteristic features associated with immune responses. FIG. 6C depicts molecular imaging. In some embodiments, a translocator protein may be upregulated during neuroinflammation in neurodegeneration. FIG. 6D depicts a water molecule being used as a tracer. As shown in FIG. 6E, in one embodiment, water walking, or a random walk, without the need for any type of radiotracer binding. FIG. 6E also shows an example embodiment of characterization of cerebral white matter properties using quantitative magnetic resonance imaging stains. FIGS. 6F and 6G illustrate a real-life example, a robotic vacuum (e.g., a Roomba®). For example, similar to a robotic vacuum, a restricted walking trajectory may be used to probe structure features. In FIGS. 6H and 6I, a measurement may be performed by dMRI to probe a microstructure. In FIG. 6H, inference of a human brain fiber bundle atlas from high angular resolution diffusion imaging is shown. Microstructural features may be detected that may be associated with an immune response.

In FIG. 6J, an example microstructural feature (e.g., Microglia in Alzheimer's disease) is depicted, immune cell infiltration. In FIG. 6K, another example microstructural feature (e.g., Microglia Over-Activation) is depicted, microglial cell morphology changes during activation. In this example, different stages of Microglia Activation are depicted, wherein over-activation may contribute to stress, anxiety, and depressive-like behaviors. In FIG. 6L, another example microstructural feature is depicted, immune cell activation leading to BBB dysfunction. In this example, the AQP4 water channel on astrocytes may experience upregulation. In this example, astrocyte-microglia interaction drives evolving neuromyelitis optica lesions.

In some embodiments, inflammation-related microstructural features may be modeled by diffusion MRI models, as shown in FIGS. 6M-6O. FIG. 6M depicts an example intra-cellular diffusion pattern. FIG. 6N depicts an example pattern of membrane permeability. FIG. 6O is an example of a complicated microenvironment that one or more inflammation signals may be extracted from.

Figures 7A, 7B:
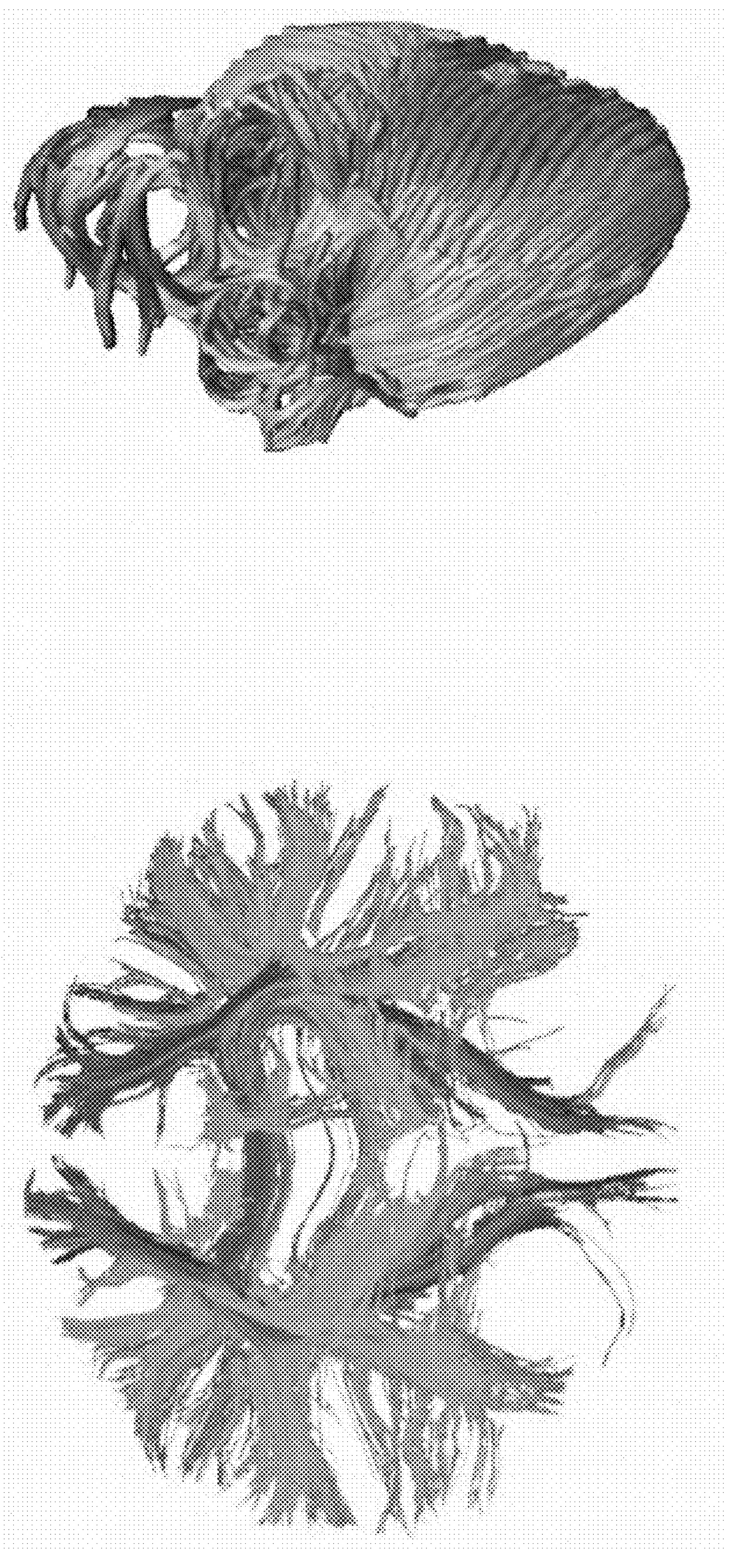
Figure 7C:
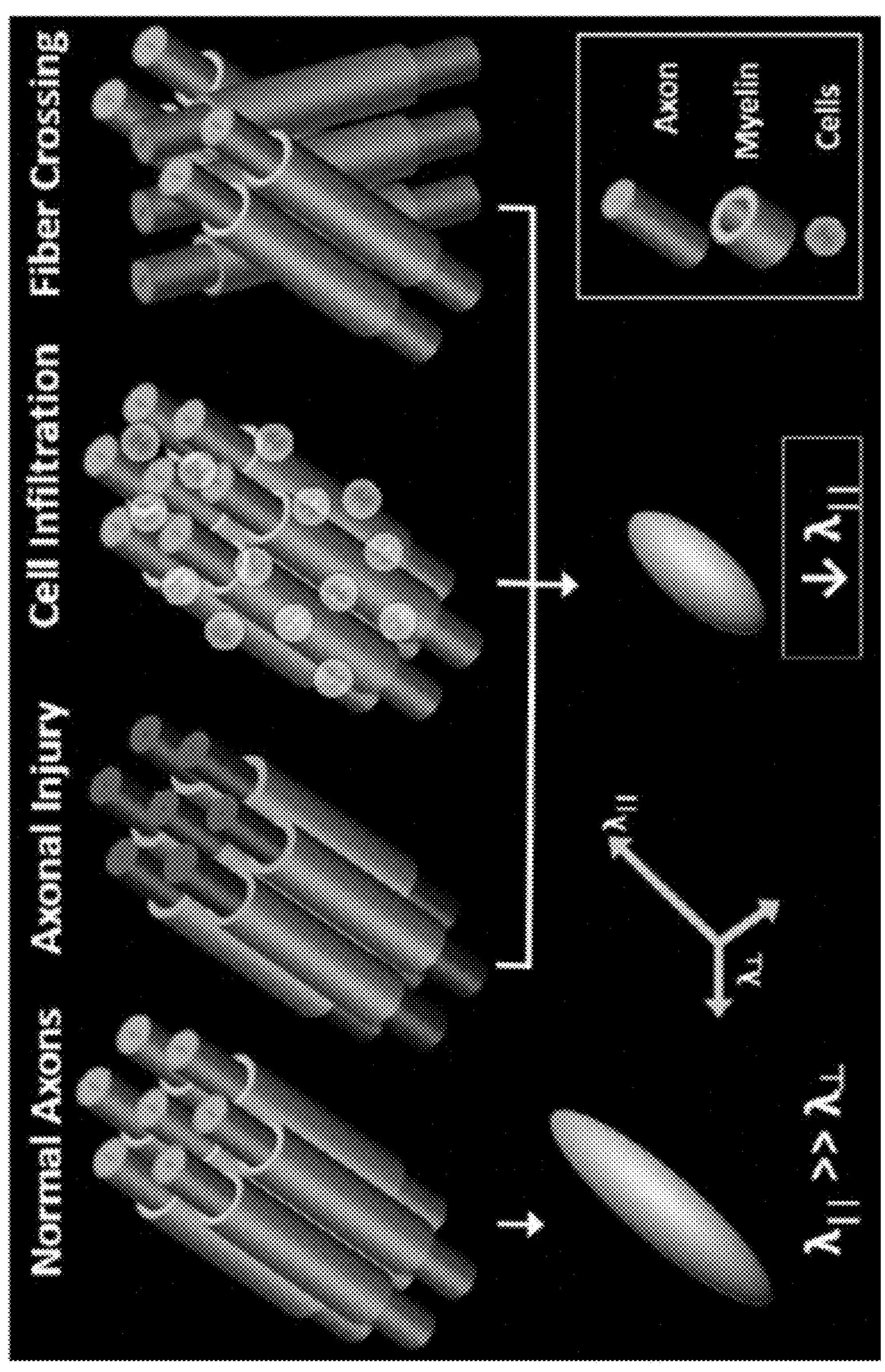
Figures 7D, 7E:
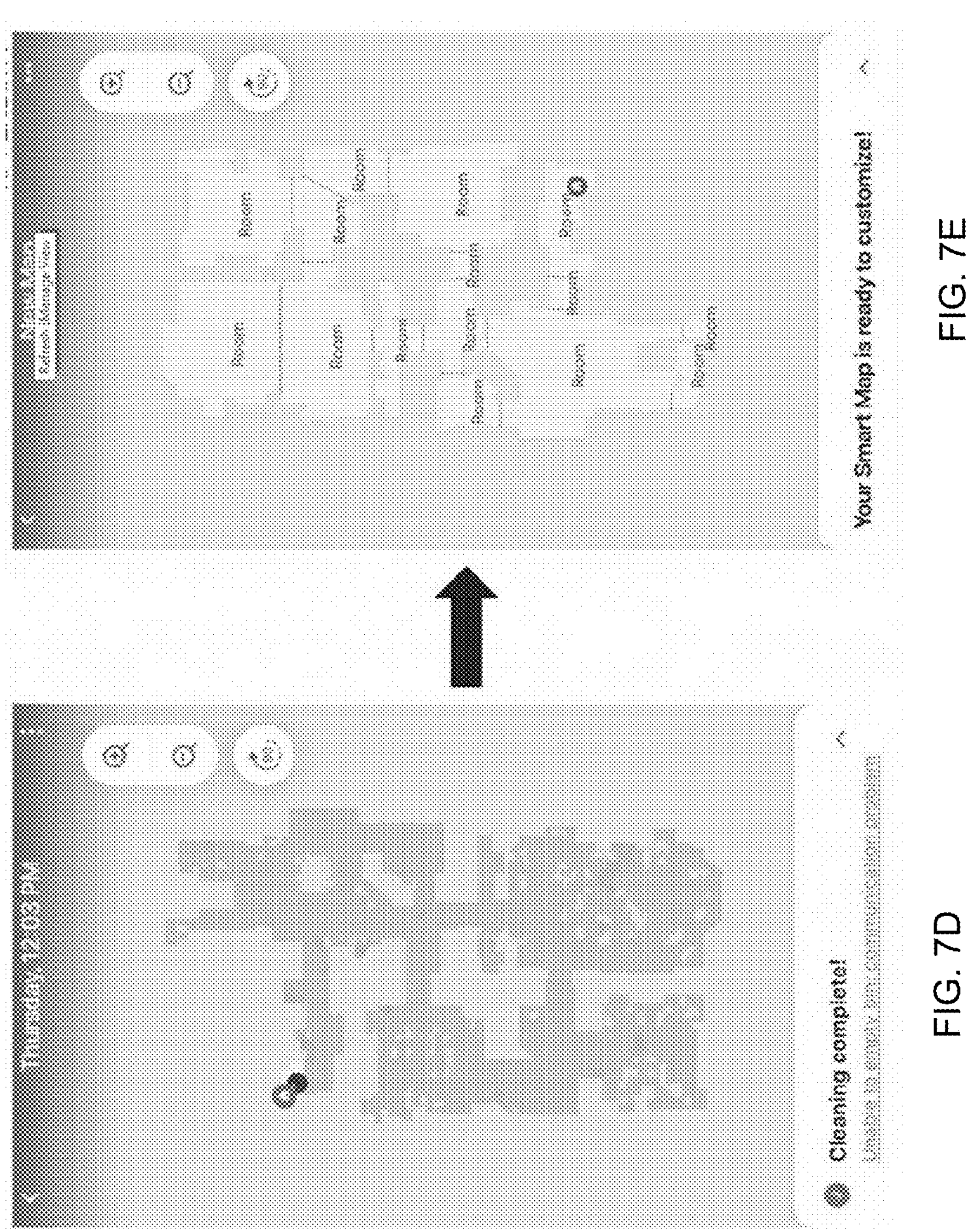
Figure 7F:
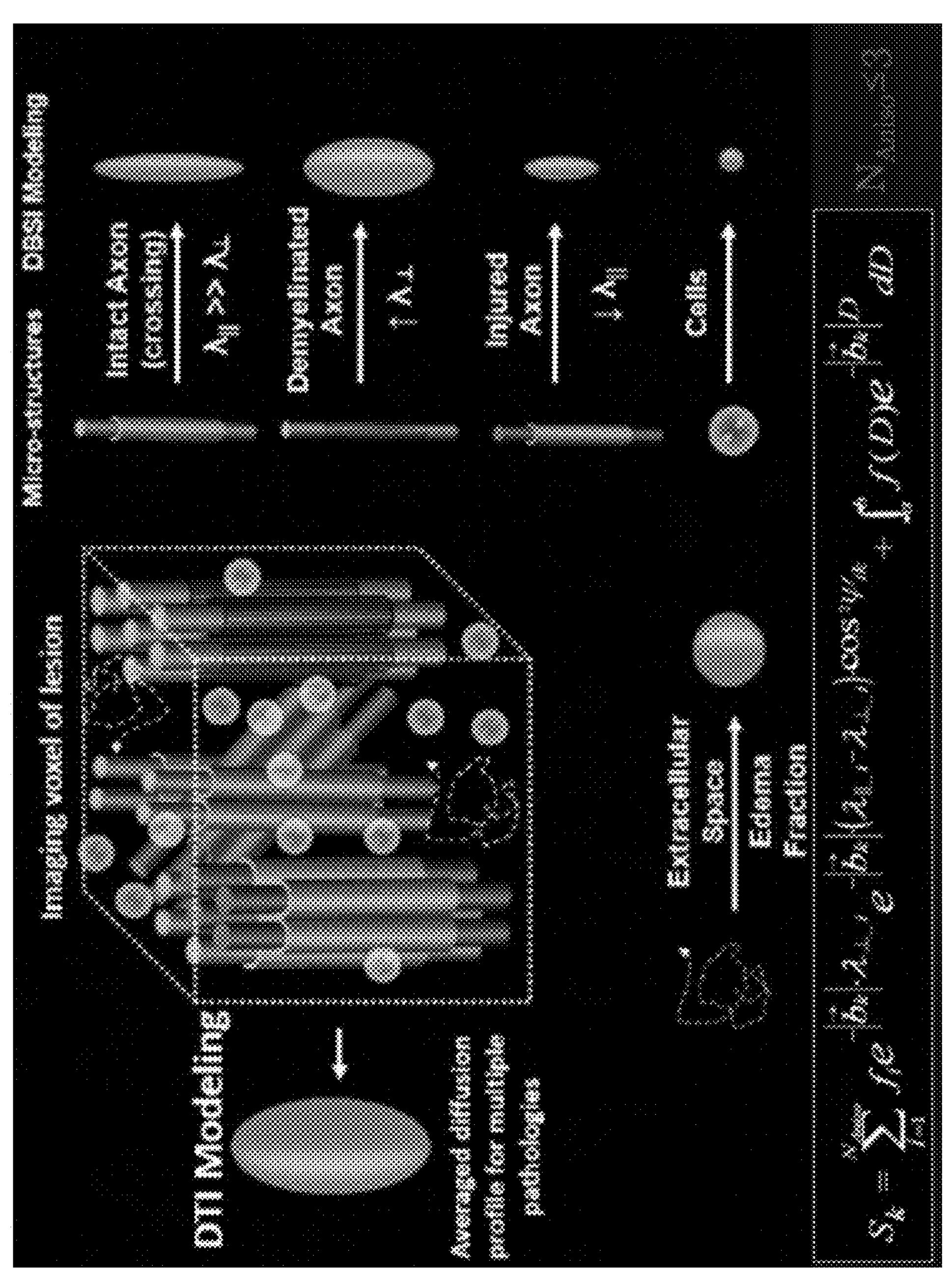

FIGS. 7A-7G depict different aspects of diffusion tensor imaging (DTI) to DBSI. One aspect is the separation of multiple intravoxel components. FIGS. 7A and 7B illustrate example DTI imaging of dominant anisotropic diffusion directions. FIG. 7C shows how DTI may not adequately resolve WM intravoxel heterogeneity. FIGS. 7D and 7E illustrate example customization of the real-life example of the robotic vacuum. FIG. 7F depicts DTI imaging where DBSI was developed to separate WM from isotropic diffusion. As shown in FIG. 7G, DBSI specifically images the isotropic diffusion in WM. Further development is needed. Prior examples have been used in different types of human diseases; increase specificity to image white matter injury, demyelination by separating anisotropic tissue components from the isotropic component; and provide an isotropic spectrum, which may reflect CNS pathologies. Limitations of the prior examples include modeling of coherent white matter where dispersion is less than 30 degrees does not account for WM dispersion; modeling of up to three crossing WM fibers, not for GM structures; and cannot directly be applied to other organs, such as a placenta for example.

Figure 8B:
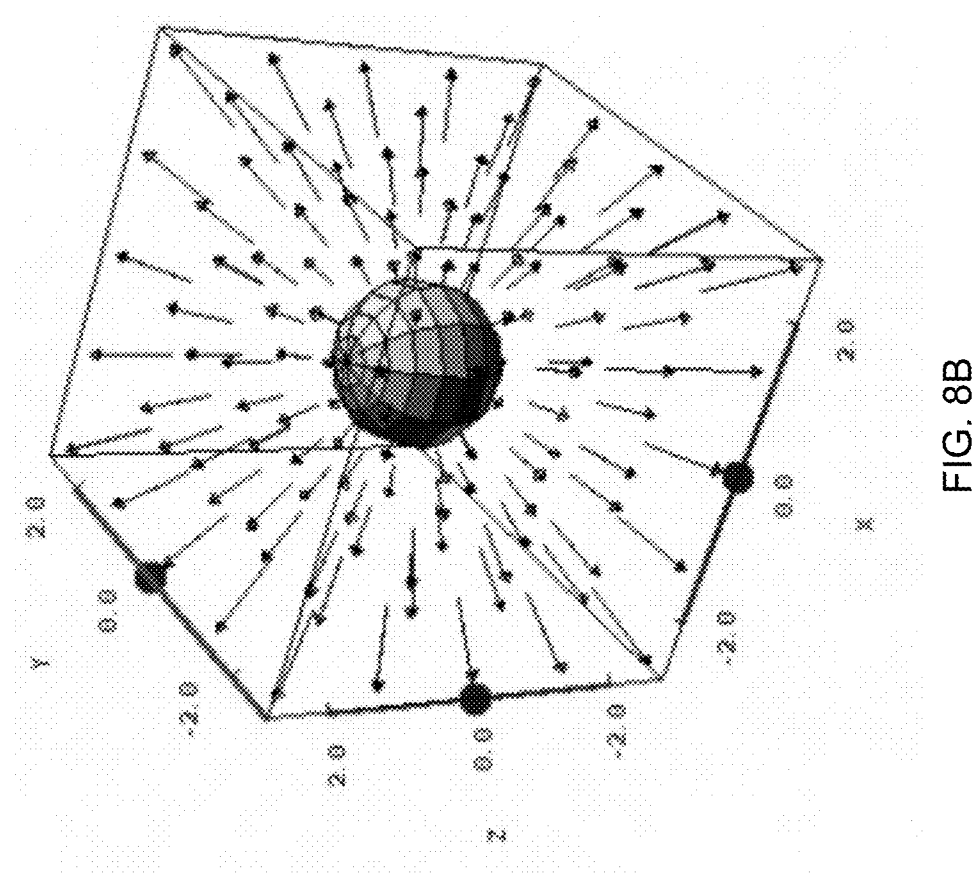
FIGS. 8A-8E illustrate aspects of DBSI to diffusion dictionary imaging (DDI) in accordance with at least one embodiment of the present disclosure.
Figure 8A:
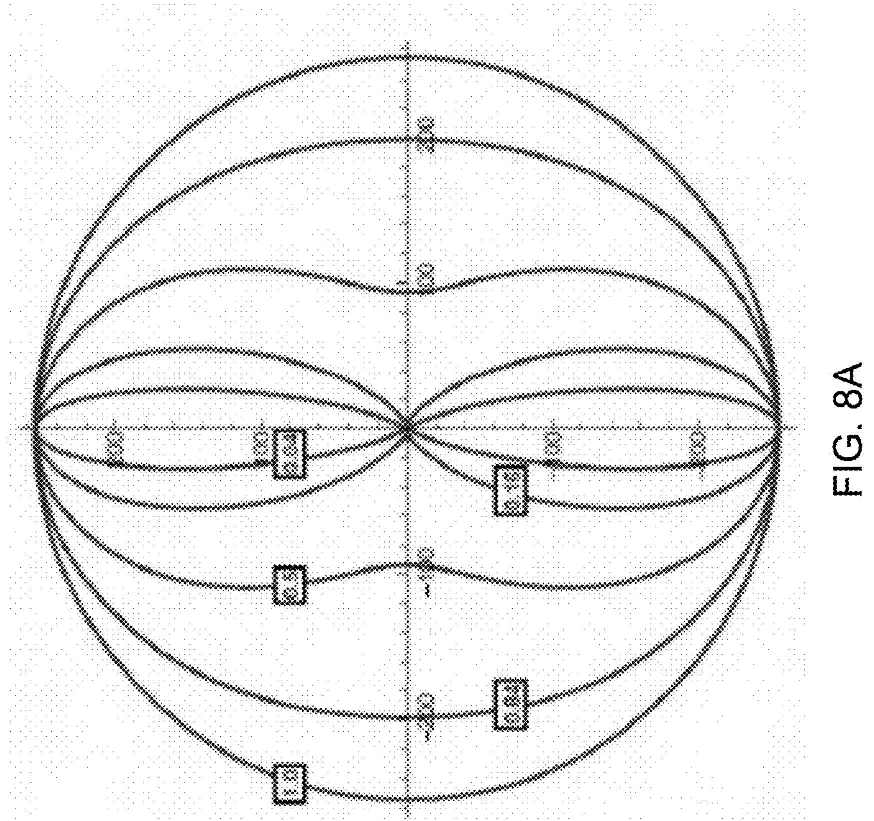
Figure 8C:
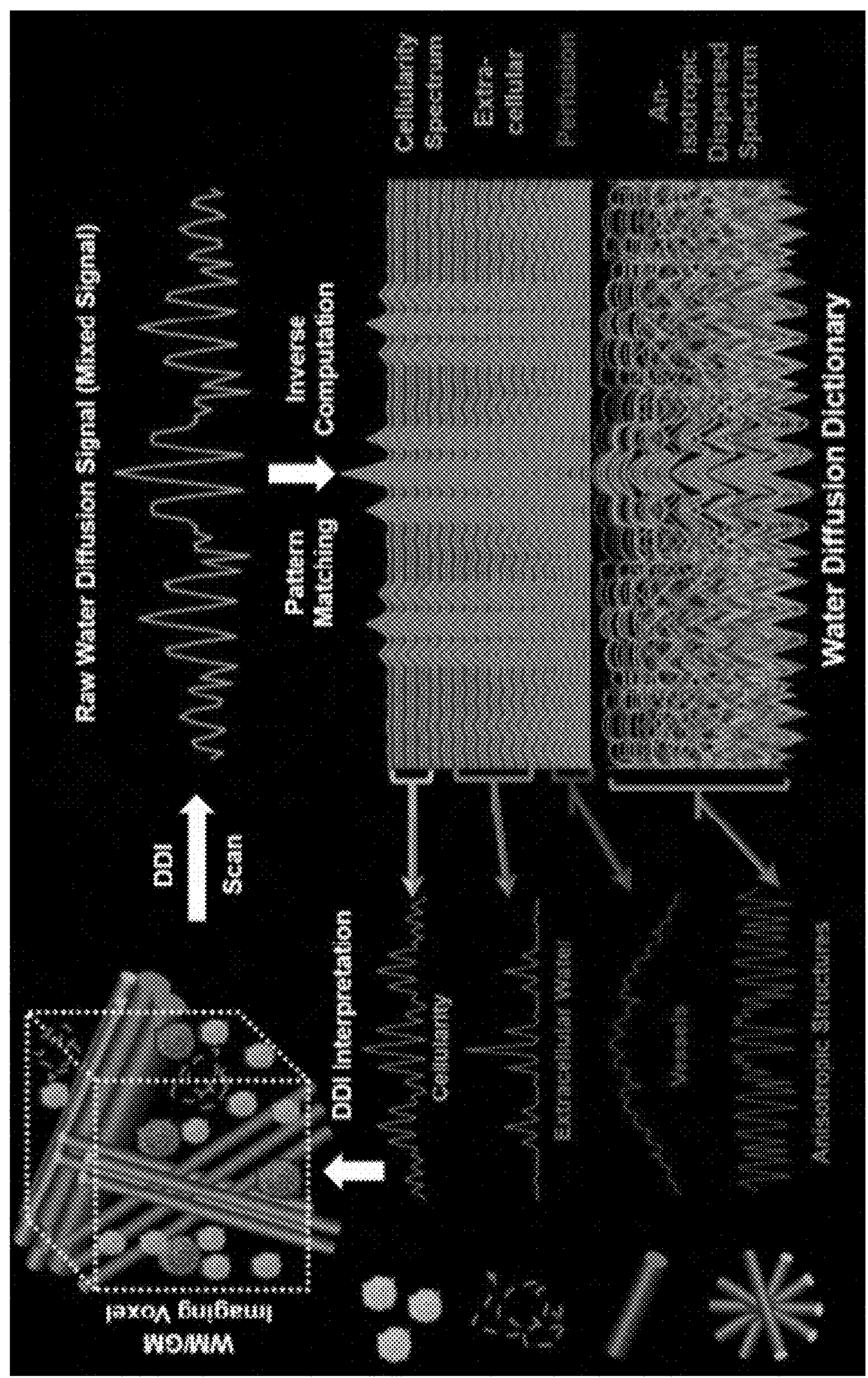

FIGS. 8A-8E depict different aspects of DBSI to diffusion dictionary imaging (DDI). FIGS. 8A and 8B illustrate the modeling of a GM microstructure using DDI. FIG. 8A illustrates a set of Watson distributions with the same mean orientation but a different orientation dispersion index. In this example, the Watson distribution is cylindrically symmetric showing a cross-sectional view through the symmetry axis which coincides with its mean orientation.

$$A = (1 - v_{iso})(v_{ic}A_{ic} + (1 - v_{ic})A_{ec}) + v_{iso}A_{iso},$$

$$S_{calculated}(q) = \int_{D \in \mathbb{D}} P(D)\exp(-tq^T Dq)dD$$

Figure 8D:
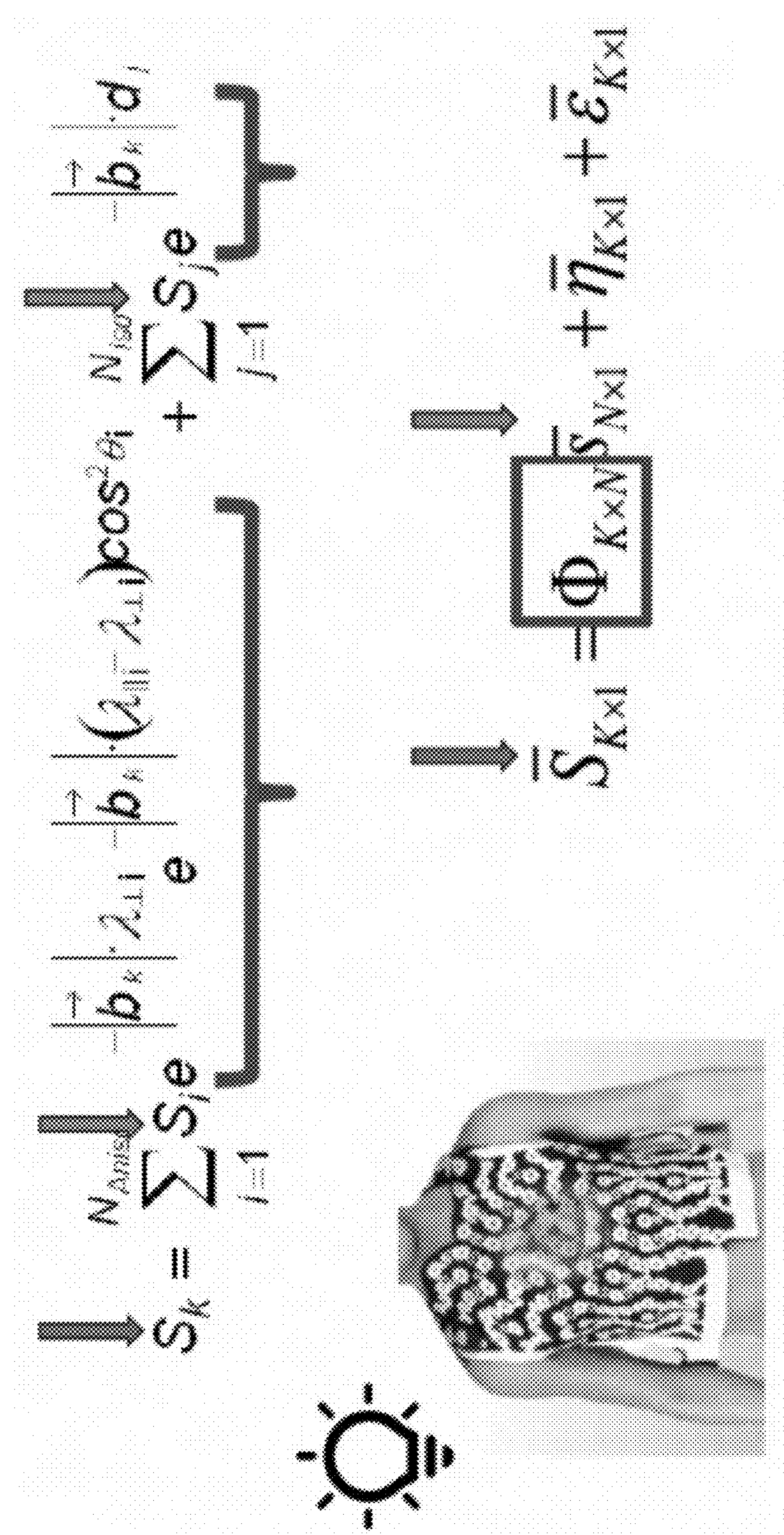
Figure 9A:
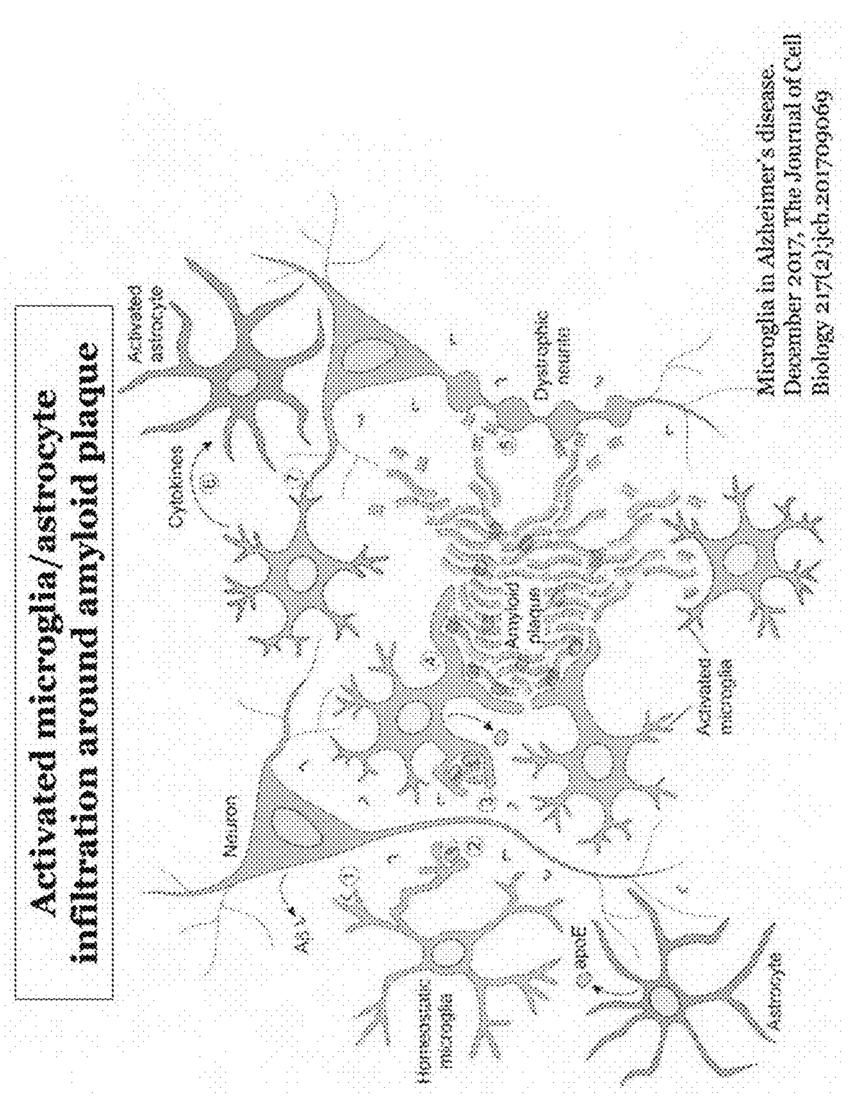
FIGS. 9A-9H illustrate aspects of DDI applications in accordance with at least one embodiment of the present disclosure.
Figure 9B:
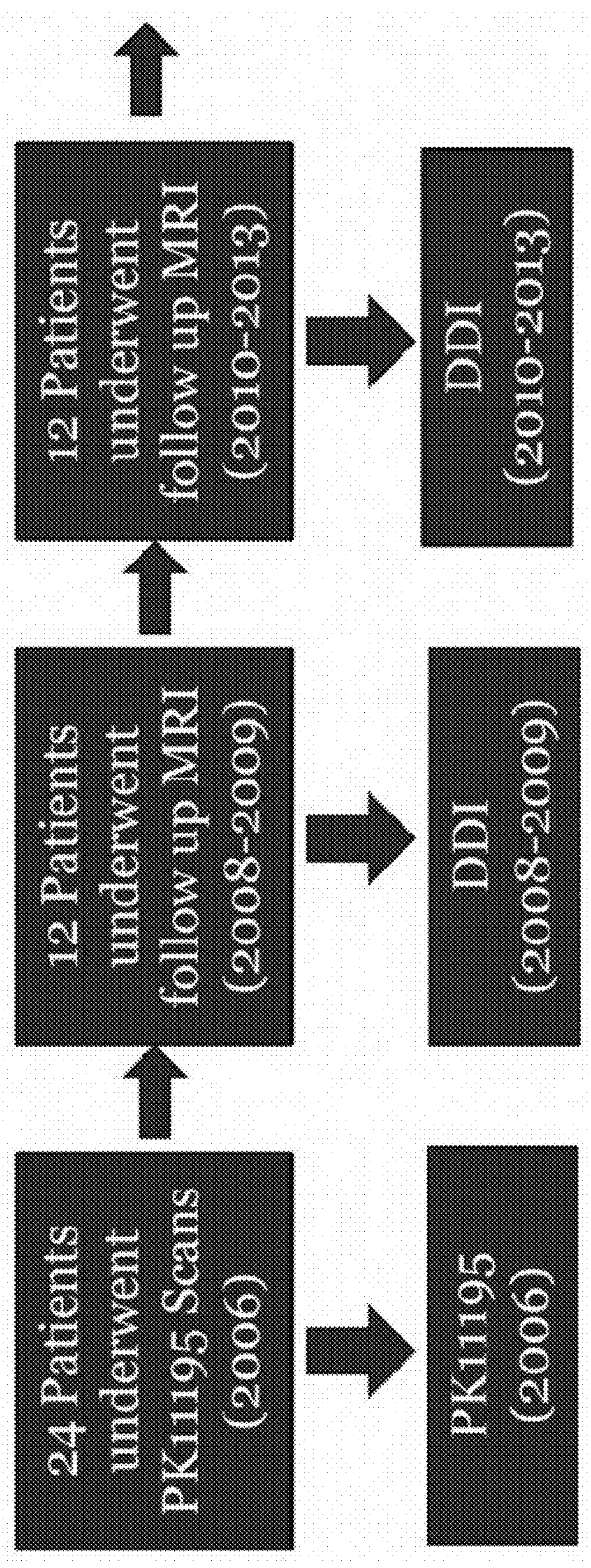
Figure 9C:
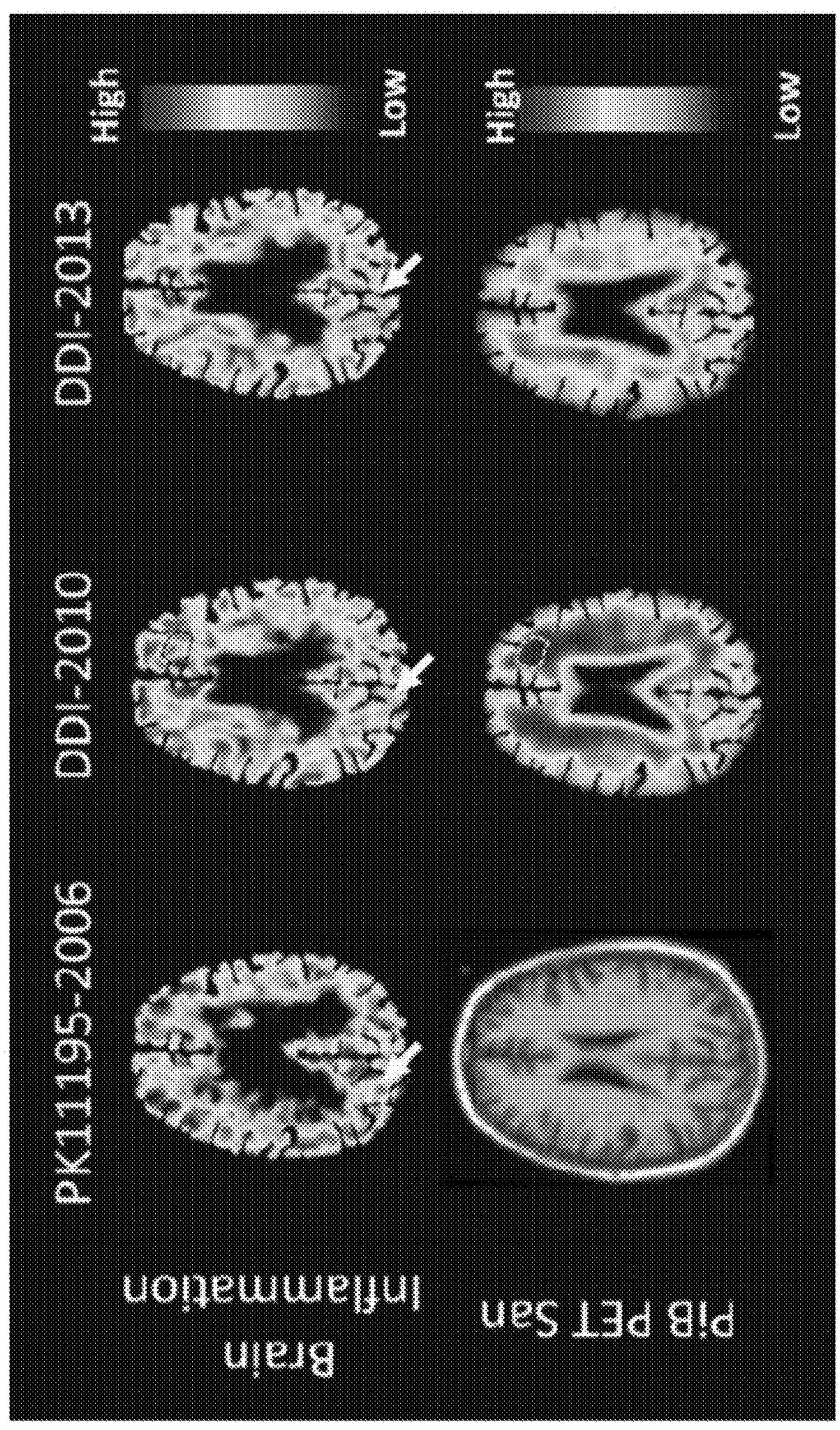

FIG. 9C depicts an exemplary DDI methodology for WM and GM. For example, a DDI scan may be performed to obtain a mixed signal or a raw water diffusion signal. The obtained signal may undergo a computational process, such as pattern matching or inverse computation. Additionally, the computational process may implement one or more algorithms using a water diffusion dictionary. A mathematical solution, as shown in FIG. 8D, may be used for a large number of free variables.

Figure 8E:
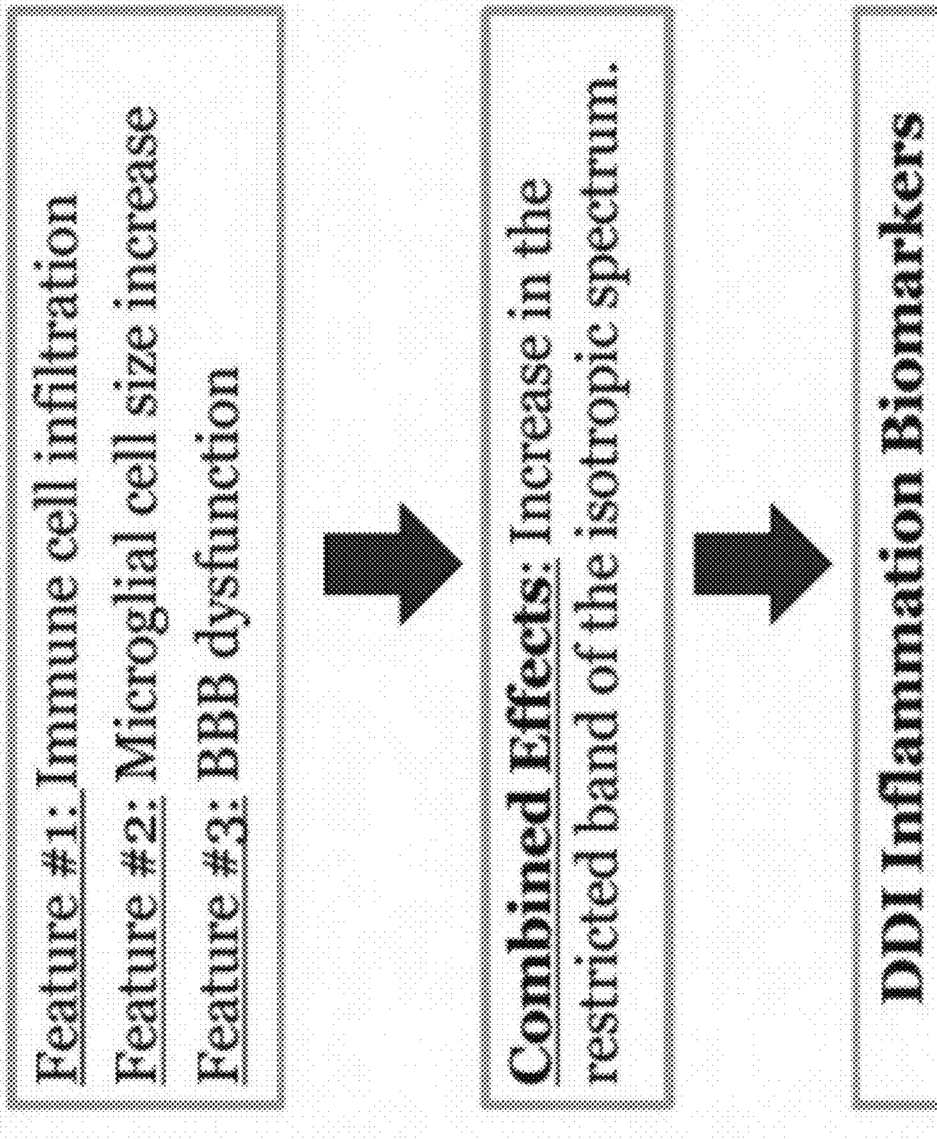

In some embodiments, shown in FIG. 8E, DDI may enable inflammation imaging in both white matter and gray matter. Three features may include immune cell infiltration, microglial cell size increase, and BBB dysfunction. The combined effects may include an increase in the restricted band of the isotropic spectrum. Additionally, DDI inflammation biomarkers may be identified.

Figure 9D:
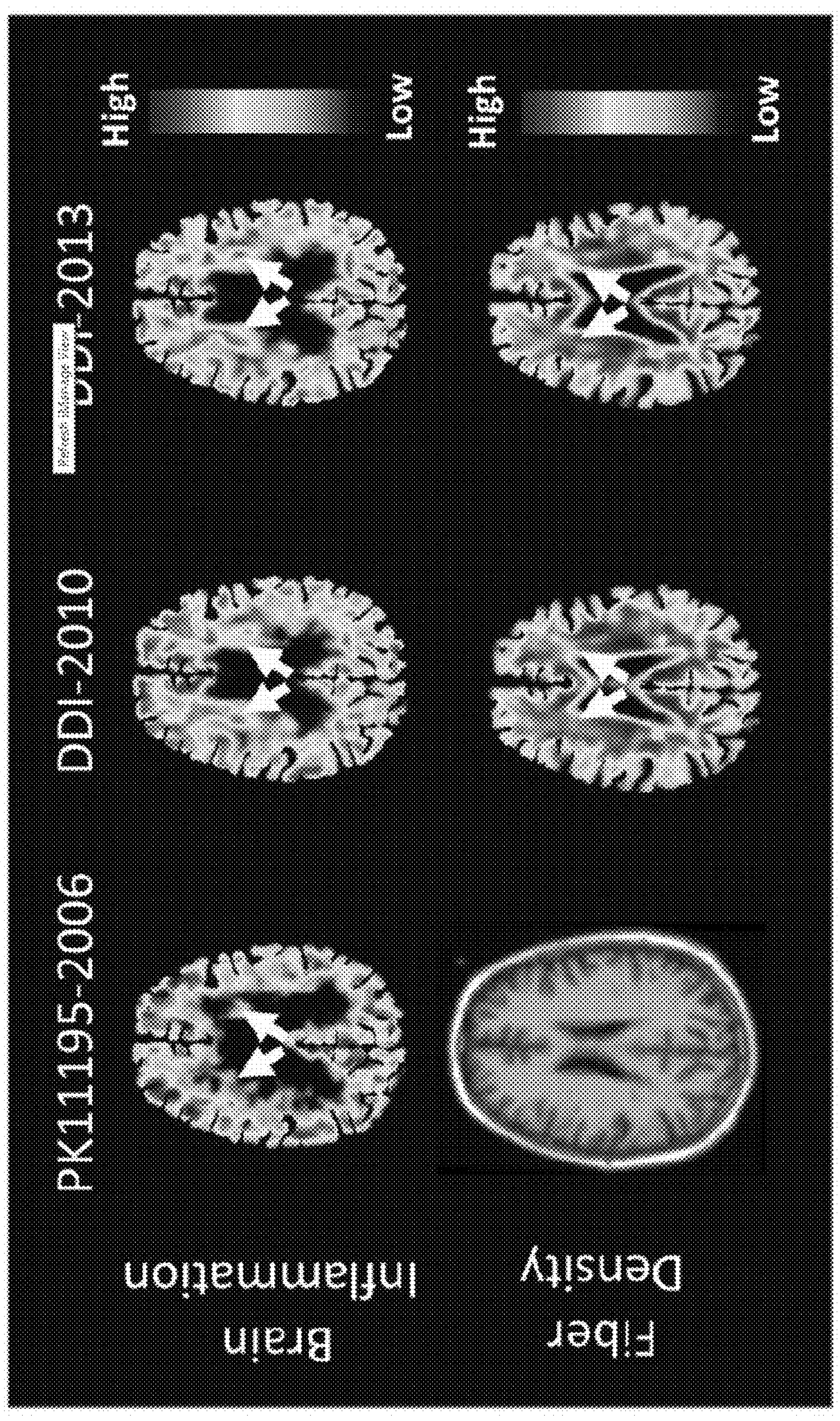
Figure 9E:
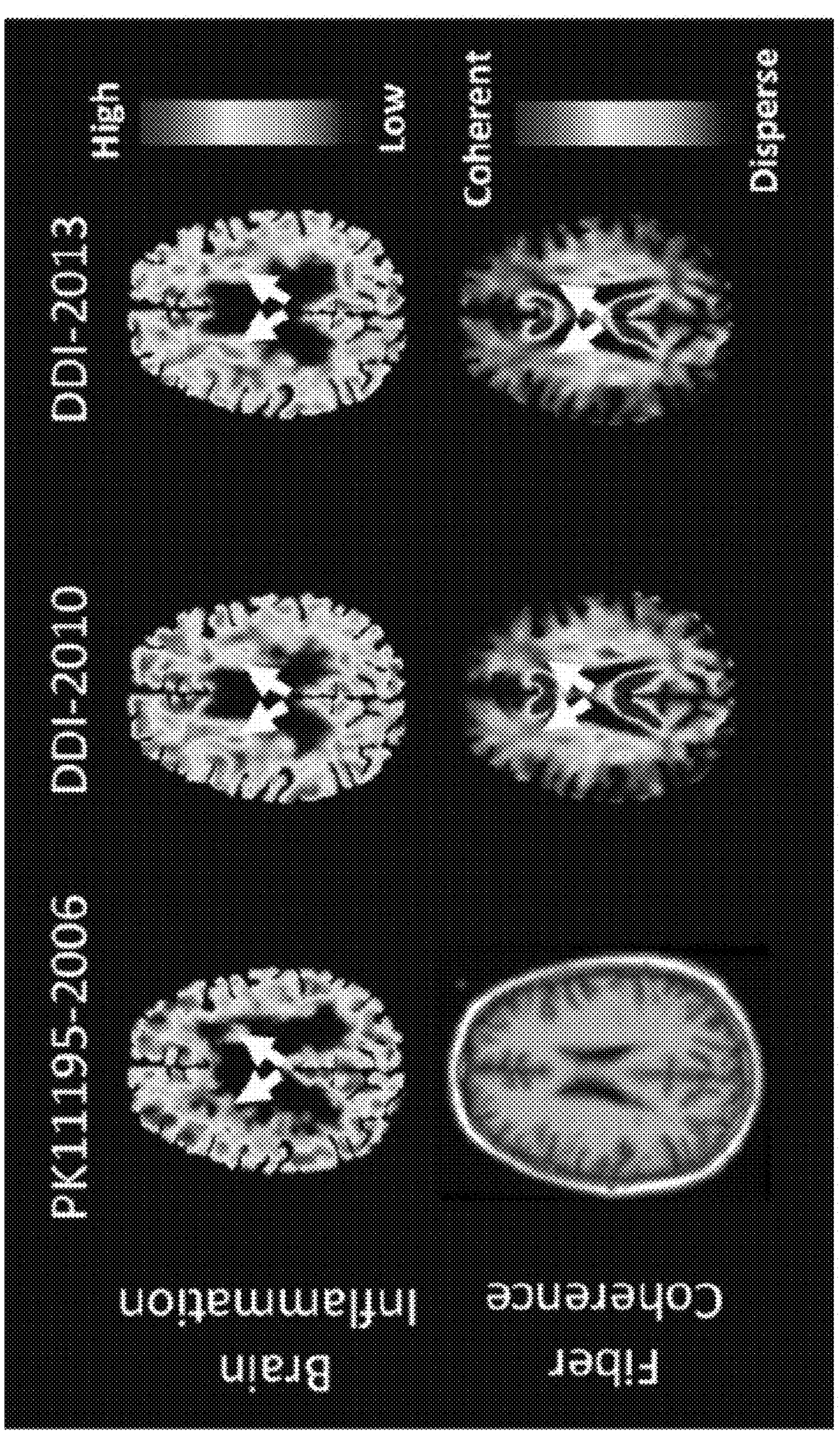
Figure 9F:
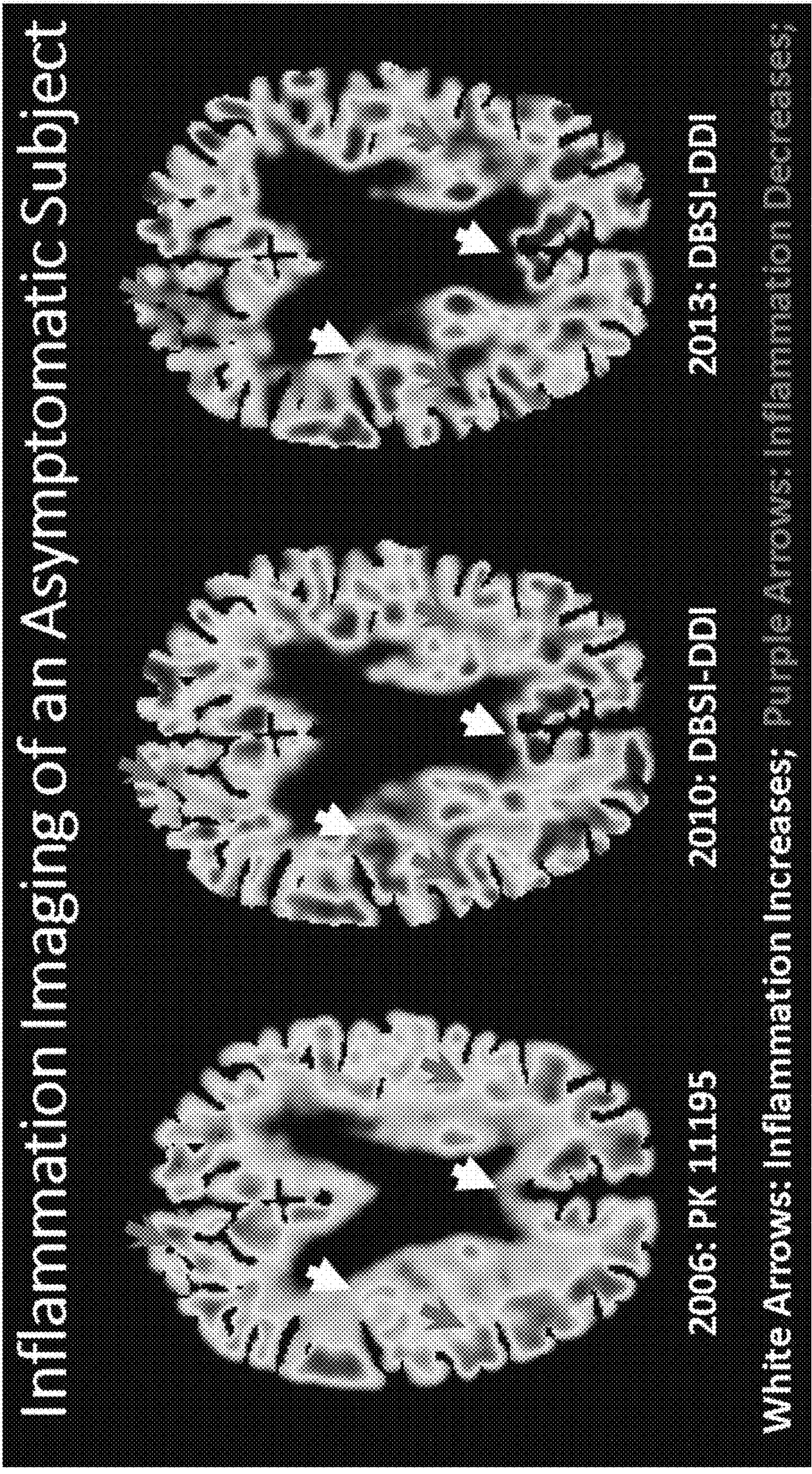
Figure 9G:
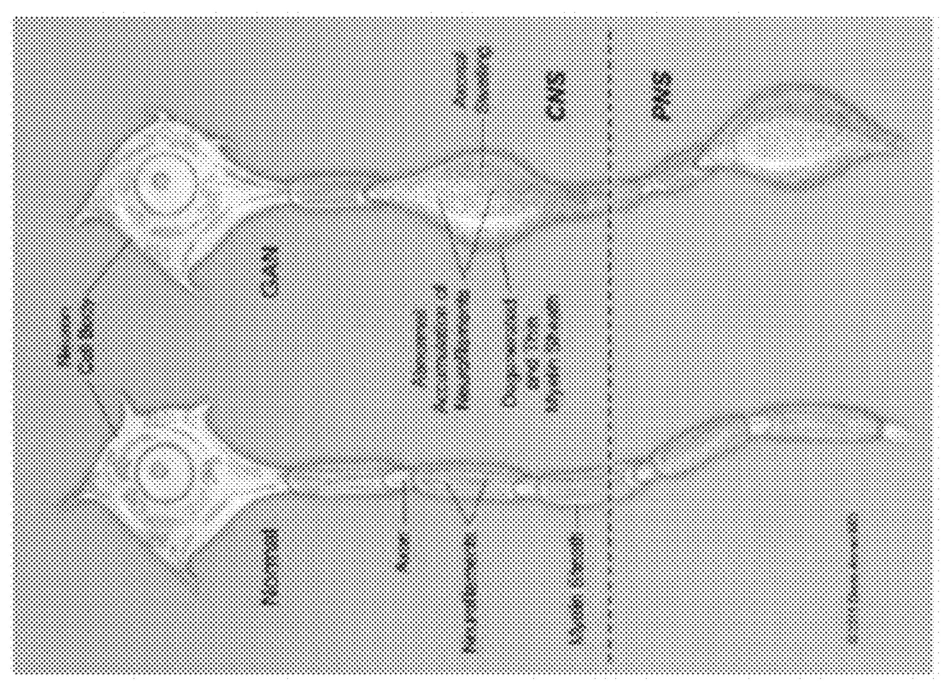
Figure 9H:
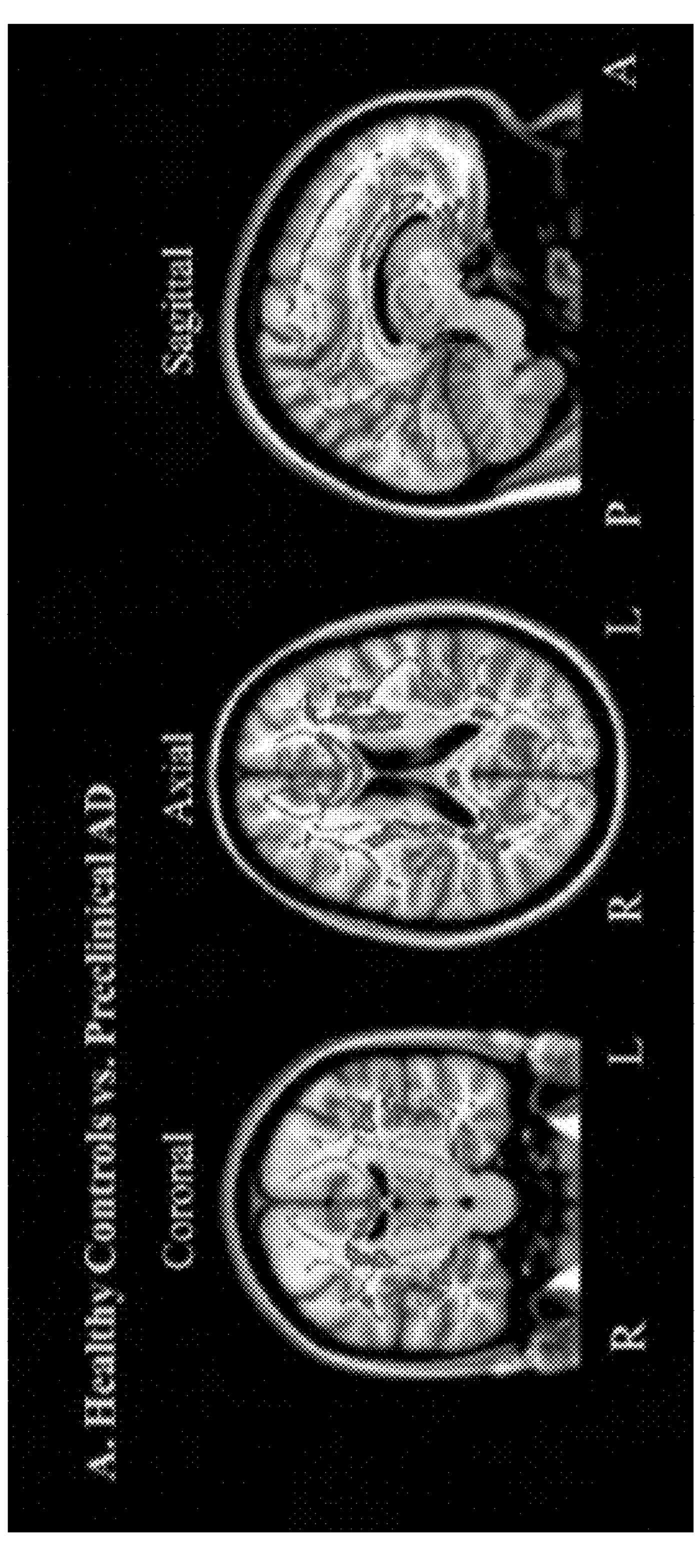

FIGS. 9A-9H illustrate example DDI clinical applications to provide a better understanding of the embodiments disclosed herein. Two examples include the human brain and placenta. FIG. 9A depicts neuroinflammation in AD. For example, an activated microgliad/astrocyte infiltration around amyloid plaque. FIG. 9B illustrates an example study, the PK11195 study in 24 preclinical AD patients. FIG. 9C illustrates a patient that remained in a cognitive normal state. FIG. 9D illustrates a patient that may have experienced WM inflammation caused by WM degeneration. FIG. 9E illustrates a scan of a patient with increased WM dispersion. FIG. 9F illustrates exemplary inflammation imaging of an asymptomatic subject. FIG. 9G illustrates exemplary axonal swelling that may appear in the early phase of AD pathology. Speculation is that axonal swelling may lead to WM inflammation. DBSI may be detected with WM neuroinflammation in preclinical AD where N=175. Stage 0 (n=144) and Stage 1 (n=31). Neuroinflammation associated with microglial activation may be present with Aβ deposition but precedes detectable CSF tau pathology in the cohort. FIG. 9H illustrates exemplary healthy controls vs. preclinical AD.

Figure 10A:
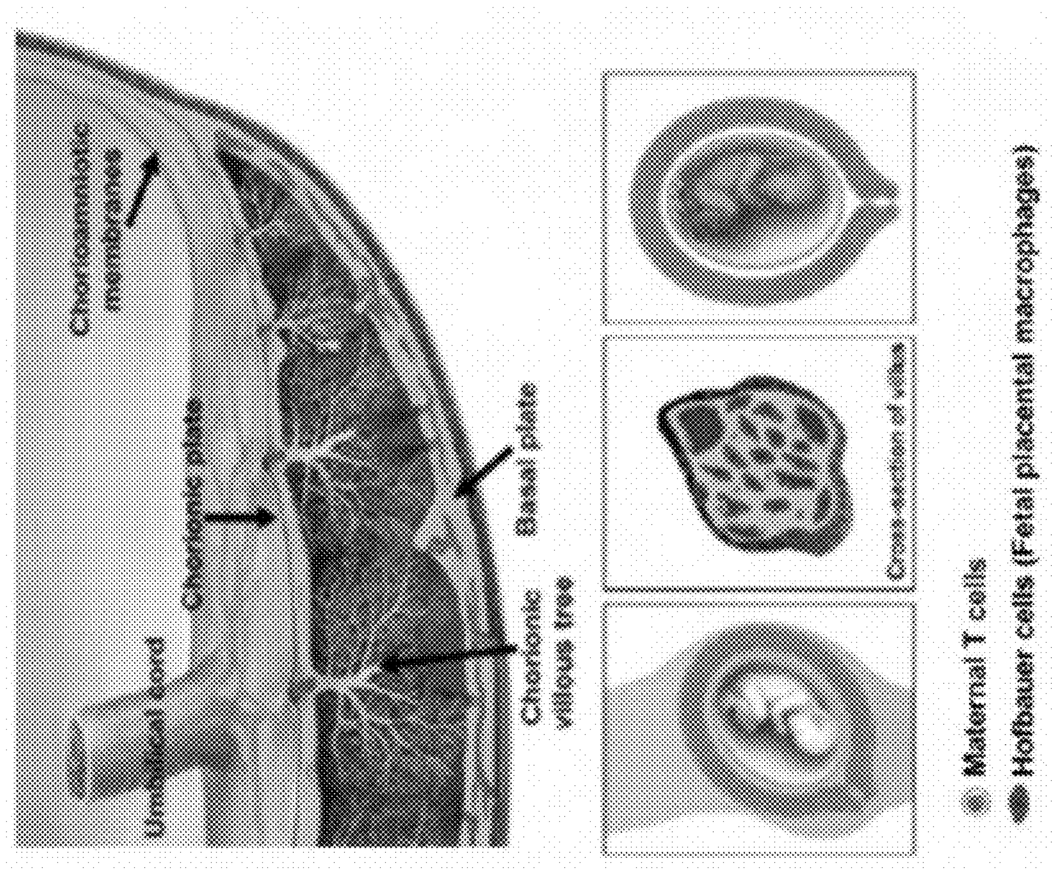
Figure 10D:
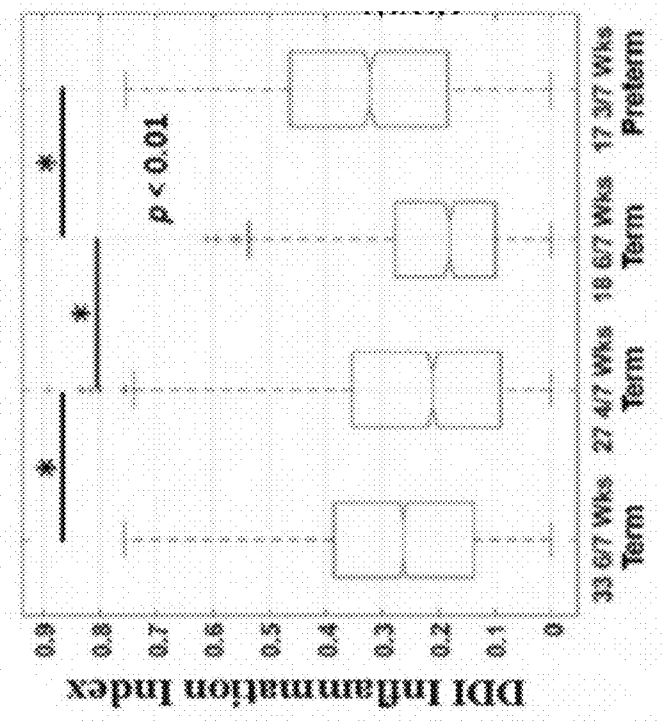
Figure 10C:
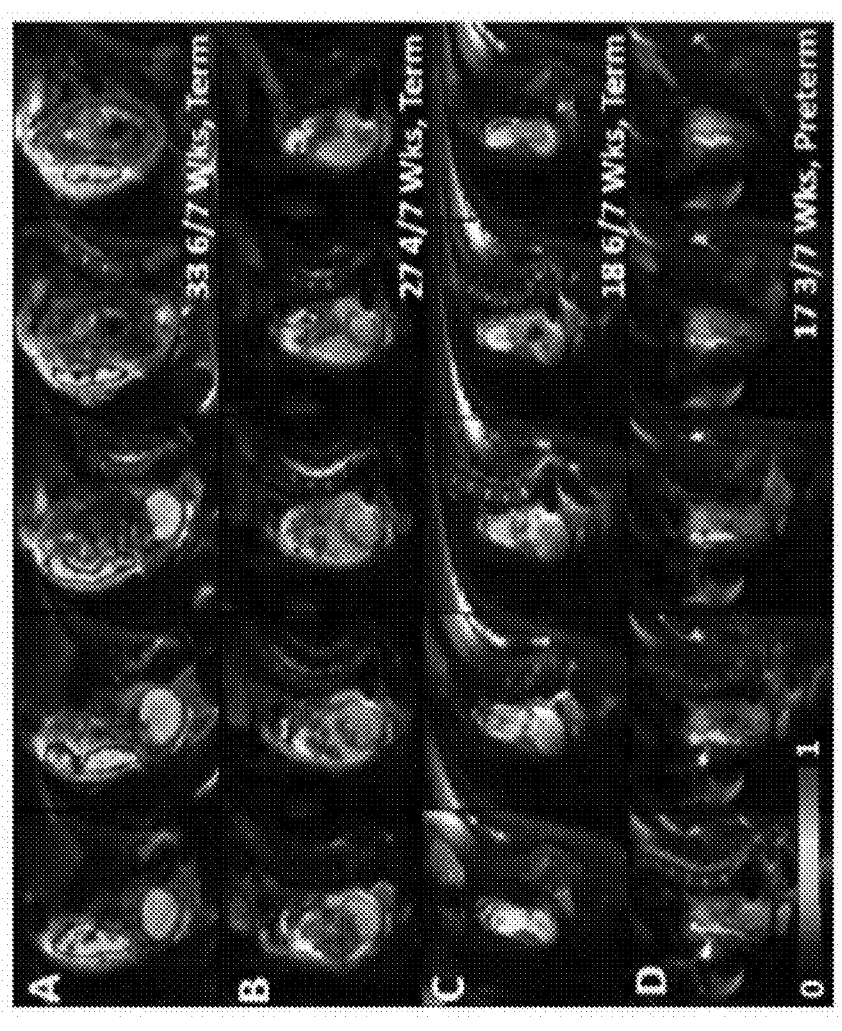
Figure 10E:
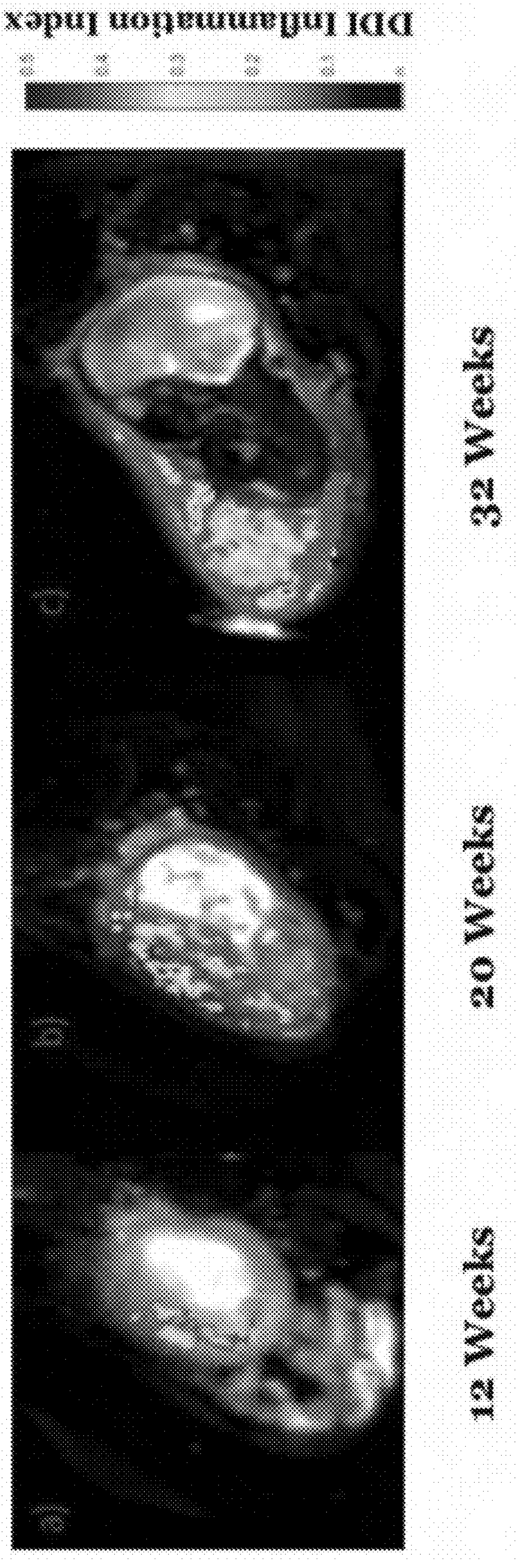
Figure 10F:
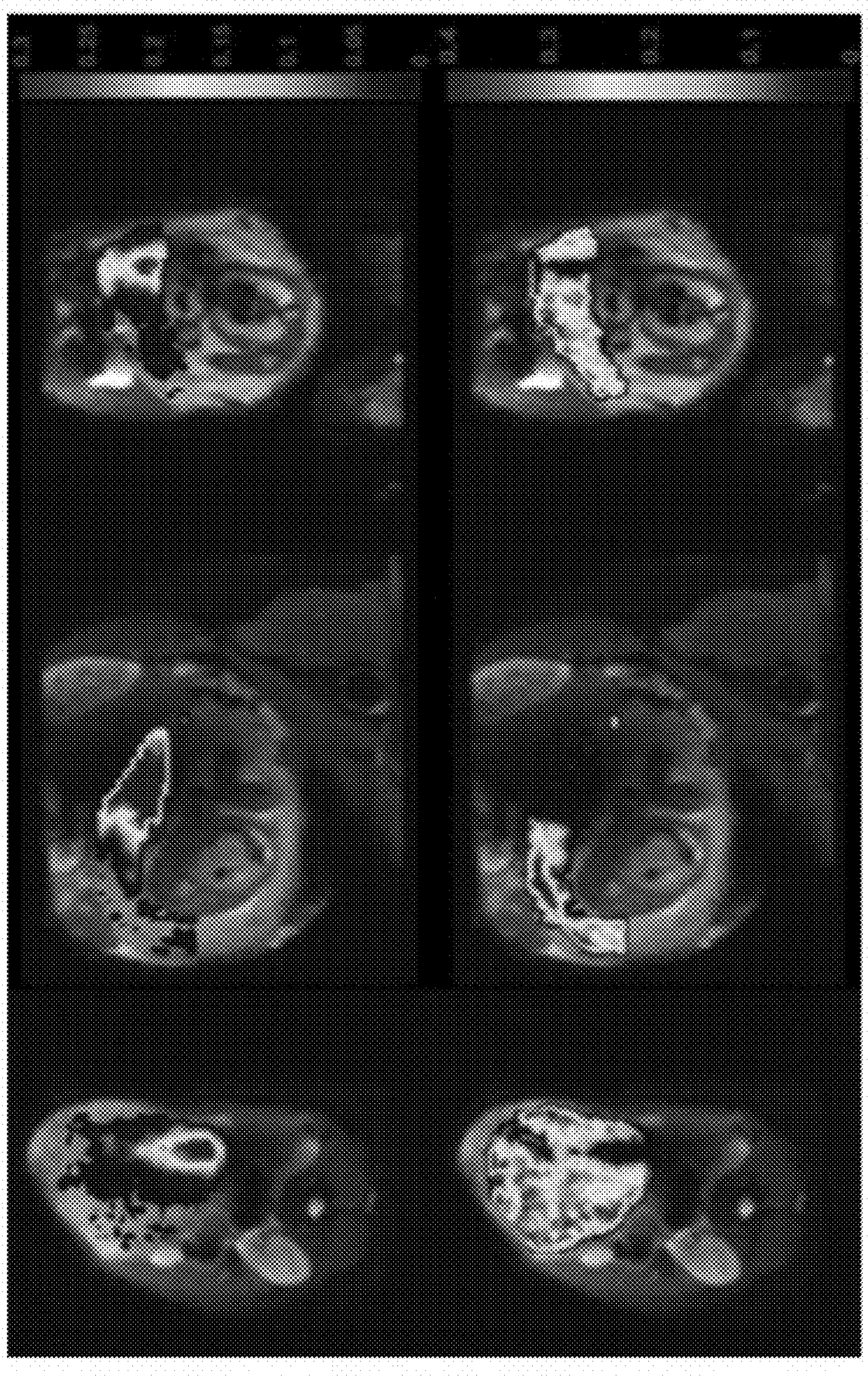

FIGS. 10A-10L depict examples of DDI application in a human placenta. FIG. 10A illustrates an example human placenta including an umbilical cord, a chorionic plate, chorioamniotic membranes, a chorionic villous tree, and a basal plate. Two aspects of the immunologic nature of Villous Inflammation include 1) circulating maternal T cells entering the intervillous space that can infiltrate the villus, and 2) after maternal T-cell infiltration, Hofbauer cells, or fetal placental macrophages, may be activated. In summary, infiltration T cell and activated macrophage in placental inflammation. FIG. 10B illustrates an example clinical test of longitudinal DDI imaging of placenta immune response during human pregnancy. The goal of the example test was to employ DDI to detect immune signatures of healthy pregnancies that go to term and reveal immune responses characteristic of preterm birth risk and treatment failure. FIGS. 10C and 10D illustrate an example where DDI may detect placental immune differences. For example, in FIG. 10D, a DDI inflammation index illustrates increased placental inflammatory measures in early pregnancy from a patient who delivered preterm. In some embodiments, and as shown in FIG. 10E, DDI may enable safe longitudinal inflammation imaging of a placenta during human pregnancy. FIG. 10F illustrates multiparametric imaging of human placental infarction including a perfusion index and an inflammation index at 32 weeks. In this example, pathology studies suggested that the patient had local placental infarction and inflammation.

Figures 10G, 10H:
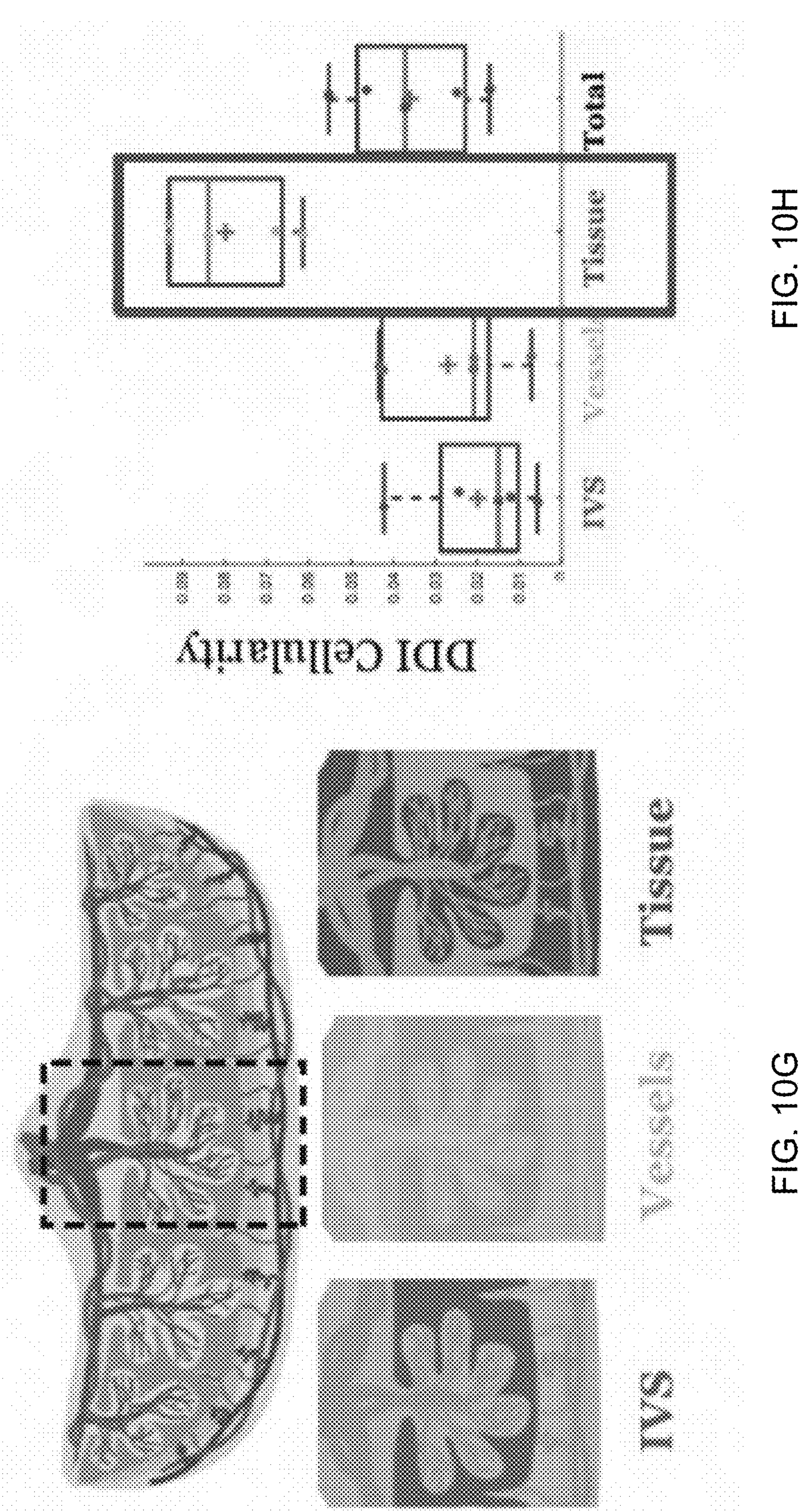
Figures 10I, 10J, 10K, 10L:
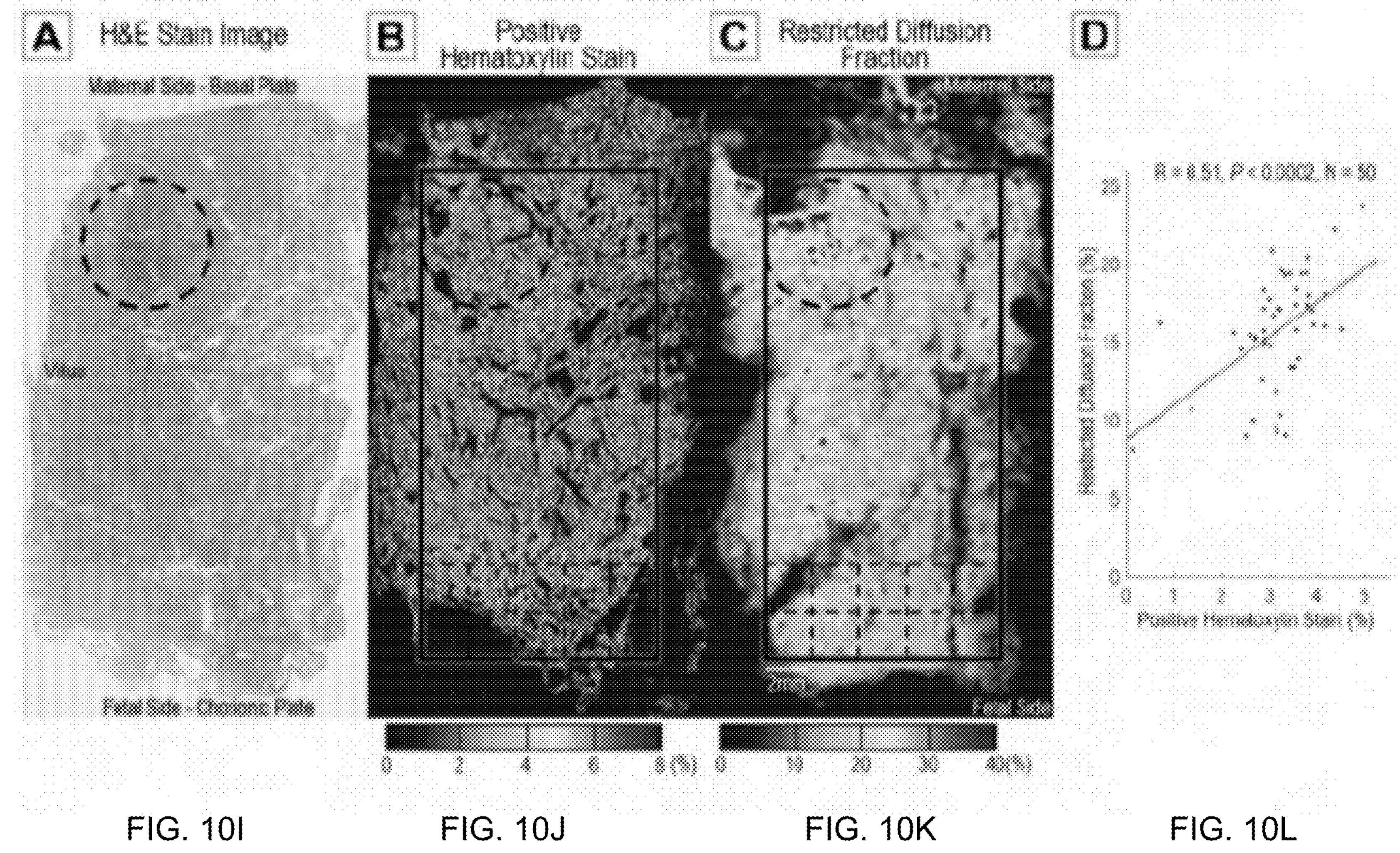

In some embodiments, and as depicted by FIGS. 10G and 10H, DDI imaging may provide automatic segmentation for better villous tree inflammation imaging of IVS, vessels, and tissue. Further examples are shown in FIG. 10I with respect to quantitative placental histology in a human including an H&E stain image, a positive hematoxylin stain, and a restricted diffusion fraction.

Figure 11A:
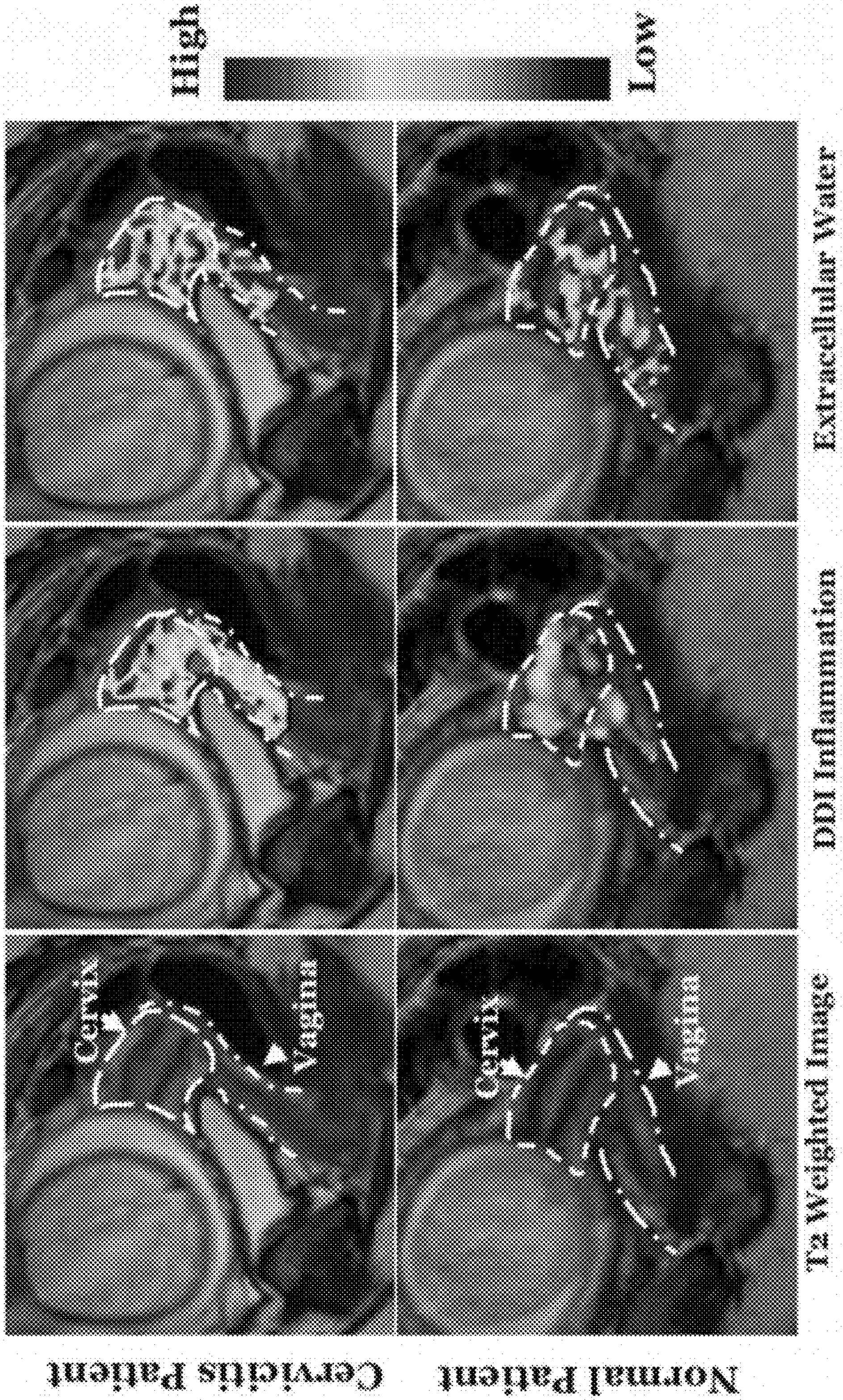
FIGS. 11A-11C illustrate aspects of DDI application in the human cervix/uterus in accordance with at least one embodiment of the present disclosure.
Figure 11B:
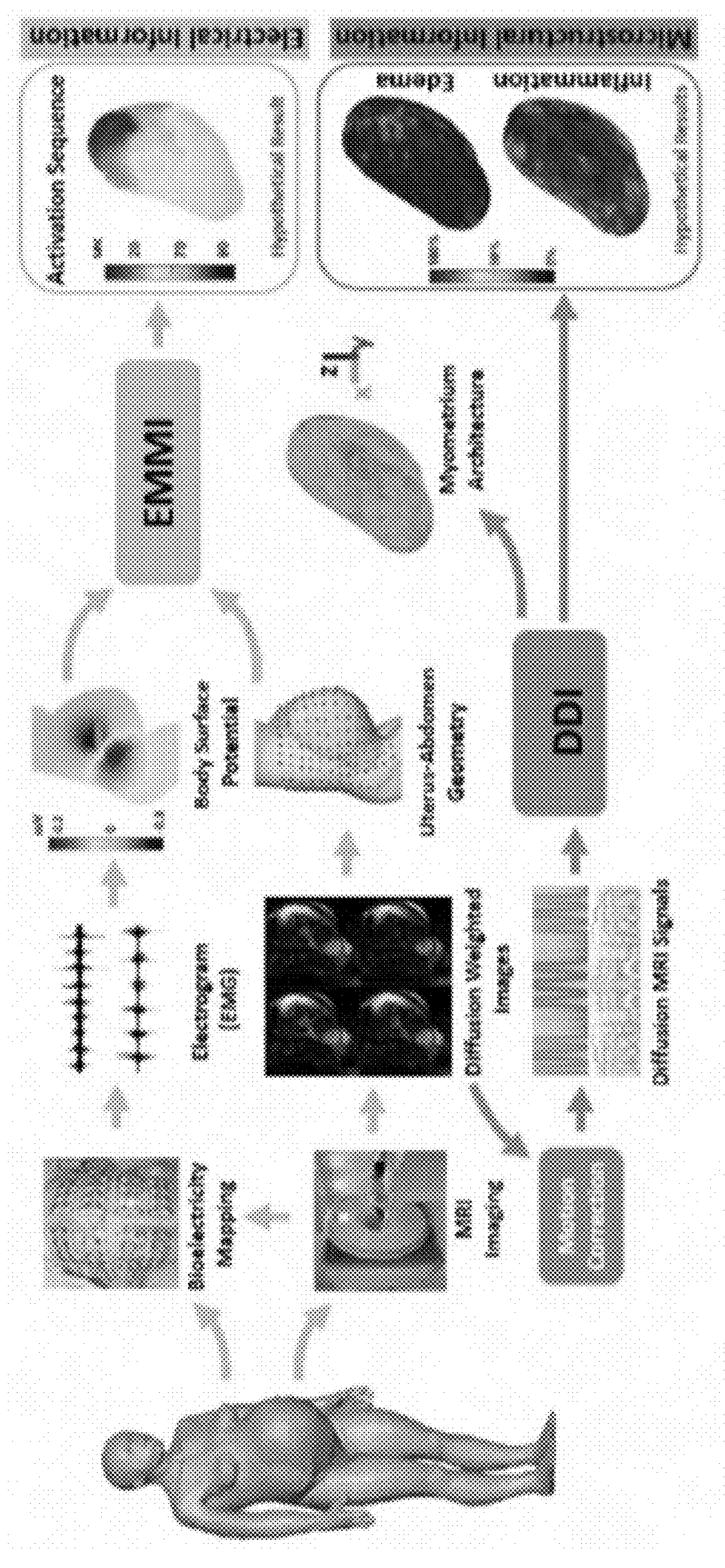
Figure 11C:
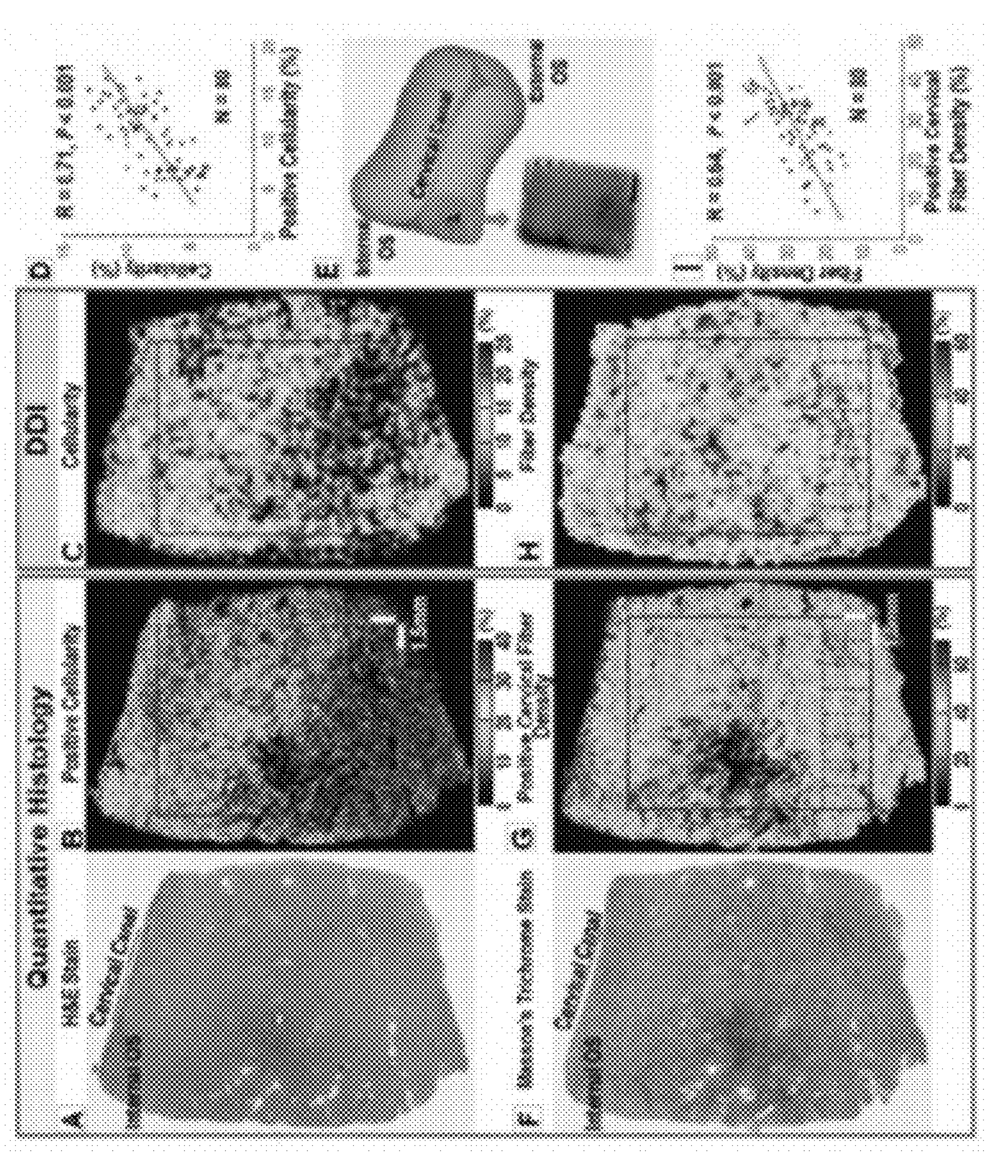

FIGS. 11A-11C illustrate aspects of DDI applications in the human cervix/uterus. FIG. 11A illustrates DDI of cervix inflammation or infiltrated macrophage. FIG. 11A depicts an example of a cervicitis patient and a normal patient with respect to a T2 weighted image, DDI inflammation, and extracellular water. FIG. 11B provides an example process to locate a substrate responsible for abnormal uterine contractions. In this example, MRI imaging may be used to obtain diffusion-weighted images, perform motion correction, perform diffusion of MRI signals, and computationally process and perform DDI to generate hypothetical results. The results may include microstructural information with respect to inflammation and edema. FIG. 11C illustrates exemplary scans of an infiltrated peripheral macrophage in a cervix with respect to quantitative histology and DDI.

Figure 12A:
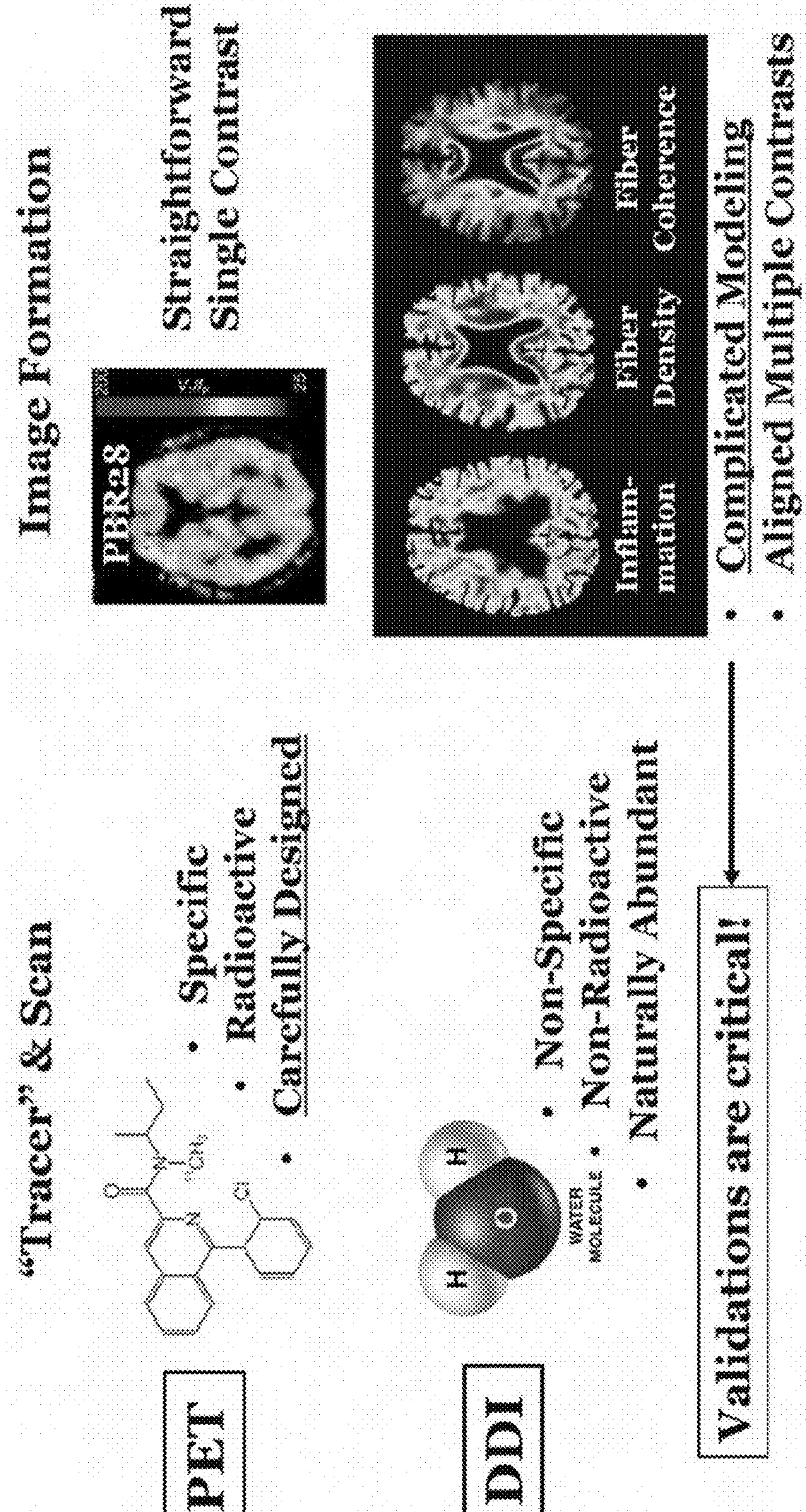
Figure 12B:
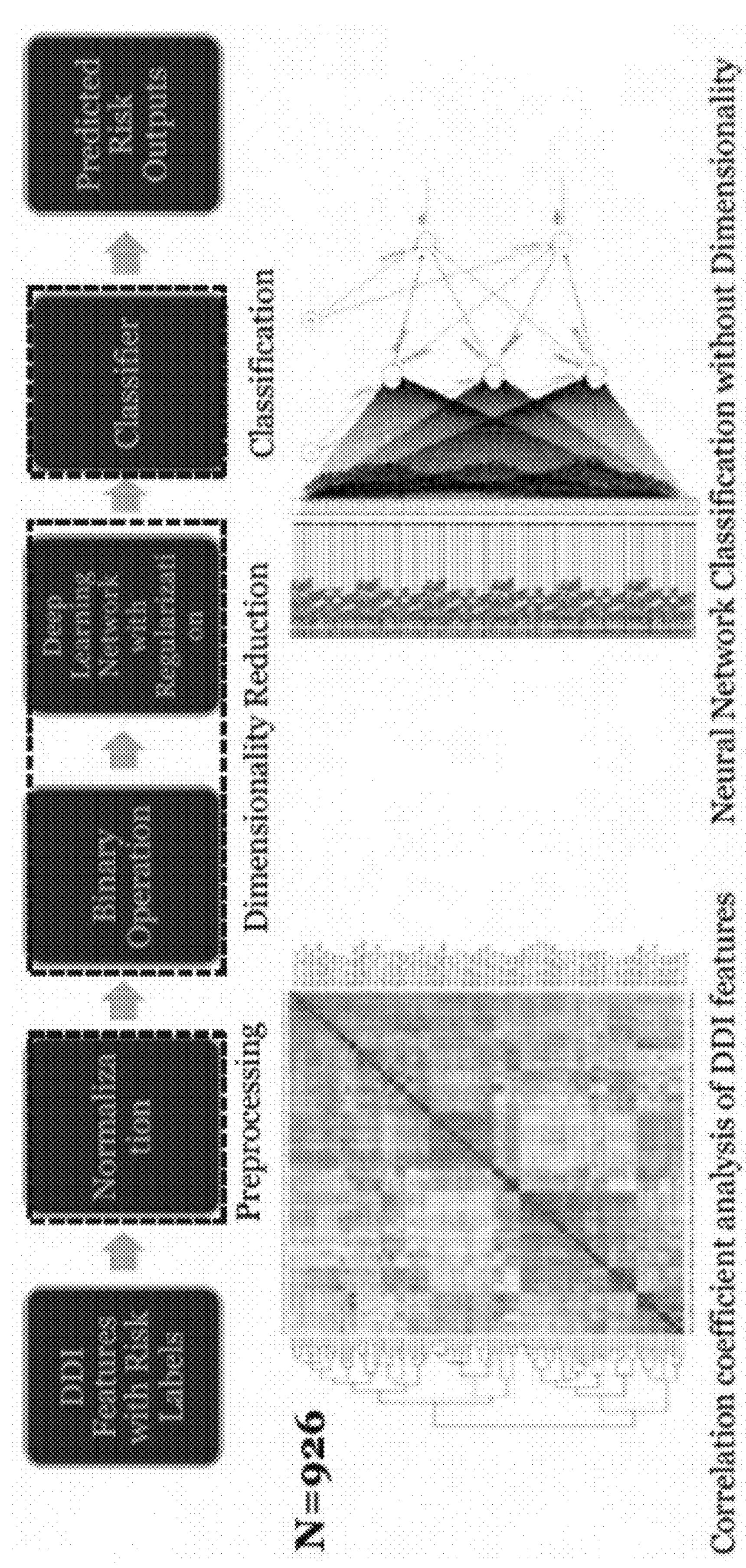
Figures 12D, 12E:
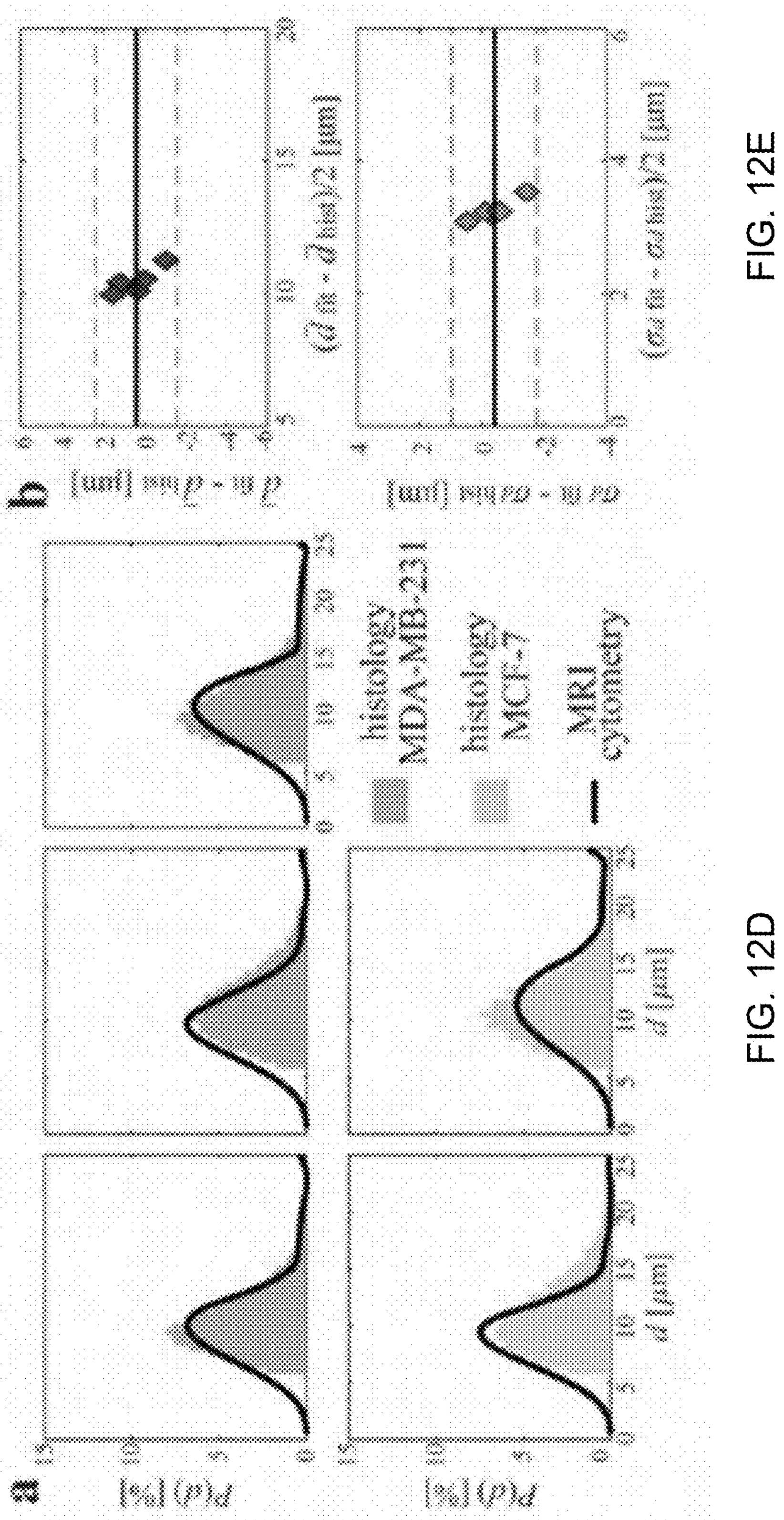
Figure 12F:
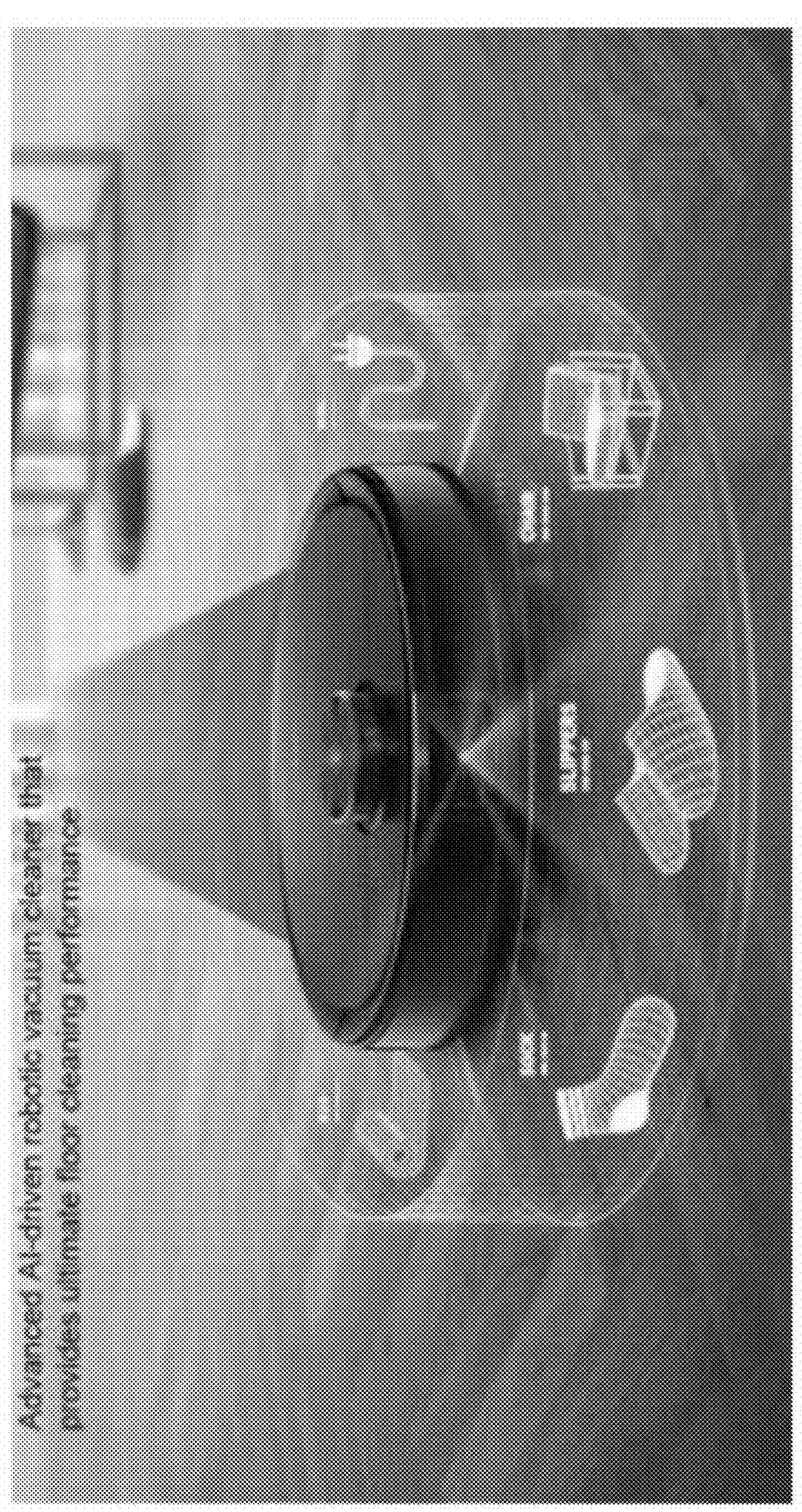
Figure 12G:
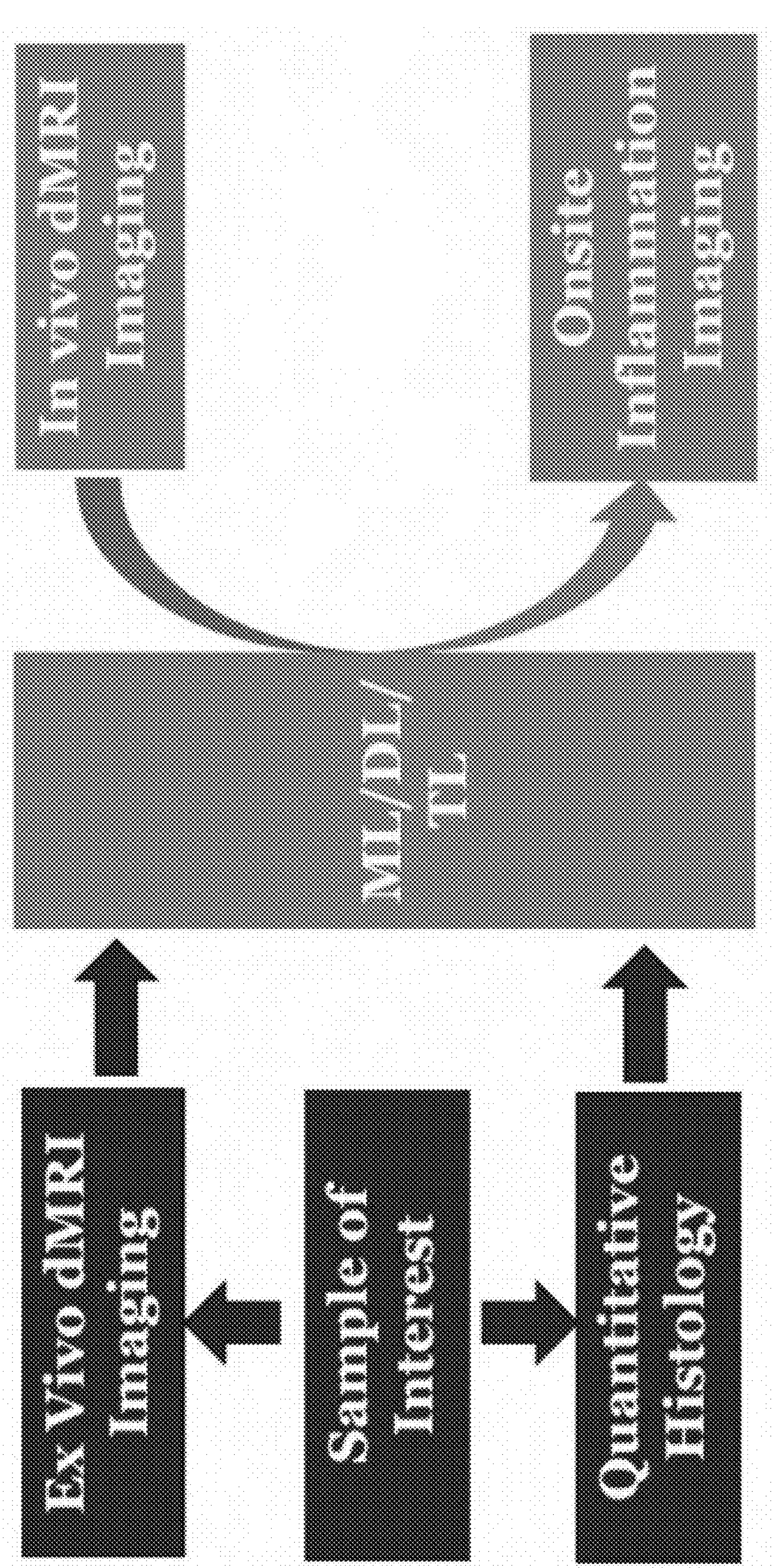

FIGS. 12A-12G illustrate aspects of inflammation imaging as described herein. For example, FIG. 12A depicts a comparison between PET and DDI, where DDI utilizes a water molecule that is non-specific, non-radioactive, and naturally abundant. In contrast, PET is specific, radioactive, and carefully designed. Shown in FIG. 12B is an example of correlation coefficient analysis of DDI features and neural network classification without dimensionality reduction. DDI may be connected with deep learning to predict a clinical outcome. Results of classification testing are illustrated in FIG. 12C. In some embodiments, DDI and deep learning may detect ASD. FIGS. 12D and 12E illustrate DDI and OGSE. For example, FIG. 12D illustrates a comparison of MRI cytometry and histology-derived cell size distribution of mouse tumors in vivo in five tumors. FIG. 12E illustrates Bland-Altman plots showing the agreement of MRI cytometry and light microscopy. In some embodiments, and in view of FIGS. 12F and 12G, DDI may be powered using artificial intelligence.

In some embodiments, the systems and methods described herein may provide a safe, noninvasive, nonradioactive, clinically feasible MRI technique capable of accurately imaging and quantifying neuroinflammation. For example, the MRI technique may be applicable to patients with Alzheimer's disease (AD). Additionally, the systems and methods described herein may provide a clinical imaging modality of key pathological players in different stages of AD. The disclosed provides a nonradioactive diffusion MRI (dMRI) technique, diffusion dictionary imaging (DDI). DDI may employ a compressed sensing (CS) technique that breaks technical barriers that have prevented conventional MRI methods from accurately imaging neuroinflammation. In some embodiments, DDI may be designed to specifically quantify microglia/astrocyte activation and infiltration underlying the neuroinflammation in AD using FDA-approved clinical dMRI sequences that are available on clinical MRI scanners. Additionally, previously collected dMRI data may be analyzed.

In human tissues, microscopic barriers (e.g., membranes) may constrain the free Brownian motion of water molecules, resulting in reduced apparent diffusivity. Within a diffusion time range achievable in most clinical MRI scanners, water molecules inside regular cellular structures (such as neuron cell body, resting microglia/astrocytes, etc.) may experience highly restricted isotropic diffusion, leading to a close to zero apparent diffusion coefficient (ADC) at a typical diffusion time on a clinical scanner. In contrast, neuroinflammation in AD predominately characterized by the activation and infiltration of microglia and astrocyte creates inflammation-specific microstructural changes, including increased soma size and higher cell density. As a result, increased restricted isotropic ADC and increased restricted isotropic diffusion ratio may be used to specifically reflect and reveal inflammatory cell activation and infiltration.

However, dMRI may employ endogenous water diffusion contrast to probe the entire tissue microstructure in a nonspecific fashion. In other words, although the microstructural changes caused by microglia/astrocyte activation and infiltration may generate characteristic dMRI signals associated with neuroinflammation, those signals may be mixed and "buried" with other compartments' diffusion signals coexisting in the same imaging voxel. This is exactly why the conventional single diffusion tensor imaging (DTI) cannot distinguish and extract inflammation signals (immune cell activation/infiltration) from extracellular water (tissue swelling, edema), and from the anatomical complexity (e.g., cross fibers, axonal injury, demyelination, etc.). To increase imaging specificity, multi-compartment models such as free water imaging (FWI), neurite orientation dispersion and density imaging (NODDI), diffusion basis spectrum imaging (DBSI), etc. have been developed by including more microstructural compartments but only with partial success. The fundamental technical challenge is the dilemma that, within the clinically feasible scanning time, a higher order of complexity will increase the imaging specificity, but also decrease the imaging stability and accuracy at the same time. Fortunately, the compressed sensing (CS) technique has enabled major technological progress in other fields by overcoming a similar challenge faced by DDI. Herein, the powerful CS technique may be employed by DDI to break the technical barrier that has prevented conventional dMRI techniques from accurately and specifically imaging neuroinflammation in AD. Specifically, DDI may be able to accurately solve a large number of microstructural compartments and specifically extract neuroinflammation signals by projecting a limited number of clinical images onto an overcomplete dictionary through a regularized CS inverse computation.

Scientific Rigors and Conceptual Framework of DDI

Figure 13:
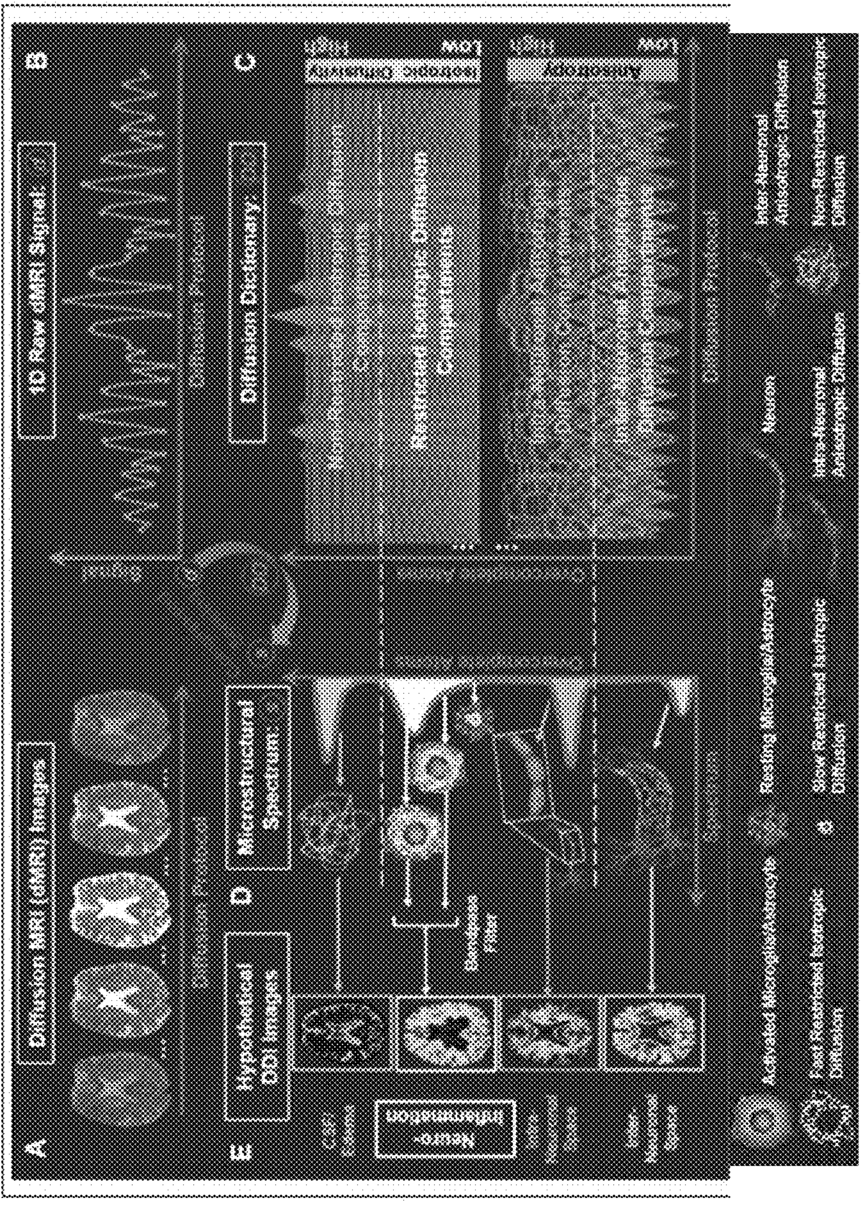
FIG. 13 illustrates an exemplary schematic demonstration of DDI methodology in accordance with at least one embodiment of the present disclosure.

FIG. 13 illustrates a conceptual framework of DDI that may be divided into five main components (Panels A to E in FIG. 13). As shown in FIG. 13: A. Multiple MRI images will be acquired by an FDA-approved dMRI sequence. B. For each imaging voxel, 1D raw dMRI signal vector (d) will be formed. C. An overcomplete diffusion dictionary (DD) containing the dMRI signals simulated from a list of comprehensive microstructural components will be constructed. D. Microstructural spectrum(s) will be computed by projecting the raw dMRI signal onto the diffusion dictionary using a regularized compressed sensing algorithm. E. Band-pass filter will be used to specifically extract neuroinflammation signals in Alzheimer's disease (microglia/astrocyte activation/infiltration). Multiple other DDI images may also be generated at the same time. Hypothetical DDI images are shown in FIG. 13.

Further, with respect to FIG. 13, conducting multiple diffusion weighting dMRI clinical scans is shown (Panel A): DDI relies on the endogenous signals generated by water diffusion to probe neuroinflammation in AD. Specifically, DDI employs clinical dMRI sequences with a multi-direction, multi-weighting diffusion protocol to measure the signal decays caused by water molecule diffusion. Due to the constraints on scanning time, a limited number (N) of dMRI images in the protocol (N=~60 on average) may be acquired within a clinically feasible scan time. Forming 1-dimensional (1D) dMRI signal vector for each brain imaging voxel (Panel B): dMRI signal associated with one imaging voxel (brown dots in Panel A) can be organized into a 1D vector with respect to the diffusion protocol. Named dMRI signal (denoted by an N×1 vector d, brown curve). At the typical spatial resolution of 1 to 2 mm3 on clinical MRI scanners, the size of a single imaging voxel is many orders of magnitude larger than the size of microstructural compartments (on μm scale). The raw diffusion MRI signal reflects the mixtures of a large number of cells, axons, dendrites, inter-axon/dendrite space, etc.

Developing an overcomplete diffusion dictionary (Panel C): DDI may abandon the traditional multi-compartment model description of the complicated intra-voxel heterogeneity. Instead, DDI may develop a large, overcomplete diffusion dictionary (denoted by a matrix DD, row number, L=1600) to contain a large number of coherent atoms of dMRI signals from a comprehensive list of the cerebral anatomical and pathological components (anisotropic white and gray matter tissues, inflammatory cell infiltration and activation, extracellular water component, CSF, etc.). Each row of the DD represents an atom dMRI signal from one type of microstructural component with a specific orientation and diffusion pattern. Classic diffusion tensor theory and Monte Carlo (MC) simulation may be used to compute each atom of the DD using the same diffusion protocol (DD column number=N). The entire microstructural components may be grouped into four categories based on their anatomical and diffusion features: (1) Intra-neuronal diffusion compartments with high anisotropy (green); (2) Inter-neuronal diffusion compartment with low anisotropy (yellow); (3) Non-restricted isotropic diffusion compartments with high diffusivity (cyan); (4) Restricted isotropic diffusion compartments with low diffusivity (white). With the introduction of DD, the raw dMRI signal (Panel B) may be described as the weighted linear summation of the overcomplete atoms in DD (Eq. 1), where s is the L×1 positive weighting vector, e is an L×1 noise vector. The DD (L×N) formulation converts the problem of solving a difficult high dimensional fitting problem employed by conventional dMRI methods into a large ill-posed linear matrix inversion problem, which has been successfully solved in other fields and may be implemented in DDI as described herein.

$$d=DD*s+e;\ (s\geq 0) \quad (1)$$

FIG. 13, Panel C, depicts computing the microstructural spectrum using CS. An overcomplete dictionary such as DD may include a large number of coherent atoms. Due to the redundant property of the overcomplete dictionary, the weighted summation described in Eq.1 has flexible and sparse representation, which may be utilized by a CS technique to effectively compute an accurate microstructural spectrum (the weighting factor, s, blue spectrum in Panel D) from a small number of clinical dMRI images. The flexibility of building the overcomplete DD also increases the "illness" of the ill-posed CS problem. Fortunately, the microstructural spectrum s is a nonnegative signal, which can be used as an extra piece of prior knowledge for the CS computation to avoid overfitting. Specifically, the non-negative CS formulation is shown in Eq.2.

$$\underset{x\geq 0}{\text{minimize}}\ \|d-DDs\|_2^2+\gamma\|s\|_1 \quad (2)$$

Where the first term is the data consistency term in L2 norm space, the second term is the sparsity constrain in L1 norm space is a positive constant controlling the degree of sparsity of s. Note that depends on many factors such as the signal sparsity and level of measurement noise in signal d. In some embodiments, the adaptive lasso method may be used to find and solve Eq. 2. Similar methods have been used successfully in other fields such as economics, hyperspectral unmixing, face recognition, etc. Forming the DDI imaging biomarker of neuroinflammation and other microstructural features is shown in Panel E of FIG. 13. One of the key innovations underlying DDI is to reliably extract and quantify the signal specific to the neuroinflammation in AD from the computed microstructural spectrum. In DDI, the microstructural spectrum corresponding to the restricted isotropic diffusion (white area in Panel D) may be grouped to reflect the entire cellularity compartments, which contain regular cellular structures and the neuroinflammation signals that DDI aims to obtain. By applying a band-pass isotropic diffusion filter onto the restricted isotropic diffusion part of the microstructural spectrums, moderate to fast restricted isotropic diffusion associated with microglia/astrocyte activation and infiltration may be specifically extracted for each imaging voxel. Specifically, DDI cellular fraction (an estimation of the activated microglia/astrocyte infiltration) and DDI cellular diffusivity (an estimation of the microglia/astrocyte activation) may be quantified and multiplied to generate DDI neuroinflammation index to quantify the neuroinflammation in AD. Moreover, the extra "bonus" of using DDI to probe the entire microstructural complexity is that multiple additional images reflecting the conditions of anisotropic compartments and CSF/edema may be generated at the same time of imaging neuroinflammation. For example, the microstructural spectrum corresponding to the intra-neuronal diffusion (green area in Panel D) may be grouped to reflect the neuronal integrities. The microstructural spectrum corresponding to the inter-neuronal diffusion (yellow area in Panel D) may be grouped to reflect the inter-neuronal space. The microstructural spectrum corresponding to the non-restricted isotropic diffusion (cyan area in Panel D) may be grouped to reflect the edema and CSF.

Conceptual and Technical Feasibilities of DDI

A fundamental challenge that DDI aims to harness is to disentangle the complex intra-voxel microstructural heterogeneity and extract signals specific to microglia/astrocyte activation and infiltration in AD neuroinflammation using a limited number of clinical dMRI measurements. The conceptual feasibility of DDI is well supported by two types of novel imaging techniques that have been successfully developed and clinically translated recently: electrophysiological imaging and magnetic resonance fingerprinting. Both of these innovative imaging techniques share and overcome similar challenges targeted by DDI.

Electrophysiological imaging (EI) of high-resolution 3D organ surface electrical activation patterns: To overcome the poor specificity of 150-years-old ECG technique in imaging cardiac electrical activation, the first clinically EI system electrocardiographic imaging (ECGI) was invented to image the high-resolution epicardial surface electrical activation sequence during normal and abnormal cardiac rhythms. In ECGI, a small number of ECG electrodes are placed on the body surface to record ECG signals from different angles and locations on the torso relative to the heart. Each ECG signal (kt in FIG. 14) is analog to one raw dMRI signal with a unique diffusion gradient in DDI. The large transfer/sensing matrix (A) was derived based on the electrostatic and bi-domain theory, which is analog to the DDI dictionary derived based on diffusion tensor theory. Although each body surface ECG signal may contain nonspecific, averaged electrical information generated by the entire heart, the inverse computation in ECGI enables specific, high-resolution imaging of heart surface ECG signal and activation patterns (rt in FIG. 14), which is analog to the microstructural spectrum in DDI. Based on the sparse spatial and temporal distribution of activation wavefront, a sparse sensing method has been used to solve ECGI. Recently, another electrophysiological imaging system was also successfully developed for uterine contractions during labor. Although EI systems were developed for functional electrical imaging, the conceptual similarity between EI and DDI is very high.

The success of EI support DDI's conceptual feasibility of projecting limited measured dMRI signals onto the diffusion dictionary to generate microstructural spectrum using the CS technique (FIG. 13).

Figure 14:
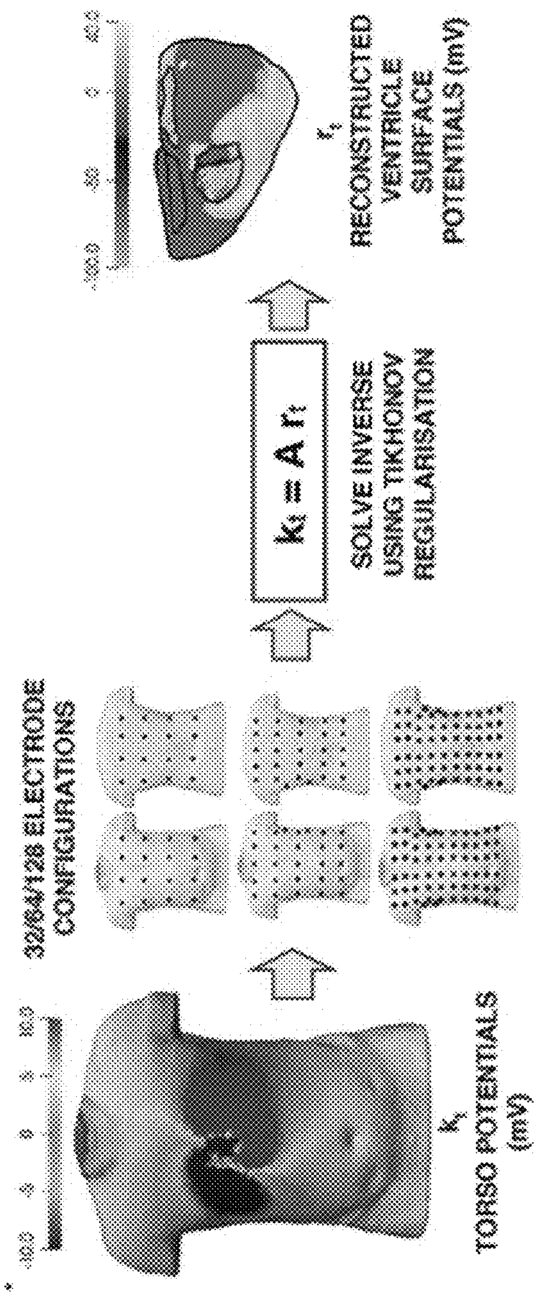
FIG. 14 illustrates an exemplary ECGI workflow.

FIG. 14 illustrates an exemplary ECGI Workflow. The patient's torso potential (kt) is measured using a multi-lead (32¬128) ECG configuration. Torso potential (kt) reflects the electrical activities generated by the entire heart and cannot locate the ectopic focus of arrhythmia on the heart. Transfer matrix (A) is computed from patient-specific body-heart geometry based on electrostatic theory. By projecting torso potential signal (kt) onto the transfer matrix and solving an ill-posed inverse problem, the high-resolution epicardial potentials (rt) can be accurately imaged by ECGI to guide the ablation of the ectopic focus. ECGI improved the ECG's specificity and resolution by modeling and solving a large underdetermined system.

Magnetic resonance fingerprinting (MRF) of tissue relaxation properties: MRF was recently developed for imaging brain T1 and T2 values, and later the similar concepts were adopted for other applications. MRF-type techniques allow simultaneous measurement of multiple tissue properties in a single, time-efficient acquisition (see FIG. 15). In MRF, under-sampled images were acquired, analog to the small number of dMRI images in DDI. Similarly, MRF may develop an overcomplete dictionary based on the Block equations or Bloch image simulation. The pattern matching method may be used to solve the T1 and T2 values for each voxel. Although MRF techniques usually require a specially designed MRI sequence to acquire the needed MRI signals, it demonstrates the conceptual feasibility of using limited MRI measurements and a very large dictionary (1000×5970) to solve and generate different contrasts simultaneously. Thus, the MRF technique supports the DDI conceptual design to generate a detailed spectrum and multiple microstructural contrasts (See FIG. 13, Panels B to E). The successes of EI and MRF-related techniques prove that the DDI has high conceptual feasibility and holds great promise.

Figure 15:
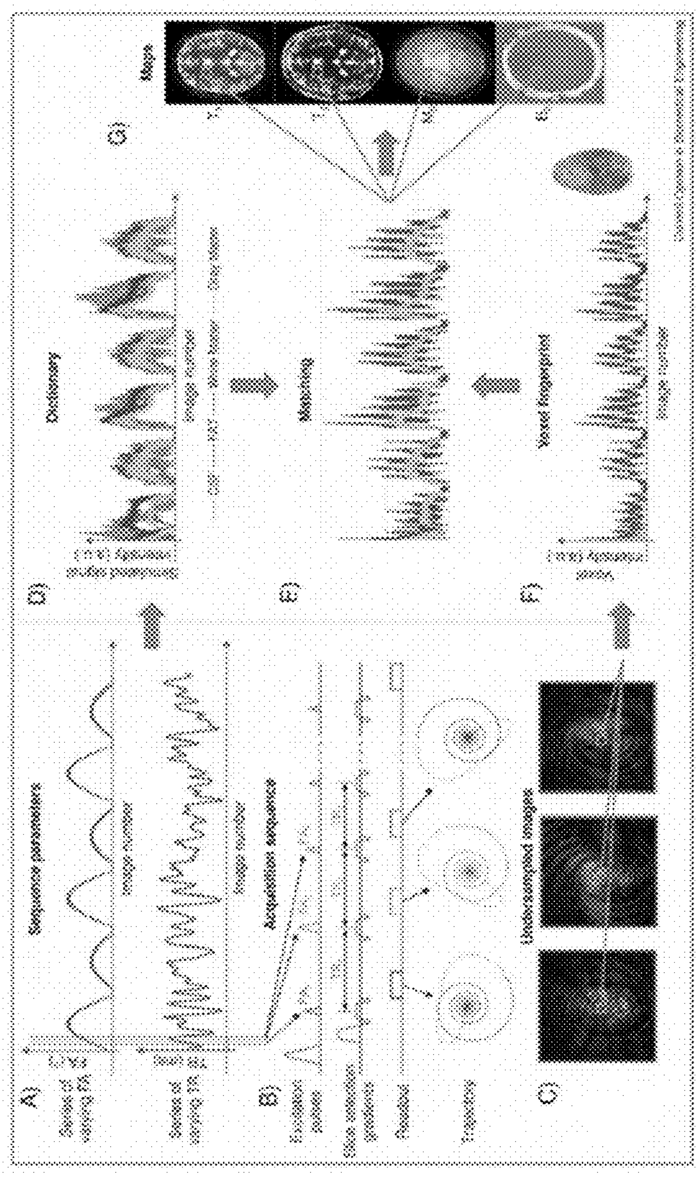
FIG. 15 illustrates an exemplary MRF workflow.

FIG. 15 illustrates an exemplary MRF workflow. The flowchart shows an overview of the MRF framework as used for MR-True Fast Imaging with Steady State Precession acquisition. (A) Shows an example of variable flip angles and time of repetition used for this acquisition. (B) Sequence diagram showing the excitation pulses, slice selection gradients, readout, and k-space trajectory for each time of repetition (TR) (C) shows three under-sampled images acquired in different TR. (D) Shows examples of four "dictionary" entries representing four main tissues; cerebrospinal fluid, fat, white matter, and gray matter. (E) Shows pattern matching of the voxel fingerprint with the closest entry in the dictionary, which allows the retrieval of the tissue features represented by that voxel. (F) Shows intensity variation of a voxel across the under-sampled images. (G) Shows parameter maps obtained by repeating the matching process for each voxel.

With the use of water molecule diffusion to probe neuroinflammation, DDI can noninvasively image and quantify neuroinflammation in AD without the need to inject a contrast agent or radioactive tracer. The unique microstructural changes during neuroinflammation in the AD brain include the infiltration of activated microglia and astrocytes, which will be quantified as the elevated restricted isotropic diffusion (DDI inflammation index). The dMRI sequence employed by DDI has been approved by the FDA and is standard on most clinical MRI systems worldwide. Thus, the potential use of DDI can readily be translated to multicenter clinical trials and is widely accessible to hospitals and patients.

The use of regularized CS to image neuroinflammation can be used with a short clinical scan. Acquiring sufficient data to solve a large number of equations necessary to assign each water diffusion signal to an atom in the diffusion dictionary has traditionally required a very long scan time. Such a long acquisition time could significantly reduce the patients' compliance, especially in the elderly population. Regularized CS, as employed by DDI, can reconstruct complicated intra-voxel signals and images from significantly fewer measurements than were traditionally thought necessary. Moreover, DDI can be applied to the dMRI data previously collected in the Knight ADRC and DIAN projects.

Further, measures of CSF and plasma glial fibrillary acidic protein- (GFAP): The GFAP has previously been reported to associate with AD pathology. GFAP is a key intermediate filament protein and marker of reactive astrocytes, whose expression has been associated with amyloid plaque load. This can be added as a measure as one of the CSF and plasma inflammation markers and compared with the DDI neuroinflammation index.

The DIAN and Knight ADRC cohorts are rich and complimentary for the development and establishment of DDI: The DIAN observational study (R. J. Bateman, PI, see LOS) has provided insight into the pathogenesis of AD by studying individuals with autosomal dominant AD (ADAD). ADAD patients have "pure" Amyloid-beta driven pathologies and are relatively young without significant vascular disease and other comorbidities. In comparison, Knight ADRC (J. C. Morris, PI, see LOS) studies the sporadic AD patients representing a more "real world" set of older AD patients. The combination of the rich DIAN and ADRC datasets provides an ideal platform to thoroughly develop and translate DDI using the rich data collected over the years. In addition, this enables cost-effective evaluation of temporal evolution and spatial distribution of neuroinflammation in both DIAN and ADRC cohorts and the study of their similarity and difference.

Simultaneous imaging of neuronal integrity by DDI: DDI can simultaneously image and quantify neuroinflammation and neuronal integrity. The naturally aligned neuronal integrity DDI images may help provide a better understanding of the role of neuroinflammation in AD pathogenesis and disease progression.

Machine Learning and Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data to facilitate making predictions for subsequent data. Models may be created based upon example inputs to make valid and reliable predictions for novel inputs.

Additionally or alternatively, the machine learning programs may be trained by inputting sample data sets or certain data into the programs, such as images, object statistics and information, audio and/or video records, text, and/or actual true or false values. The machine learning programs may utilize deep learning algorithms that may be primarily focused on pattern recognition and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or other types of machine learning or artificial intelligence.

In supervised machine learning, a processing element may be provided with example inputs and their associated outputs and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

In some embodiments, a computing device may be configured to implement machine learning, such that the computing device "learns" to analyze, organize, and/or process data without being explicitly programmed. Machine learning may be implemented through machine learning (ML) methods and algorithms. In one aspect, a machine learning (ML) module may be configured to implement ML methods and algorithms. In some embodiments, ML methods and algorithms may be applied to data inputs and generate machine learning (ML) outputs. Data inputs may include, but are not limited to, images or frames of a video, object characteristics, and object categorizations. Data inputs may further include sensor data, image data, video data, telematics data, authentication data, authorization data, security data, mobile device data, geolocation information, transaction data, personal identification data, financial data, usage data, weather pattern data, "big data" sets, and/or user preference data. ML outputs may include, but are not limited to, a tracked shape output, categorization of an object, categorization of a type of motion, a diagnosis based on motion of an object, motion analysis of an object, and trained model parameters ML outputs may further include speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some embodiments, data inputs may include certain ML outputs.

In some embodiments, at least one of a plurality of ML methods and algorithms may be applied, which may include, but are not limited to, genetic algorithms, linear or logistic regressions, instance-based algorithms, regularization algorithms, decision trees, Bayesian networks, cluster analysis, association rule learning, artificial neural networks, deep learning, dimensionality reduction, and support vector machines. Additionally, the implemented ML methods and algorithms may be directed toward at least one of a plurality of categorizations of machine learning, such as supervised learning, unsupervised learning, and reinforcement learning.

ADDITIONAL CONSIDERATIONS

As will be appreciated based upon the foregoing specification, the above-described embodiments of the disclosure may be implemented using computer programming or engineering techniques including computer software, firmware, hardware, or any combination or subset thereof. Any such resulting program, having computer-readable code means, may be embodied, or provided within one or more computer-readable media, thereby making a computer program product, i.e., an article of manufacture, according to the discussed embodiments of the disclosure. The computer-readable media may be, but is not limited to, a fixed (hard) drive, diskette, an optical disk, a magnetic tape, a semiconductor memory, such as read-only memory (ROM), a transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps," or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable and include any computer program stored in memory for execution by a processor, including RAM memory, ROM memory, EPROM memory, EEPROM memory, and non-volatile RAM (NVRAM) memory. The above memory types are examples only and are thus not limiting as to the types of memory usable for the storage of a computer program.

In one embodiment, a computer program is provided, and the program is embodied on a computer readable medium. In an example embodiment, the system is executed on a single computer system, without requiring a connection to a server computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various environments without compromising any major functionality.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independently and separate from other components and processes described herein. Each component and process can also be used in combination with other assembly packages and processes.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A diffusion dictionary imaging (DDI) computing device for inflammation imaging, the DDI computing device comprising at least one processor in communication with at least one memory device, wherein the at least one processor is programmed to:

receive, from at least one user device, one or more magnetic resonance (MR) signals;

record the one or more MR signals to the at least one memory device;

retrieve one or more DDI algorithms from the at least one memory device, the DDI algorithms including extraction of neuroinflammation signals;

retrieve, from a diffusion dictionary, one or more microstructural component diffusion patterns;

process the one or more MR signals to reconstruct a diffusion MRI image using the retrieved one or more DDI algorithms and the one or more microstructural component diffusion patterns; and output the reconstructed diffusion MRI image.

2. The DDI computing device of claim 1, wherein the one or more MR signals are detected by a clinical MRI scanner configured to provide longitudinal imaging.

3. The DDI computing device of claim 1, wherein to process the one or more MR signals, the at least one processor is further programmed to:

extract one or more values from the one or more MR signals; and input the one or more values into the one or more DDI algorithms to reconstruct the diffusion MRI image.

4. The DDI computing device of claim 1, wherein the at least one processor is further programmed to:

define a weighted apparent diffusion coefficient (wADC); and capture one or more microstructure hallmarks of the diffusion MRI image, wherein the one or more microstructure hallmarks is associated with immune cell activation during an inflammation process;

wherein the wADC is based at least in part on a computation of the DDI computing device.

5. The DDI computing device of claim 1, wherein the at least one processor is further configured to:

detect one or more microstructural features of the diffusion MRI image; and associate the one or more microstructural features with at least one immune response.

6. The DDI computing device of claim 1, wherein the at least one processor is programmed to determine a DDI neuroinflammation index based at least in part on the reconstructed diffusion MRI image.

7. The DDI computing device of claim 1, wherein the at least one processor is programmed to compute one or more microstructural spectrum by projecting the one or more MR signals onto the diffusion dictionary through a regularized compressed sensing (CS) inverse computation.

8. The DDI computing device of claim 7, wherein the diffusion dictionary comprises an overcomplete dictionary.

9. A non-transitory computer readable medium comprising instructions for inflammation imaging, the instructions, when executed by at least one processor, implement:

receiving one or more magnetic resonance (MR) signals;

recording the one or more MR signals to at least one memory device;

retrieving one or more DDI algorithms from the at least one memory device;

retrieving, from a diffusion dictionary, one or more microstructural component diffusion patterns;

reconstructing a diffusion MRI image based on the one or more MR signals using the retrieved one or more DDI algorithms and the one or more microstructural component diffusion patterns, the DDI algorithms including extraction of neuroinflammation signals;

detecting one or more microstructural features of the reconstructed diffusion MRI image; and associating the one or more microstructural features with at least one immune response.

10. The non-transitory computer readable medium of claim 9, wherein the one or more MR signals are detected by a clinical MRI scanner configured to provide longitudinal imaging.

11. The non-transitory computer readable medium of claim 9, wherein the instructions, when executed by at least one processor, further implement:

extracting one or more values from the one or more MR signals; and inputting the one or more values into the one or more DDI algorithms to reconstruct the diffusion MRI image.

12. The non-transitory computer readable medium of claim 9, wherein the instructions, when executed by at least one processor, further implement:

defining a weighted apparent diffusion coefficient (wADC); and capturing one or more microstructure hallmarks of the diffusion MRI image, wherein the one or more microstructure hallmarks is associated with immune cell activation during an inflammation process;

wherein the wADC is based at least in part on a computation of the DDI computing device.

13. The non-transitory computer readable medium of claim 9, wherein the instructions, when executed by at least one processor, further implement computing one or more microstructural spectrum by projecting the one or more MR signals onto the diffusion dictionary through a regularized compressed sensing (CS) inverse computation.

14. A system, comprising:

at least one MRI scanner coupled to a network, wherein the at least one MRI scanner configured to:

detect one or more MRI signals; and transmit the one or more MRI signals over a network;

a diffusion dictionary imaging (DDI) computing device, the DDI computing device including at least one memory and a processor, wherein the DDI computing device is coupled to the network and is configured to:

receive the one or more MR signals from the at least one MRI scanner via the network;

record the one or more MR signals to the at least one memory device;

retrieve one or more DDI algorithms from the at least one memory device;

retrieving, from a diffusion dictionary, one or more microstructural component diffusion patterns;

reconstruct a diffusion MRI image based on the one or more MR signals using the retrieved one or more DDI algorithms and the one or more microstructural component diffusion patterns, the DDI algorithms including extraction of neuroinflammation signals;

detect one or more microstructural features of the reconstructed diffusion MRI image; and associate the one or more microstructural features with at least one immune response.

15. The system of claim 14, wherein the MRI scanner is a clinical MRI scanner configured to provide longitudinal imaging.

16. The system of claim 14, wherein the DDI computing device is further configured to:

extract one or more values from the one or more MR signals; and input the one or more values into the one or more DDI algorithms when reconstructing the diffusion MRI image.

17. The system of claim 16, wherein the one or more values are extracted using artificial intelligence, machine learning, or both.

18. The system of claim 14, wherein the DDI computing device is further configured to:

define a weighted apparent diffusion coefficient (wADC); and capture one or more microstructure hallmarks of the diffusion MRI image, wherein the one or more microstructure hallmarks is associated with immune cell activation during an inflammation process;

wherein the wADC is based at least in part on a computation of the DDI computing device.

19. The system of claim 18, wherein the DDI computing device is further configured to:

associate the one or more microstructural features with at least one immune response.

20. The system of claim 18, wherein the DDI computing device is further configured to compute one or more microstructural spectrum by projecting the one or more MR signals onto the diffusion dictionary through a regularized compressed sensing (CS) inverse computation.

* * * * *